(12) United States Patent
Rowe et al.

(10) Patent No.: US 11,944,538 B2
(45) Date of Patent: Apr. 2, 2024

(54) METHODS FOR REDUCING CARDIAC VALVE REGURGITATION

(71) Applicant: Edwards Lifesciences Corporation, Irvine, CA (US)

(72) Inventors: Stanton J. Rowe, Newport Coast, CA (US); Robert S. Schwartz, Inver Grove Heights, MN (US); Robert A. Van Tassel, Irvine, CA (US); Vivian Khalil, San Gabriel, CA (US); Erin M. Spinner, Carlsbad, CA (US); Neil S. Zimmerman, Redwood City, CA (US); Alexander J. Siegel, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 137 days.

(21) Appl. No.: 17/750,210

(22) Filed: May 20, 2022

(65) Prior Publication Data

US 2022/0280291 A1   Sep. 8, 2022

Related U.S. Application Data

(63) Continuation of application No. 16/389,290, filed on Apr. 19, 2019, now Pat. No. 11,344,411, which is a
(Continued)

(51) Int. Cl.
*A61F 2/24* (2006.01)
(52) U.S. Cl.
CPC .......... *A61F 2/2427* (2013.01); *A61F 2/2433* (2013.01); *A61F 2/2454* (2013.01); *A61F 2/246* (2013.01); *A61F 2/2463* (2013.01); *A61F 2/2466* (2013.01); *A61F 2/2424* (2013.01); *A61F 2210/0014* (2013.01);
(Continued)

(58) Field of Classification Search
CPC ...... A61F 2210/0014; A61F 2250/0003; A61F 2250/001; A61F 2/2427; A61F 2/2433; A61F 2/2454; A61F 2/246; A61F 2/2463; A61F 2/2466
See application file for complete search history.

(56) References Cited

U.S. PATENT DOCUMENTS 5,167,239 A   12/1992   Cohen et al.
5,735,842 A   4/1998    Krueger et al.
(Continued)

FOREIGN PATENT DOCUMENTS

WO   2006127509 A2   11/2006
WO   2007050256 A2   5/2007

*Primary Examiner* — Ashley L Fishback
(74) *Attorney, Agent, or Firm* — Anya Adams

(57) ABSTRACT

A method of reducing regurgitation between native leaflets of an atrioventricular heart valve includes advancing a delivery catheter through a sheath, wherein the delivery catheter has a valve leaflet coaptation element mounted over a distal end portion. The coaptation element is positioned within the heart valve and is permitted to radially expand from a compressed configuration to an enlarged configuration for filling a gap between the native leaflets of the heart valve. After deployment, the position of the coaptation element is fixed relative to the heart valve, thereby reducing regurgitation between the native leaflets of the heart valve and improving heart function.

18 Claims, 31 Drawing Sheets

Related U.S. Application Data continuation of application No. 15/296,887, filed on Oct. 18, 2016, now Pat. No. 10,285,812, which is a continuation of application No. 13/895,572, filed on May 16, 2013, now Pat. No. 9,474,605.

(60) Provisional application No. 61/647,973, filed on May 16, 2012, provisional application No. 61/734,728, filed on Dec. 7, 2012.

(52) U.S. Cl.
CPC .............. *A61F 2210/0061* (2013.01); *A61F 2230/0023* (2013.01); *A61F 2250/0003* (2013.01); *A61F 2250/001* (2013.01)

(56) References Cited

U.S. PATENT DOCUMENTS

| | | | |
|---|---|---|---|
| 6,050,972 A | 4/2000 | Zadno-Azizi et al. |
| 6,217,567 B1 | 4/2001 | Zadno-Azizi et al. |
| 6,482,228 B1 | 11/2002 | Norred |
| 6,629,534 B1 | 10/2003 | St. Goar et al. |
| 6,764,510 B2 | 7/2004 | Vidlund et al. |
| 6,875,197 B1 | 4/2005 | Simhambhatla et al. |
| 6,994,092 B2 | 2/2006 | van der Burg et al. |
| 7,070,616 B2 | 7/2006 | Majercak et al. |
| 7,077,862 B2 | 7/2006 | Vidlund et al. |
| 7,160,322 B2 | 1/2007 | Gabbay |
| 7,320,665 B2 | 1/2008 | Vijay |
| 7,322,957 B2 | 1/2008 | Kletschka et al. |
| 7,404,824 B1 | 7/2008 | Webler et al. |
| 7,556,646 B2 | 7/2009 | Yang et al. |
| 7,678,145 B2 | 3/2010 | Vidlund et al. |
| 7,785,366 B2 | 8/2010 | Maurer et al. |
| 7,815,580 B2 | 10/2010 | Viswanathan |
| 7,854,762 B2 | 12/2010 | Speziali et al. |
| 7,901,454 B2 | 3/2011 | Kapadia et al. |
| 7,927,370 B2 | 4/2011 | Webler et al. |
| 7,942,928 B2 | 5/2011 | Webler et al. |
| 8,007,428 B2 | 8/2011 | Vijay |
| 8,070,805 B2 | 12/2011 | Vidlund et al. |
| 8,080,808 B2 | 12/2011 | Norris |
| 8,092,525 B2 | 1/2012 | Eliasen et al. |
| 8,133,213 B2 | 3/2012 | Lashinski |
| 8,216,302 B2 | 7/2012 | Wilson et al. |
| 8,449,606 B2 | 5/2013 | Eliasen et al. |
| 8,460,370 B2 | 6/2013 | Zakay |
| 8,486,136 B2 | 7/2013 | Maurer et al. |
| 8,579,967 B2 | 11/2013 | Webler et al. |
| 8,758,430 B2 | 6/2014 | Ferrari et al. |
| 8,758,432 B2 | 6/2014 | Solem |
| 8,778,017 B2 | 7/2014 | Eliasen et al. |
| 8,845,717 B2 | 9/2014 | Khairkhahan et al. |
| 8,888,843 B2 | 11/2014 | Khairkhahan et al. |
| 8,888,844 B2 | 11/2014 | Eliasen et al. |
| 8,932,348 B2 | 1/2015 | Solem et al. |
| 9,161,837 B2 | 10/2015 | Kapadia |
| 9,232,998 B2 | 1/2016 | Wilson et al. |
| 9,232,999 B2 | 1/2016 | Maurer et al. |
| 9,259,317 B2 | 2/2016 | Wilson et al. |
| 9,289,297 B2 | 3/2016 | Wilson et al. |
| 9,474,605 B2 | 10/2016 | Rowe et al. |
| 9,636,223 B2 | 5/2017 | Khalil et al. |
| 2003/0050694 A1 | 3/2003 | Yang et al. |
| 2003/0120341 A1 | 6/2003 | Shennib et al. |
| 2003/0187494 A1 | 10/2003 | Loaldi |
| 2004/0098081 A1 | 5/2004 | Landreville et al. |
| 2004/0225233 A1 | 11/2004 | Frankowski et al. |
| 2004/0267280 A1 | 12/2004 | Nishide et al. |
| 2005/0038508 A1 | 2/2005 | Gabbay |
| 2006/0058871 A1* | 3/2006 | Zakay .................. A61F 2/246 623/2.18 |
| 2006/0241745 A1 | 10/2006 | Solem |
| 2007/0093890 A1 | 4/2007 | Eliasen et al. |
| 2007/0162071 A1 | 7/2007 | Burkett et al. |
| 2007/0198082 A1 | 8/2007 | Kapadia et al. |
| 2007/0219627 A1 | 9/2007 | Chu et al. |
| 2007/0255399 A1 | 11/2007 | Eliasen et al. |
| 2007/0265700 A1 | 11/2007 | Eliasen et al. |
| 2007/0270943 A1 | 11/2007 | Solem et al. |
| 2007/0282429 A1 | 12/2007 | Hauser et al. |
| 2008/0288061 A1 | 11/2008 | Maurer et al. |
| 2009/0048668 A1 | 2/2009 | Wilson et al. |
| 2009/0069885 A1 | 3/2009 | Rahdert et al. |
| 2009/0131880 A1 | 5/2009 | Speziali et al. |
| 2009/0137968 A1 | 5/2009 | Rottenberg |
| 2010/0022948 A1 | 1/2010 | Wilson et al. |
| 2010/0198347 A1 | 8/2010 | Zakay et al. |
| 2010/0298929 A1 | 11/2010 | Thornton et al. |
| 2011/0077733 A1 | 3/2011 | Solem |
| 2011/0184512 A1 | 7/2011 | Webler et al. |
| 2011/0224784 A1 | 9/2011 | Quinn |
| 2011/0288577 A1 | 11/2011 | Newhauser et al. |
| 2012/0143320 A1 | 6/2012 | Eliasen et al. |
| 2013/0190798 A1 | 7/2013 | Kapadia |
| 2013/0325110 A1 | 12/2013 | Khalil et al. |
| 2013/0338763 A1 | 12/2013 | Rowe et al. |
| 2014/0309732 A1 | 10/2014 | Solem |

\* cited by examiner

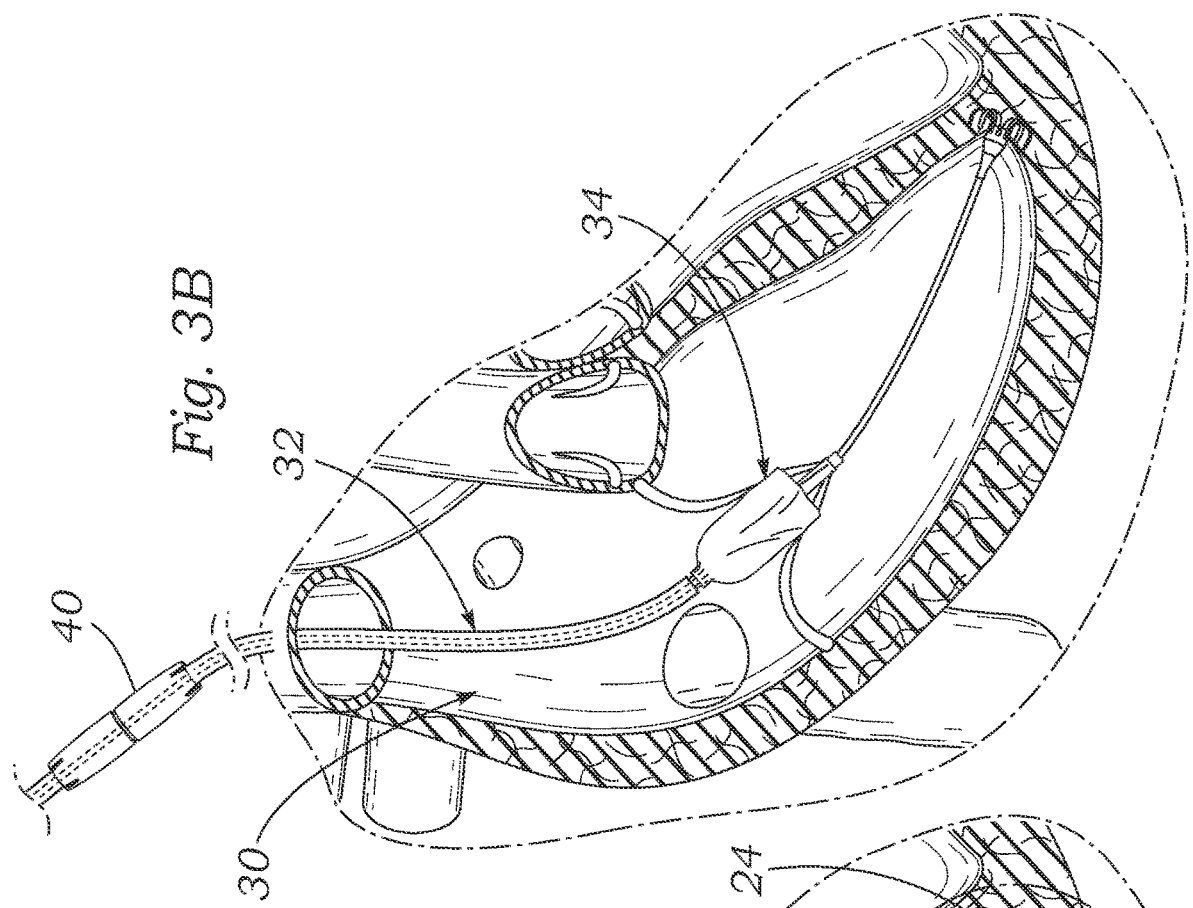
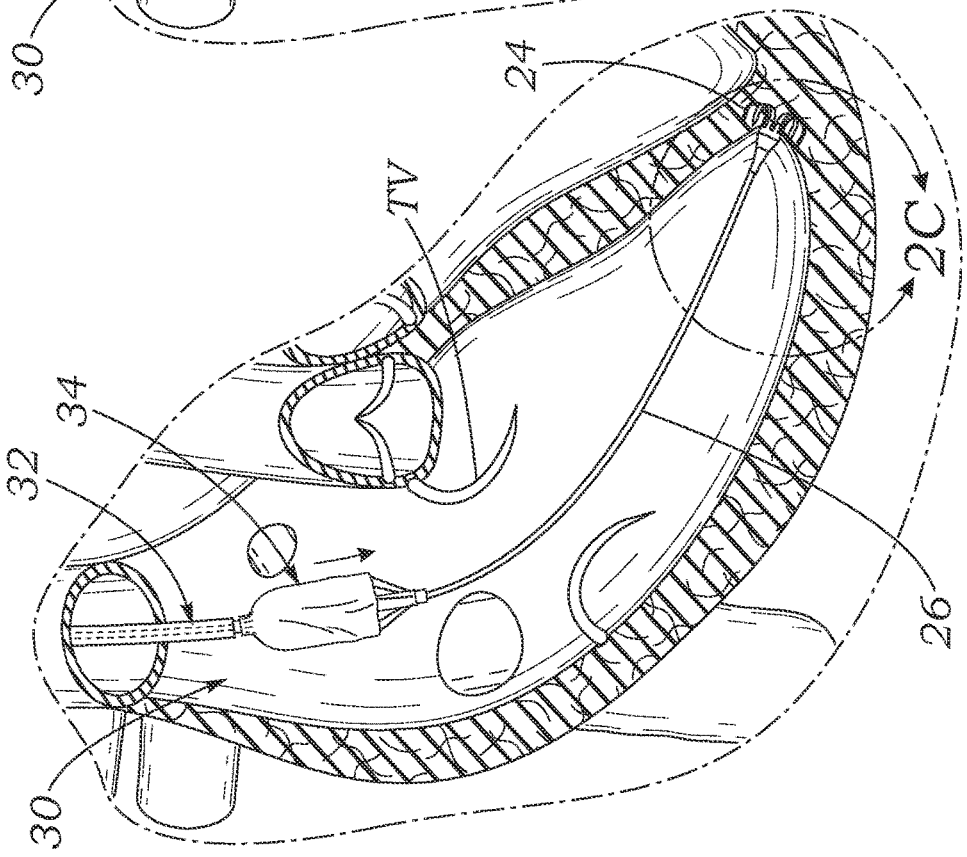

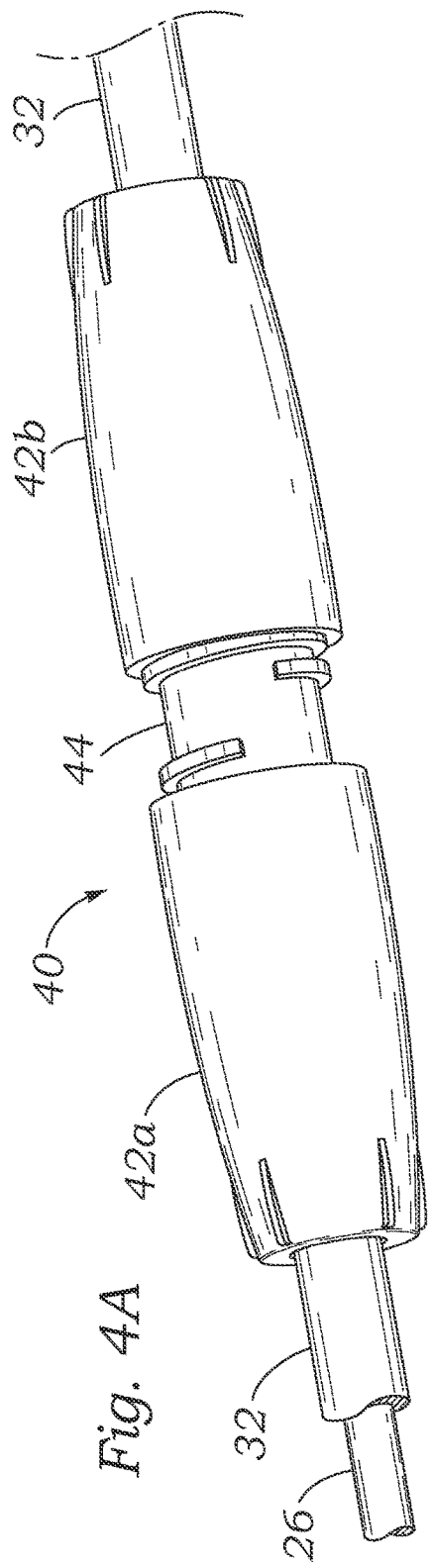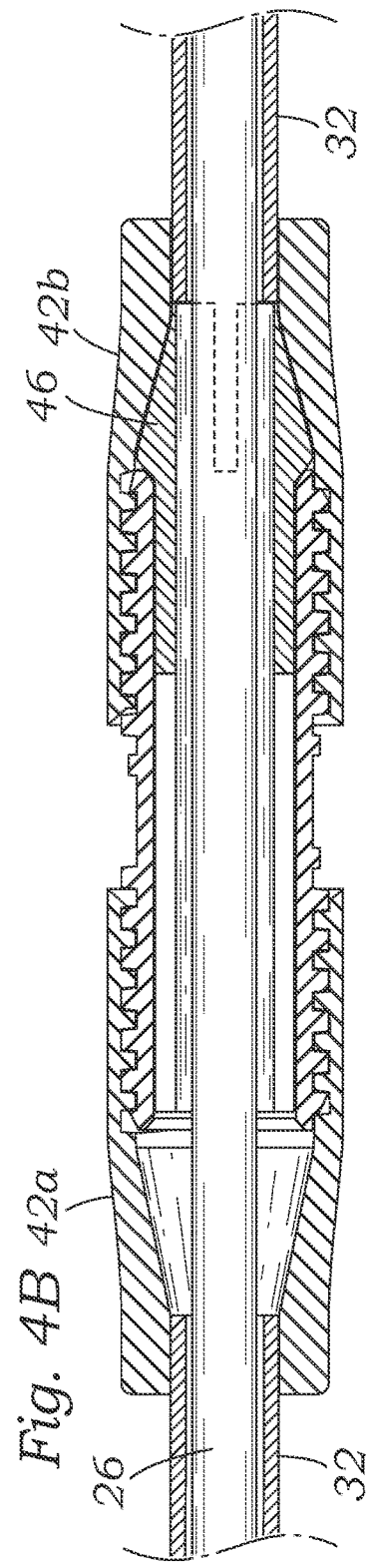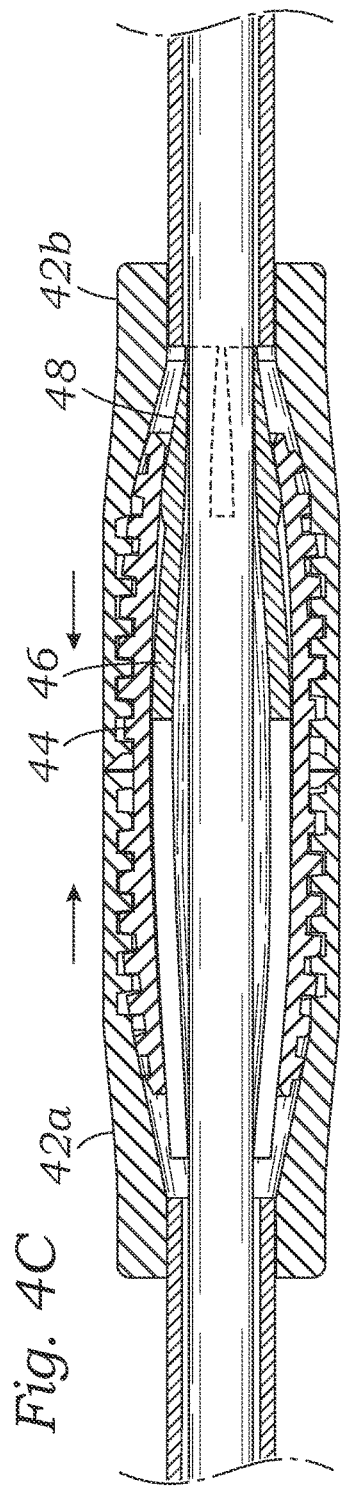

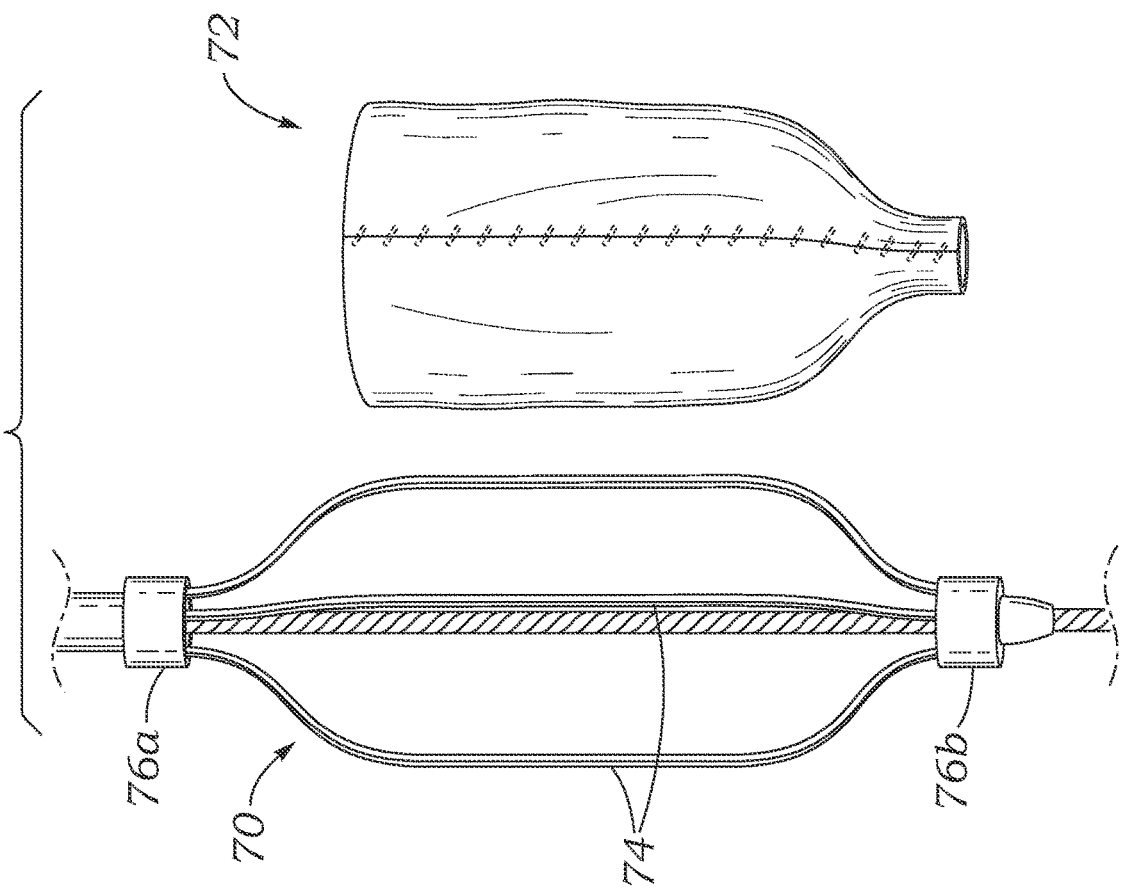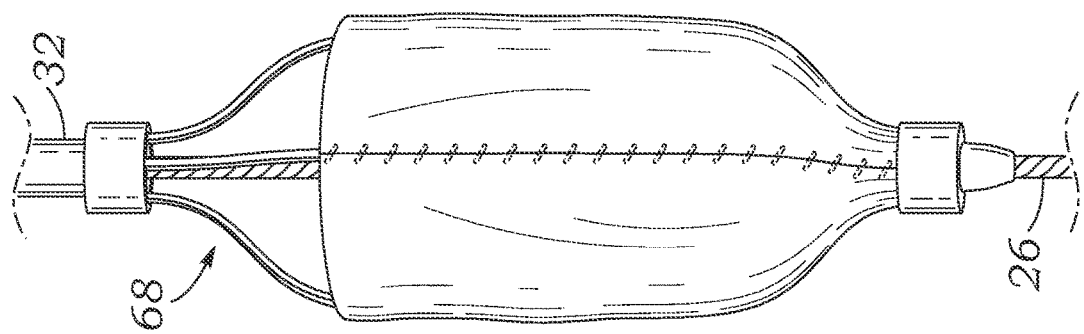

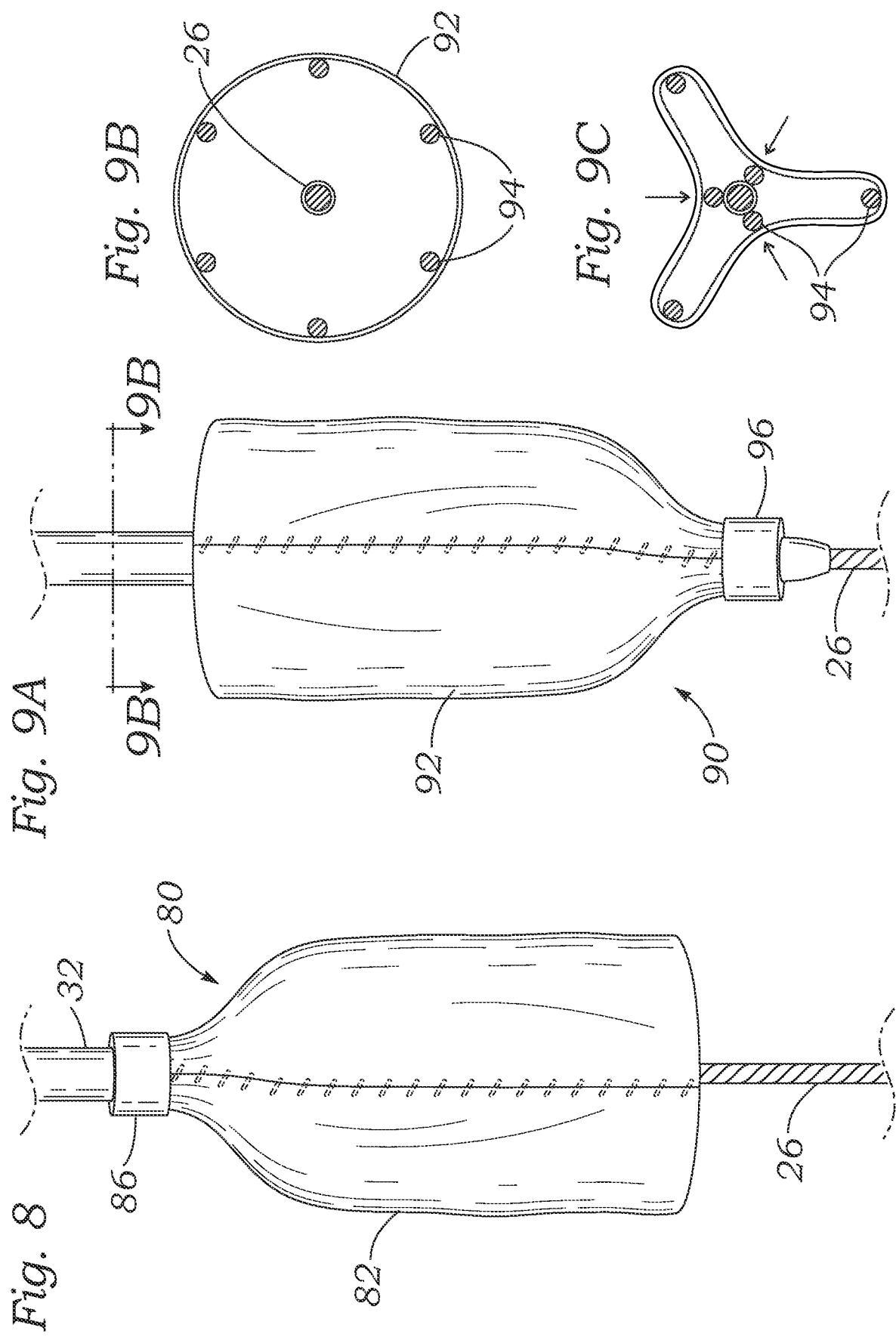

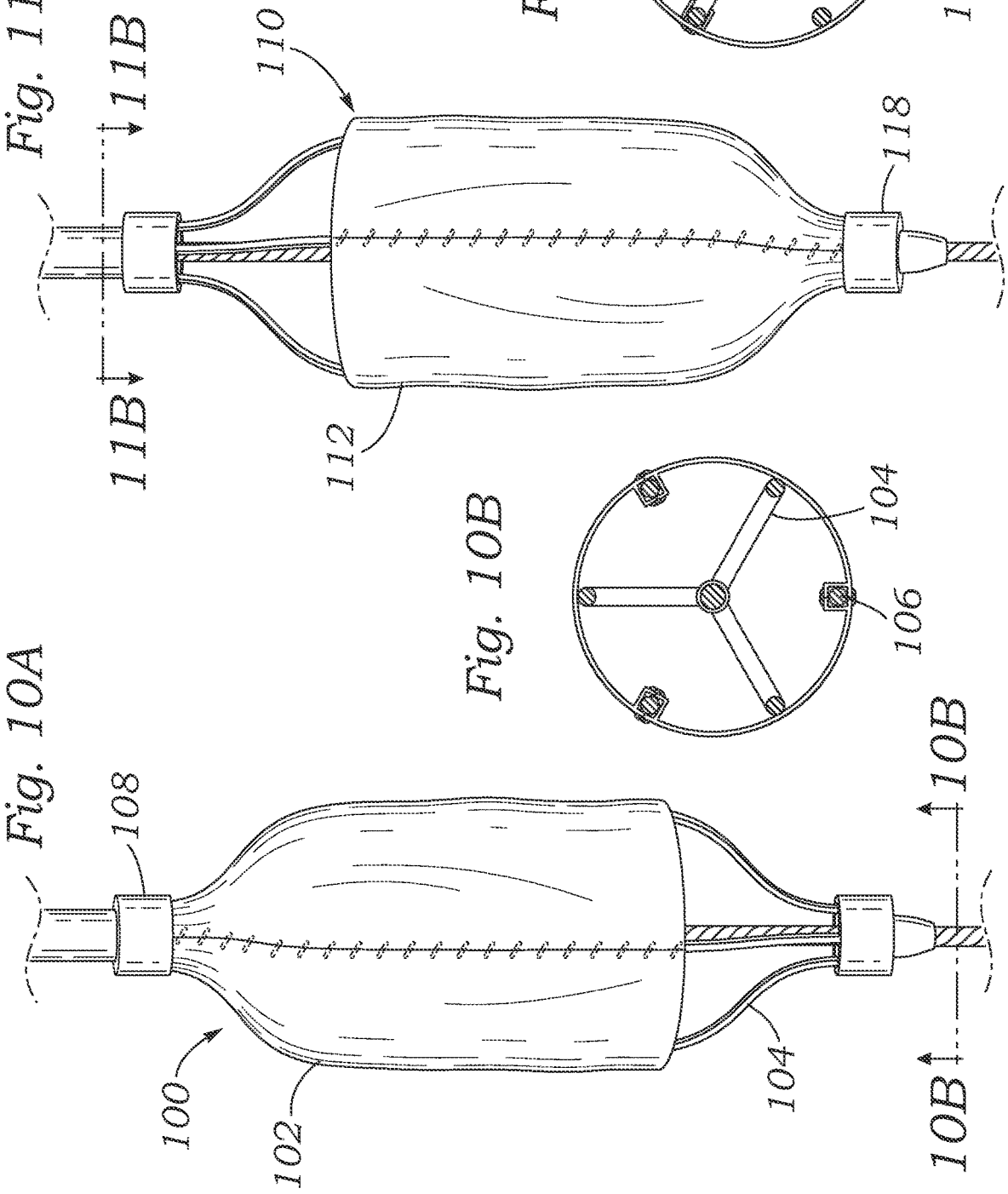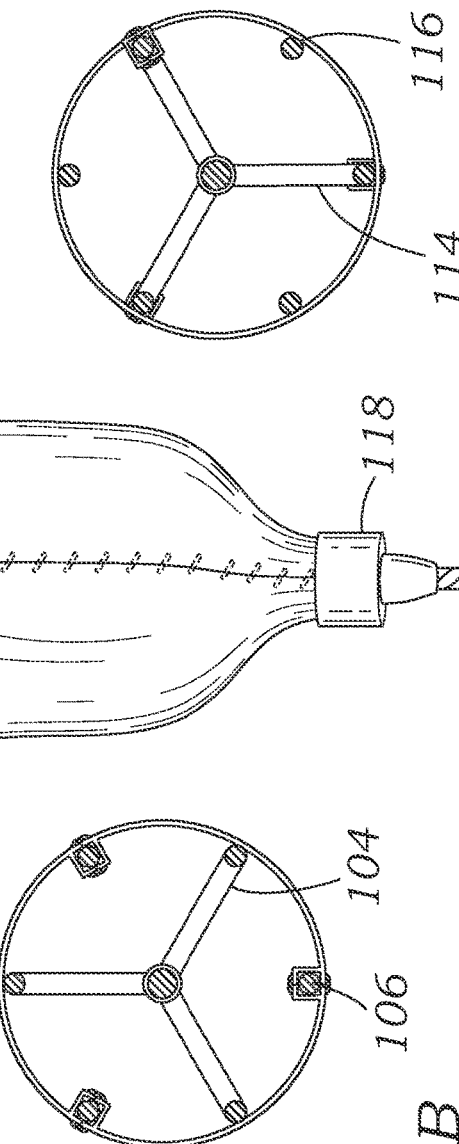

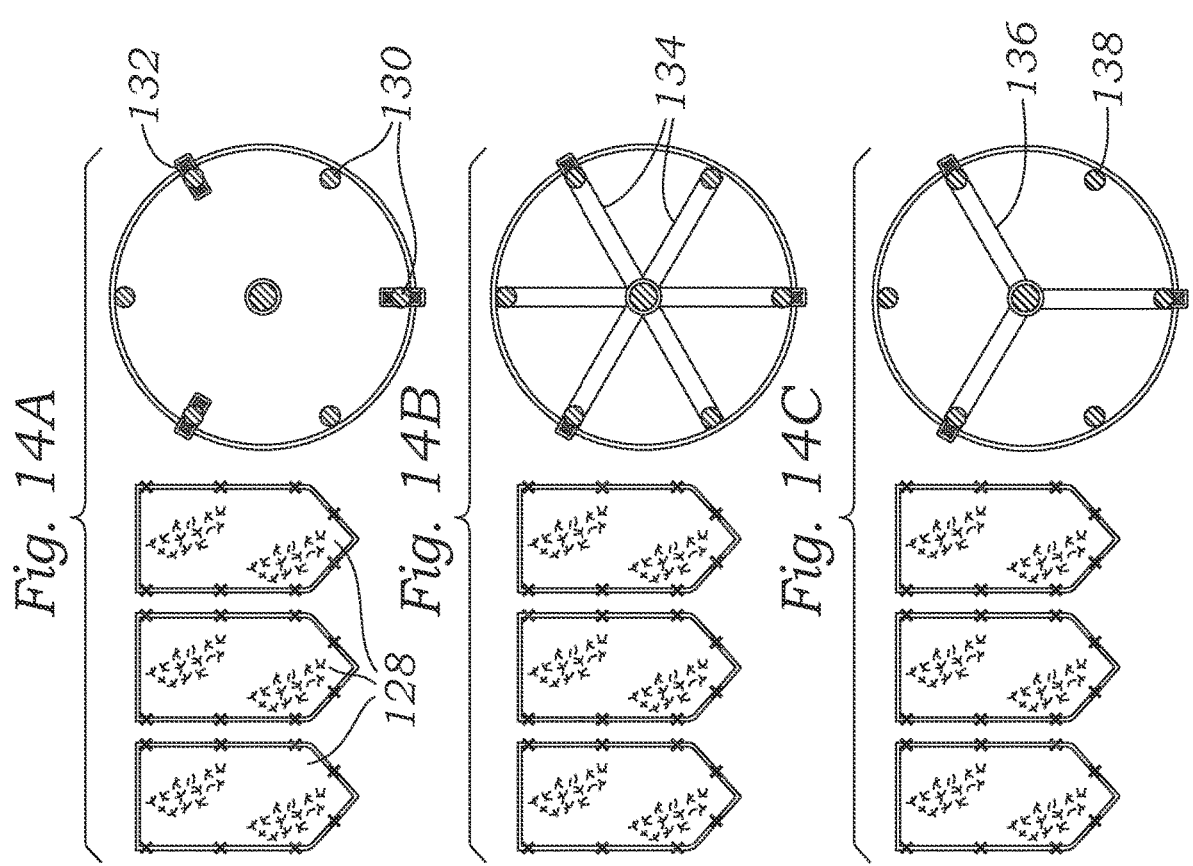

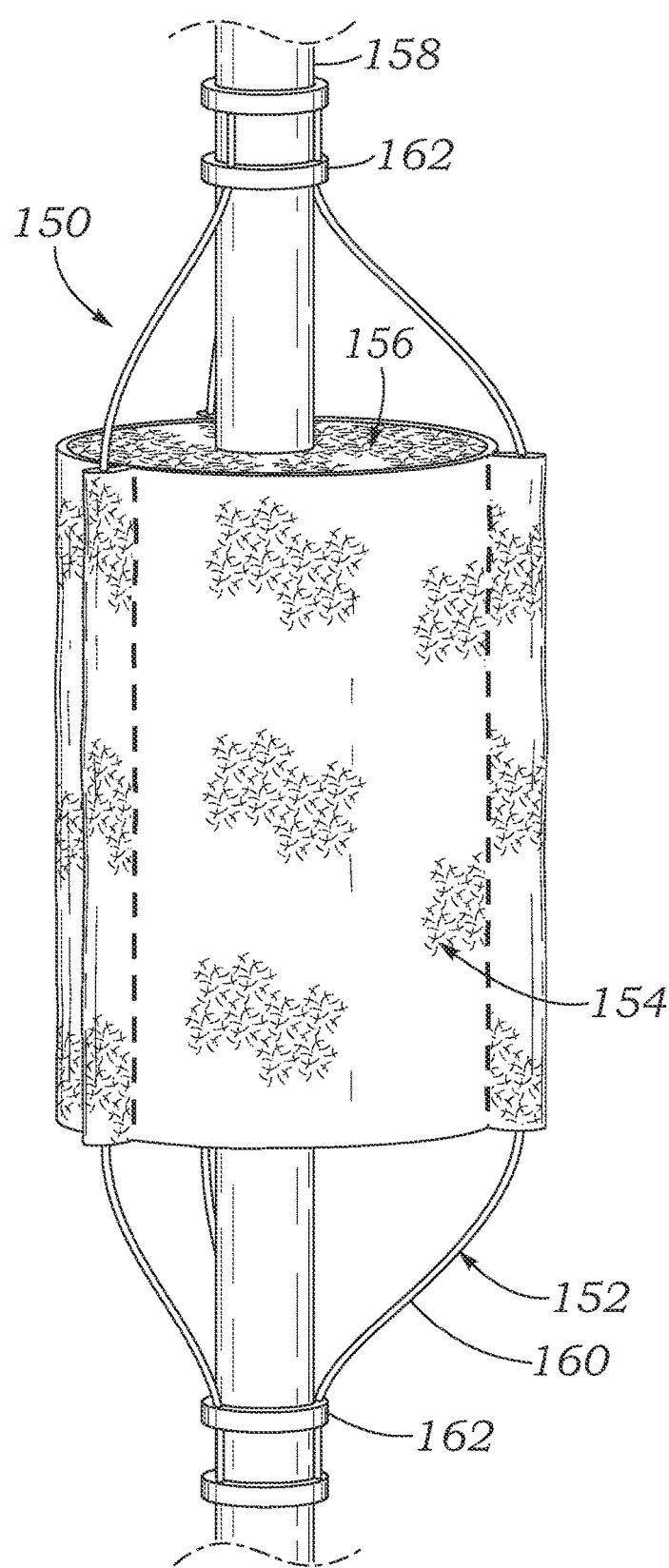
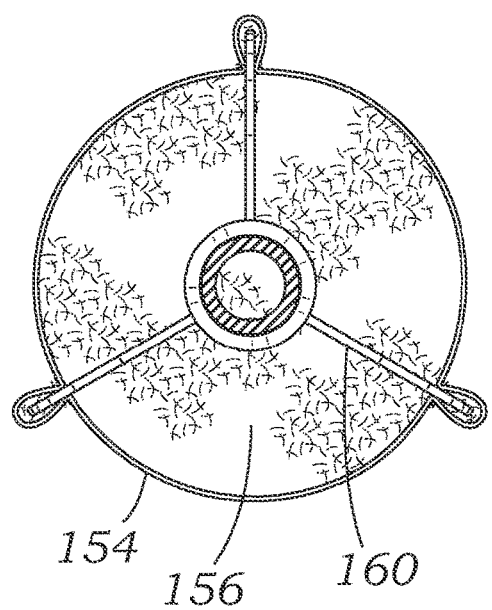
Fig. 17A
Fig. 17B

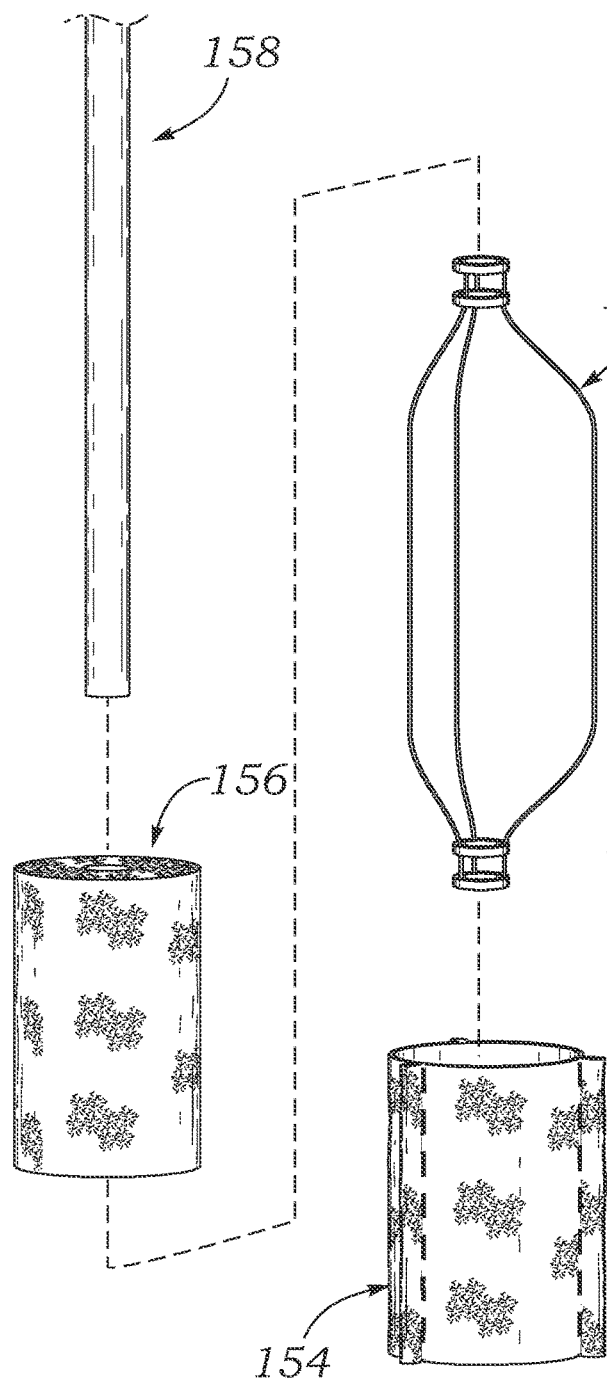
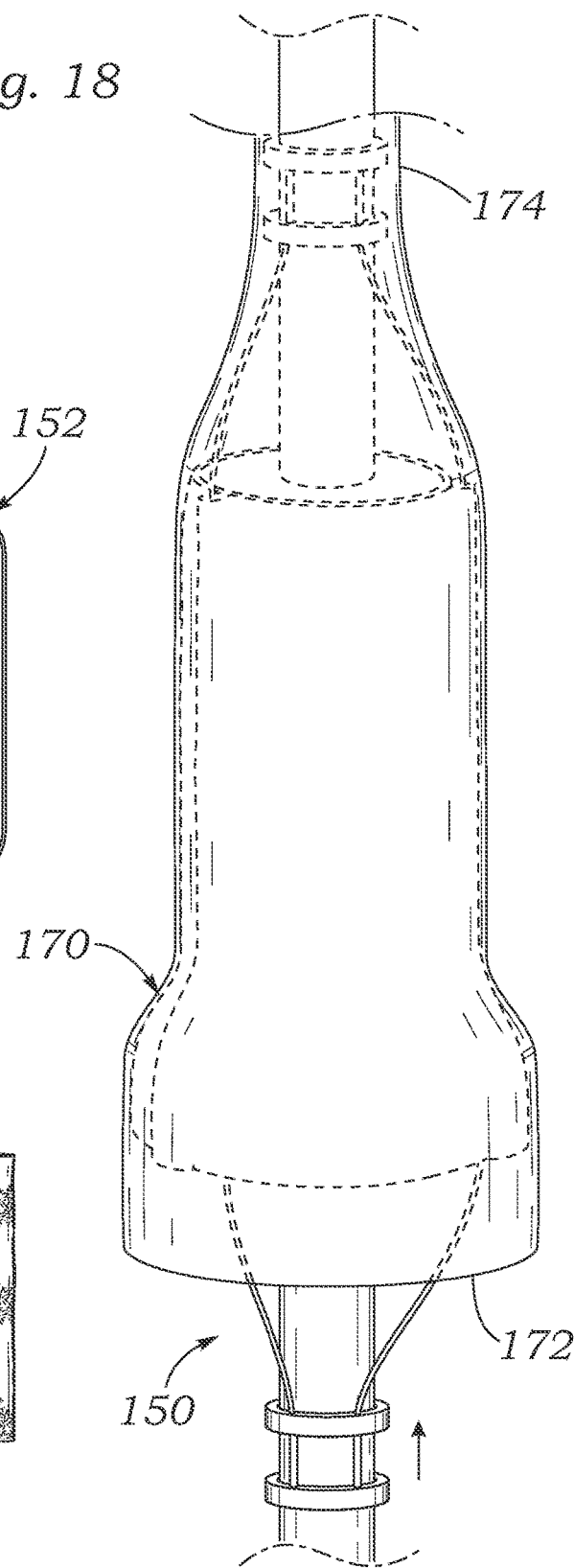

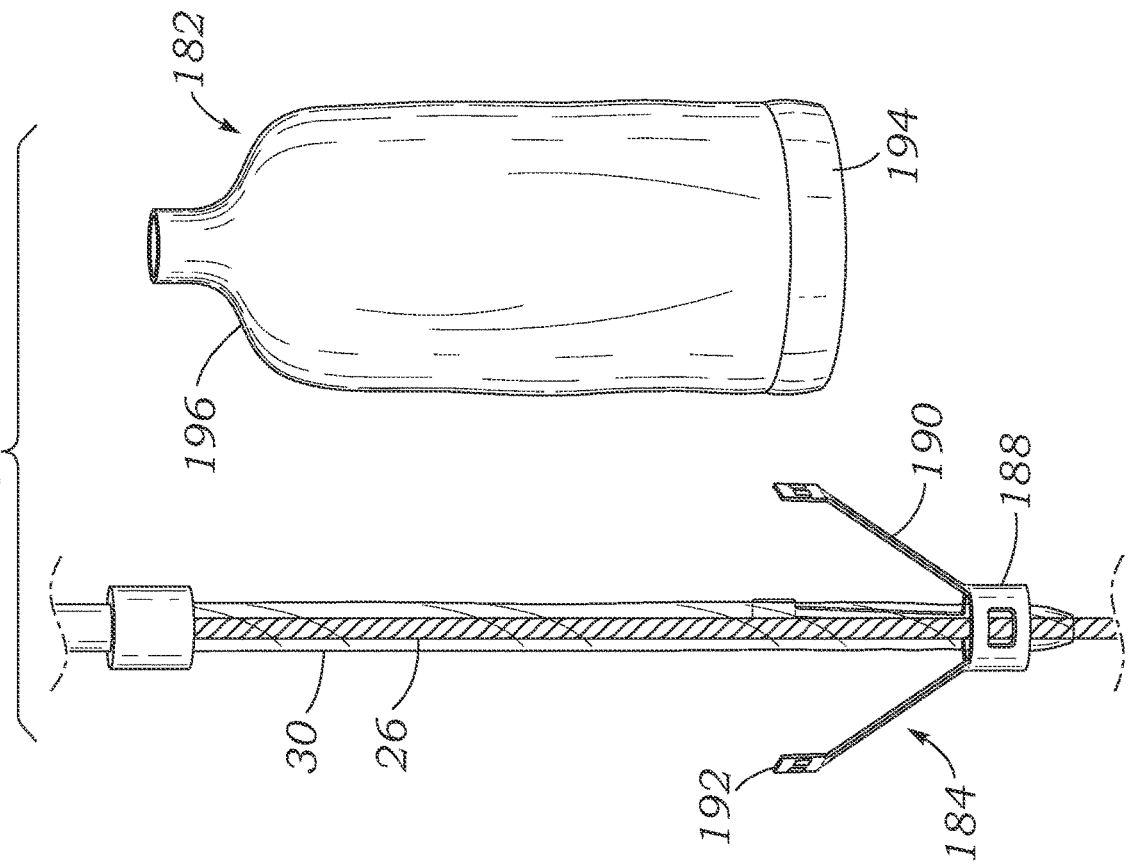
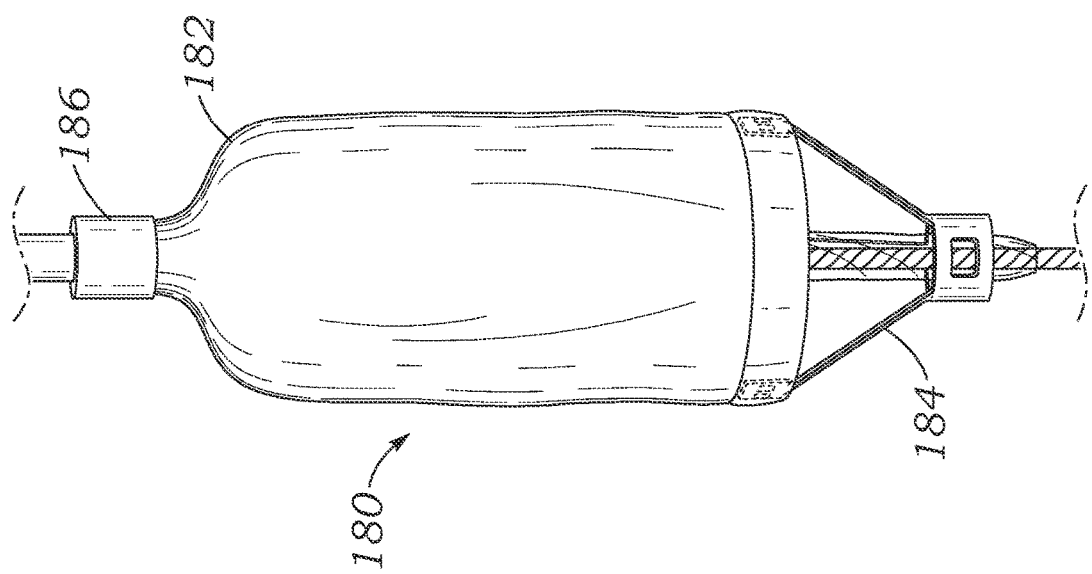

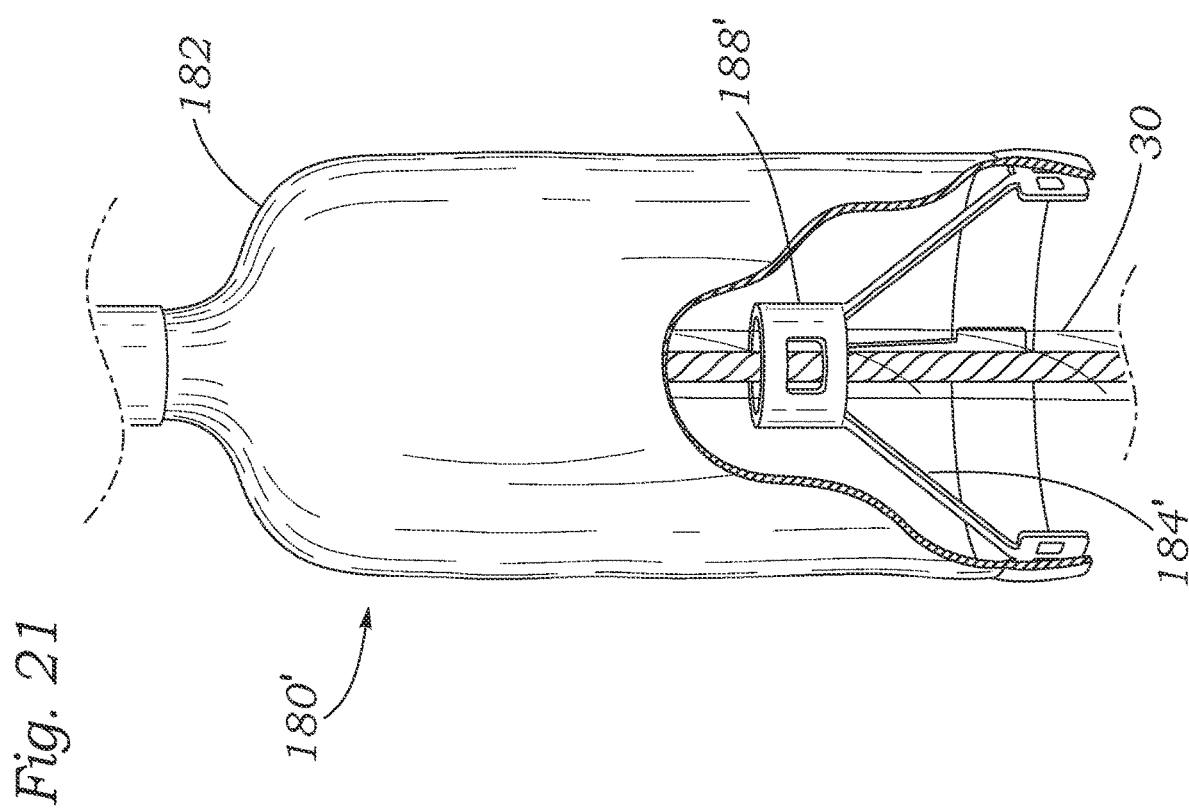

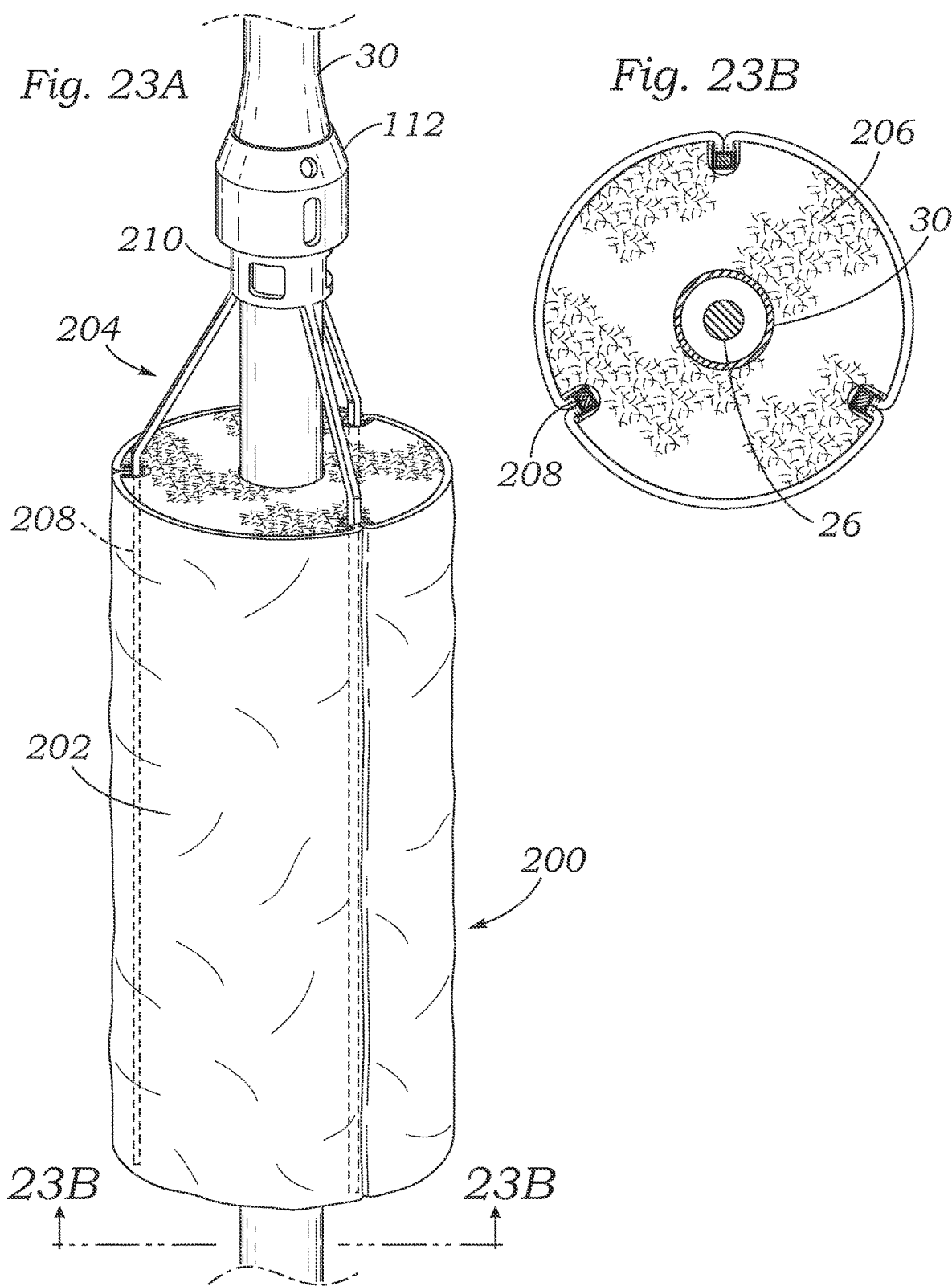

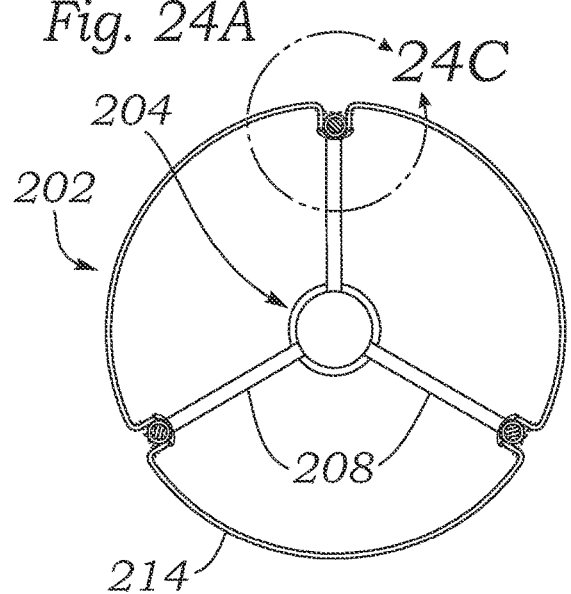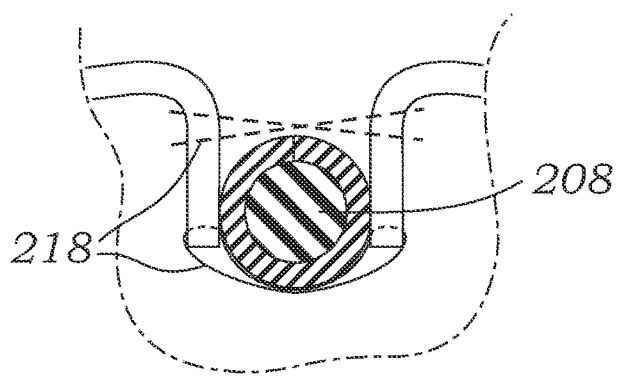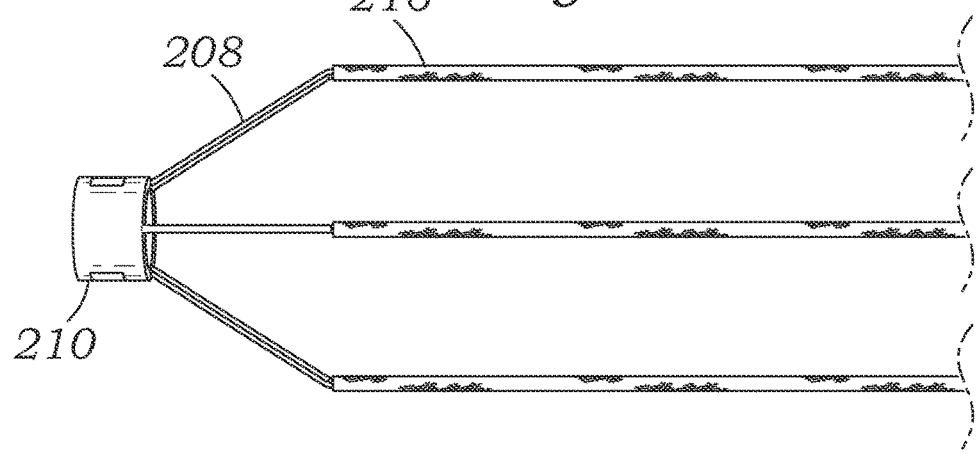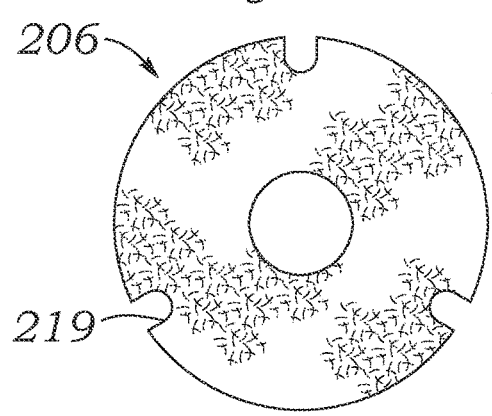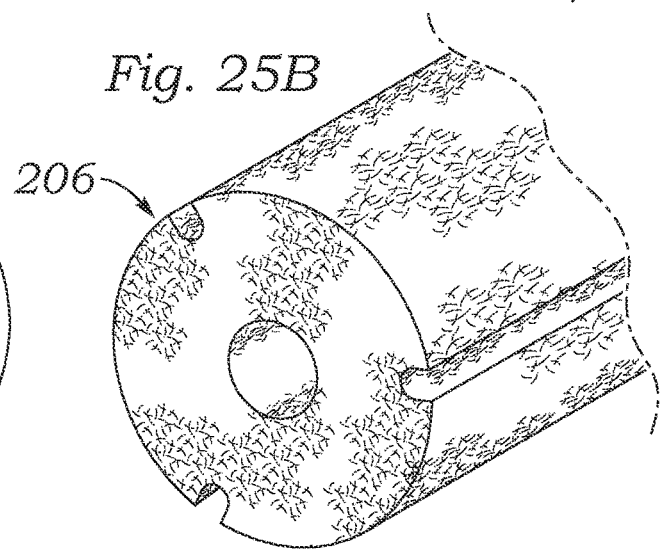

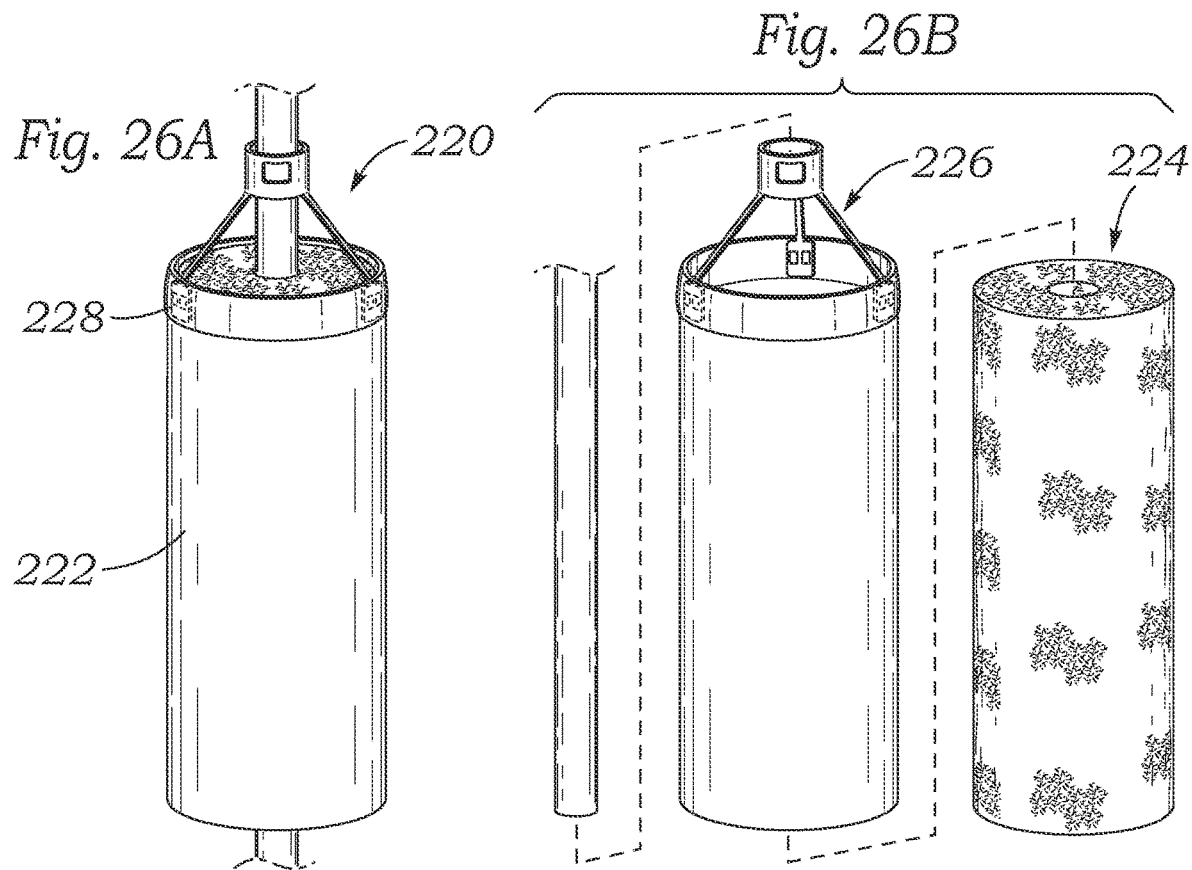
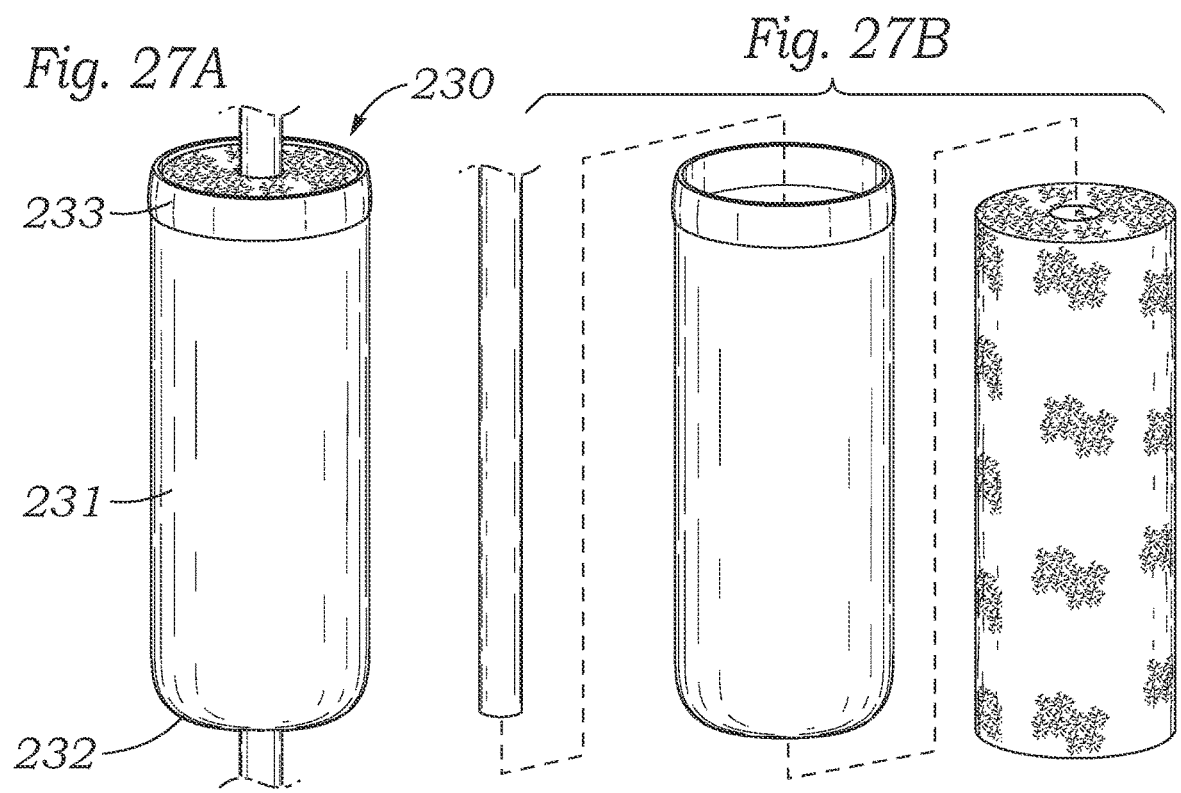

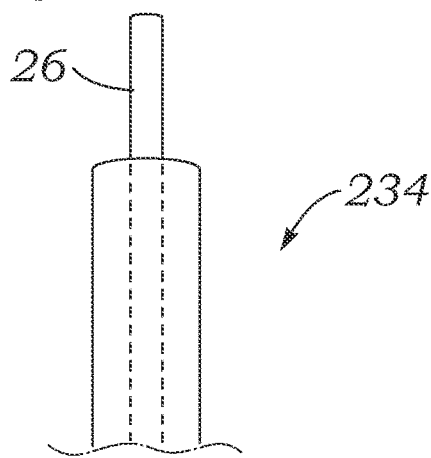
Fig. 28
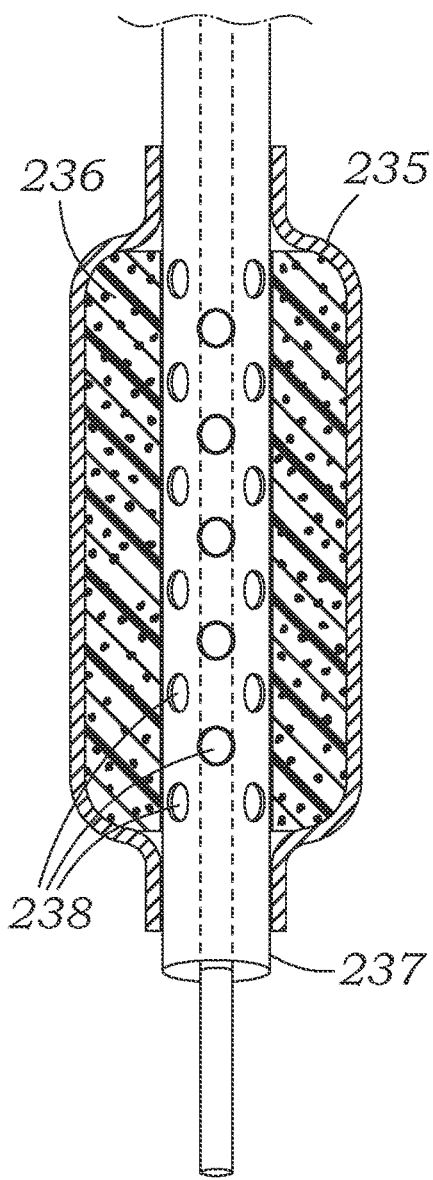
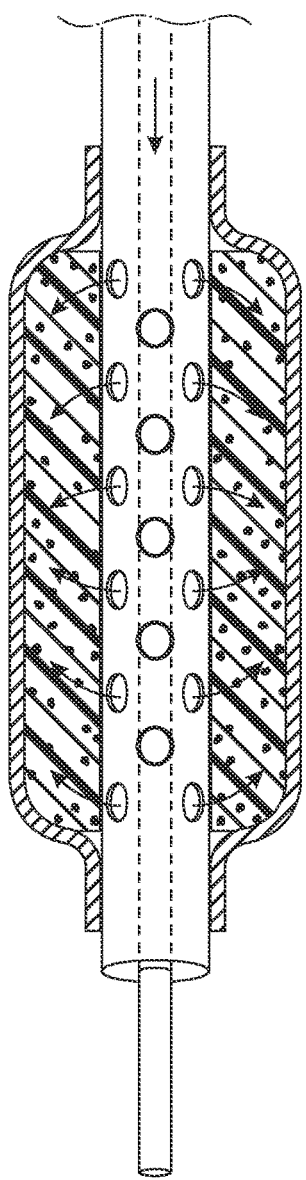
Fig. 29A
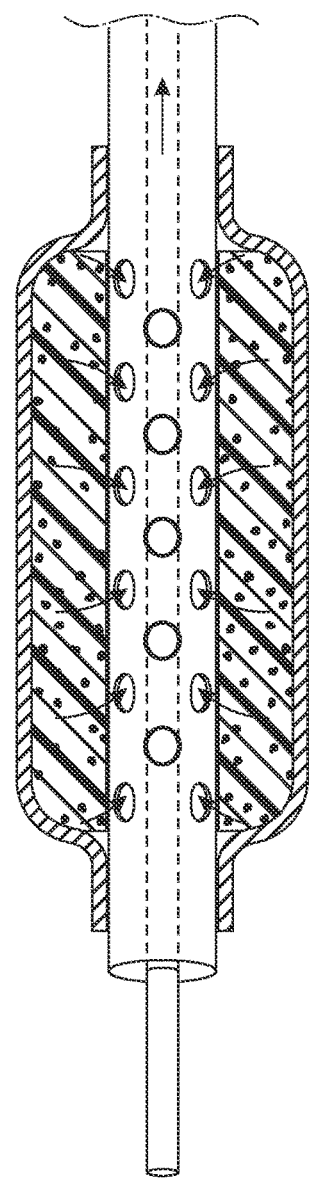
Fig. 29B

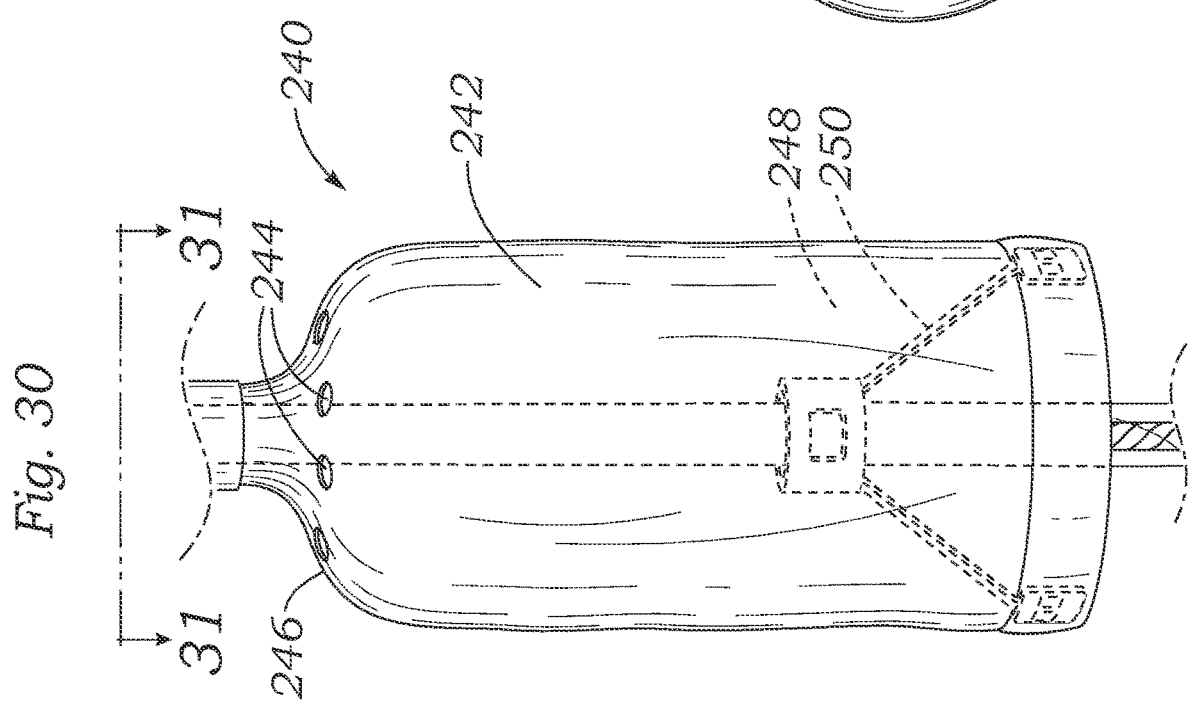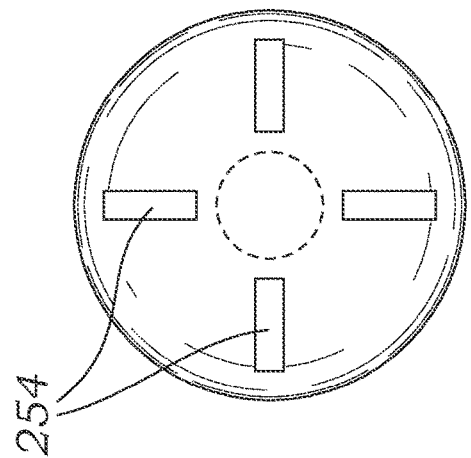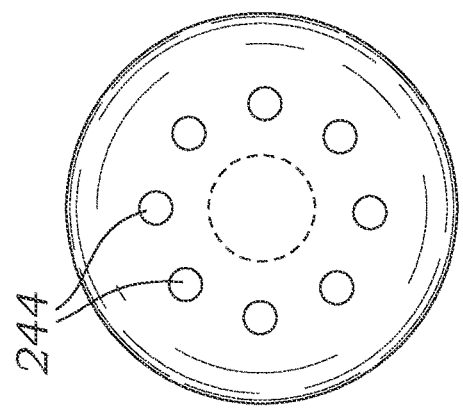

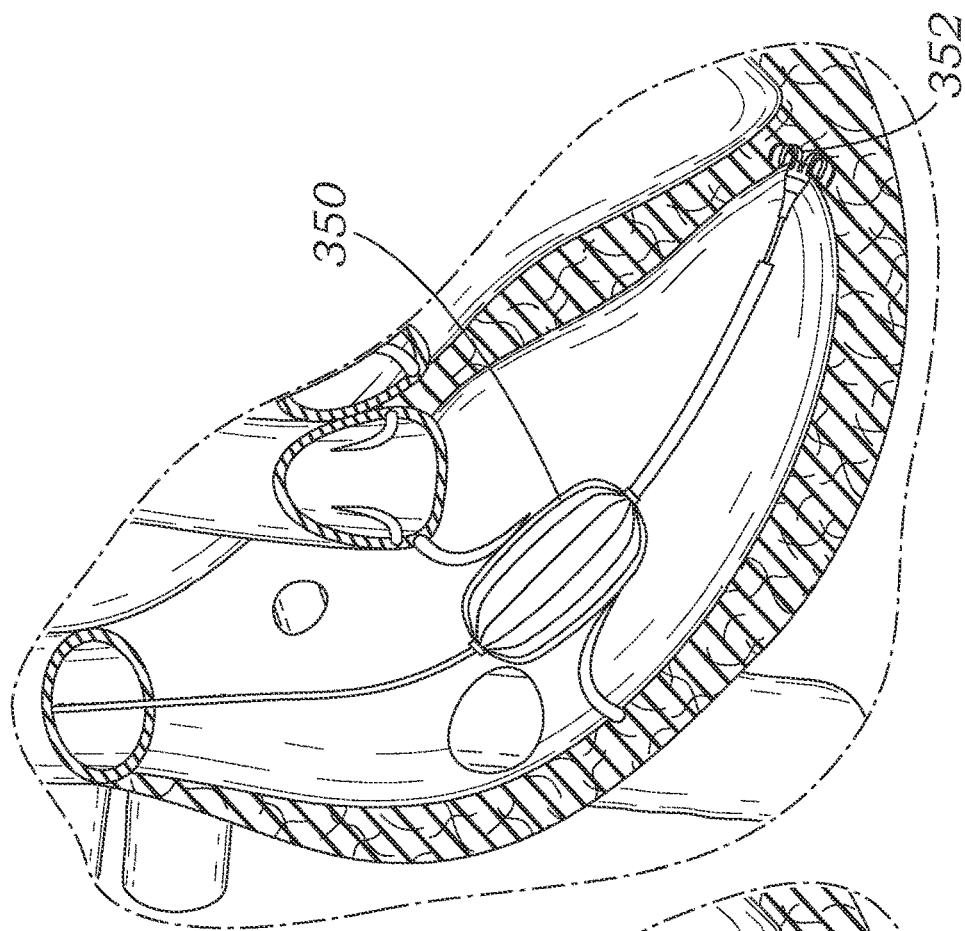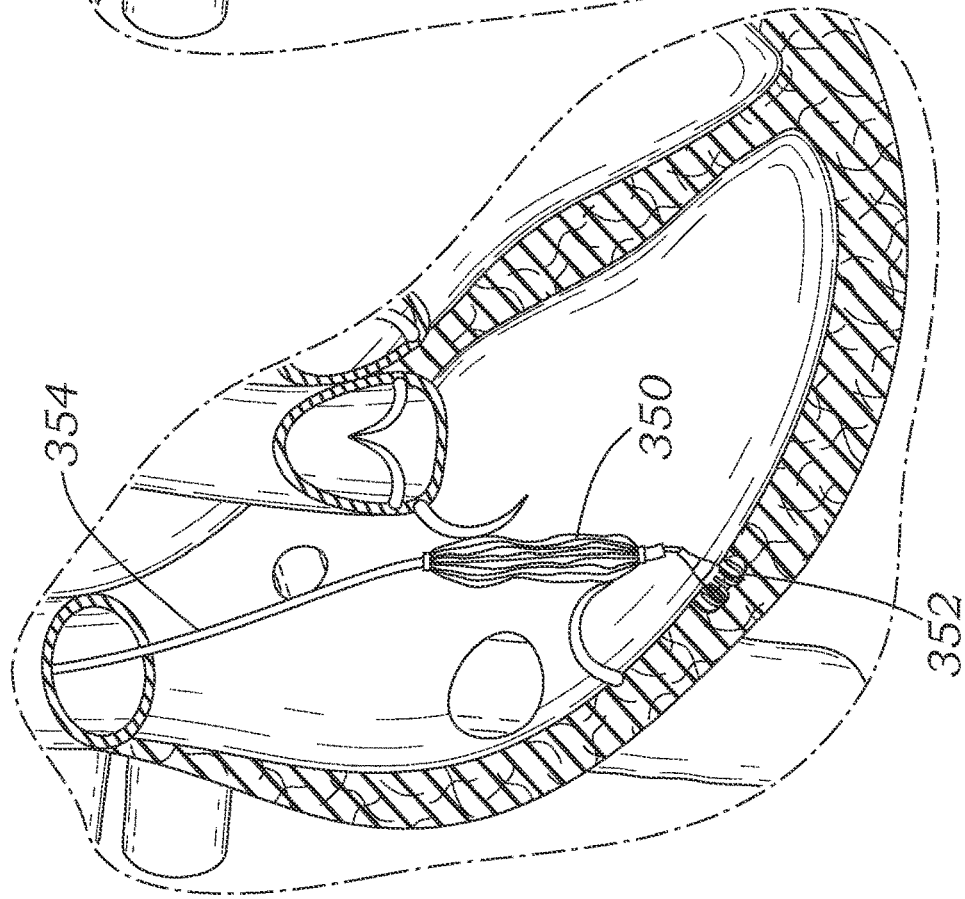

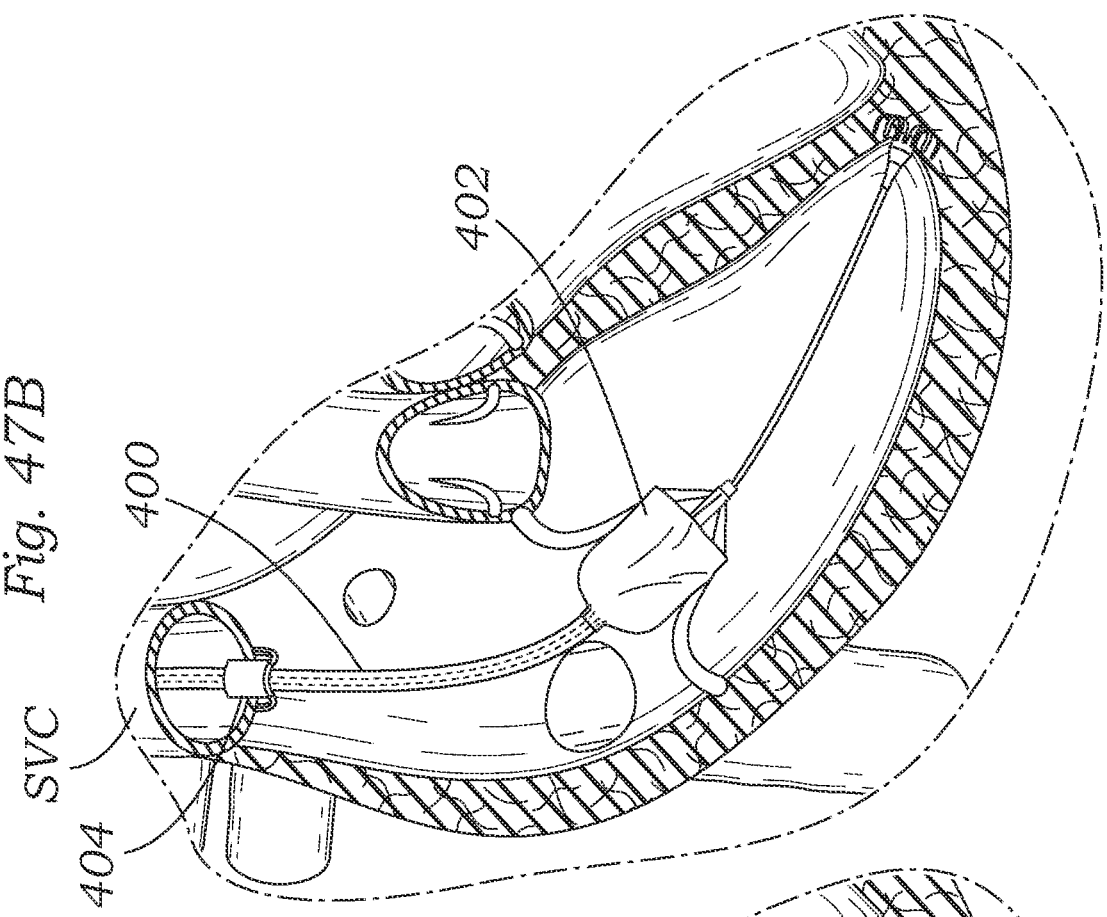
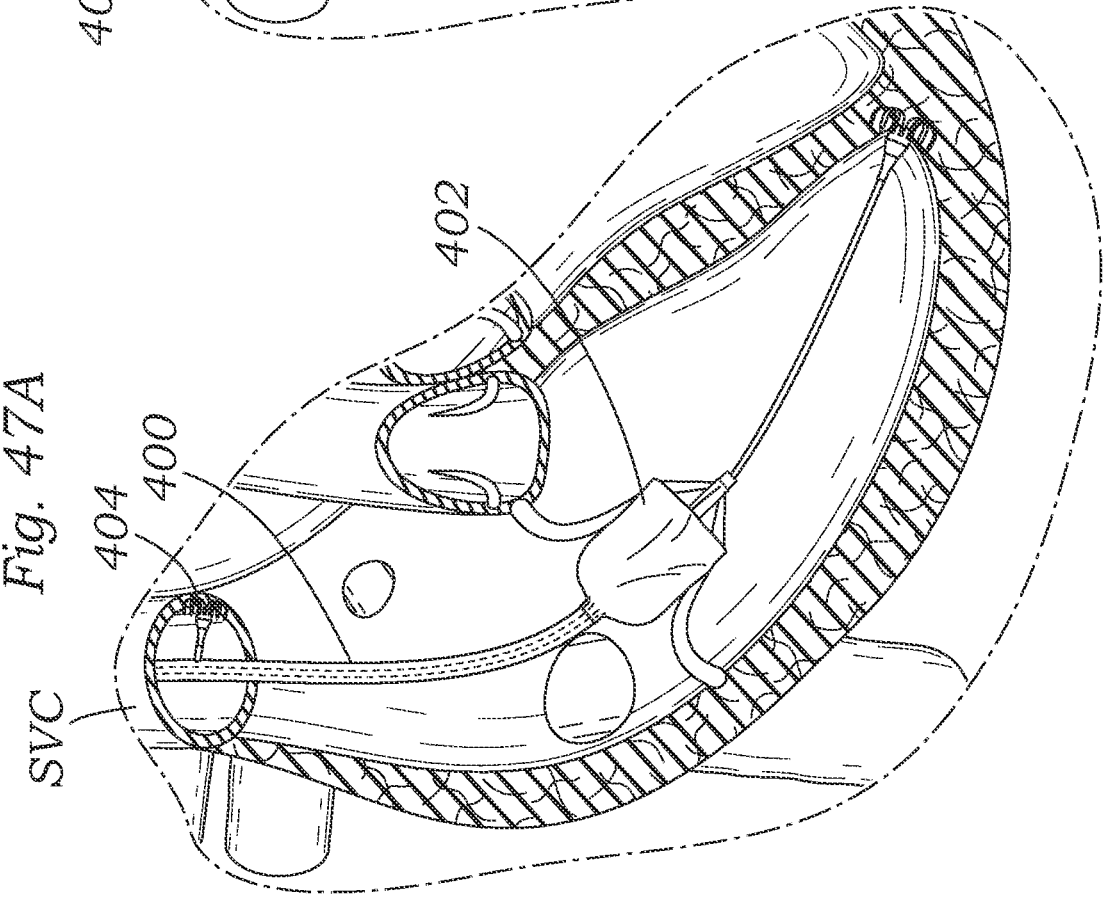

US 11,944,538 B2

METHODS FOR REDUCING CARDIAC VALVE REGURGITATION

RELATED APPLICATIONS

The present application is a continuation of U.S. application Ser. No. 16/389,290, filed Apr. 19, 2019, now issued as U.S. Pat. No. 11,285,812, which is a continuation of U.S. application Ser. No. 15/296,887, filed Oct. 18, 2016, now issued as U.S. Pat. No. 10,285,812, which is a continuation of U.S. application Ser. No. 13/895,572, filed May 16, 2013, now issued as U.S. Pat. No. 9,474,605, which claims priority under 35 U.S.C. § 119 to U.S. Provisional Application Ser. No. 61/647,973, filed May 16, 2012, and to U.S. Provisional Application Ser. No. 61/734,728, filed Dec. 7, 2012, the disclosures of which are expressly incorporated herein by reference.

FIELD OF THE INVENTION

The present invention relates generally to devices and methods for improving the function of a defective heart valve. The devices and methods disclosed herein are particularly well adapted for implantation in a patient's heart for reducing regurgitation through a heart valve.

BACKGROUND OF THE INVENTION

The function of the heart may be seriously impaired if any of the heart valves are not functioning properly. The heart valves may lose their ability to close properly due to e.g. dilation of an annulus around the valve, ventricular dilation, or a leaflet being flaccid causing a prolapsing leaflet. The leaflets may also have shrunk due to disease, e.g., rheumatic disease, and thereby leave a gap in the valve between the leaflets. The inability of the heart valve to close properly can cause a leak backwards (i.e., from the outflow to the inflow side), commonly referred to as regurgitation, through the valve. Heart valve regurgitation may seriously impair the function of the heart since more blood will have to be pumped through the regurgitating valve to maintain adequate circulation. Heart valve regurgitation decreases the efficiency of the heart, reduces blood circulation, and adds stress to the heart. In early stages, heart valve regurgitation leaves a person fatigued or short of breath. If left unchecked, the problem can lead to congestive heart failure, arrhythmias or death.

Heart valve disease, such as valve regurgitation, is typically treated by replacing or repairing the diseased valve during open-heart surgery. However, open-heart surgery is highly invasive and is therefore not an option for many patients. For high-risk patients, a less-invasive method for repair of heart valves is considered generally advantageous.

Accordingly, there is an urgent need for an alternative device and method of use for treating heart valve disease in a minimally invasive procedure that does not require extracorporeal circulation. It is especially desirable that embodiments of such a device and method be capable of reducing or eliminating regurgitation through a tricuspid heart valve. It is also desirable that embodiments of such a device and method be well-suited for treating a mitral valve. It is also desirable that such a device be safe, reliable and easy to deliver. It is also desirable that embodiments of such a device and method be applicable for improving heart valve function for a wide variety of heart valve defects. It is also desirable that embodiments of such a device and method be capable of improving valve function without replacing the native valve. The present invention addresses this need.

SUMMARY OF THE INVENTION

The present invention relates generally to devices and methods for improving the function of a defective heart valve. The devices and methods disclosed herein are particularly well adapted for implantation in a patient's heart for reducing regurgitation through a heart valve. The devices and methods disclosed herein are particularly useful in reducing regurgitation through the two atrioventricular (AV) valves, which are between the atria and the ventricles—i.e., the mitral valve and the tricuspid valve.

In one embodiment, the device comprises: an anchor to deploy in the tissue of the right ventricle, a flexible anchor rail connected to the anchor, a coaptation element that rides over the anchor rail, a catheter attached to the proximal end of the coaptation element, a locking mechanism to fix the position of the coaptation element relative to the anchor rail, and a proximal anchoring feature to fix the proximal end of the coaptation catheter subcutaneously in the subclavian vein.

In another particular embodiment, the coaptation element consists of a hybrid structure: a series of a plurality (preferably three or more) flexible metallic struts to define a mechanical frame structure or a compressible biocompatible material, and a covering of pericardium or some other biocompatible material to provide a coaptation surface around which the native leaflets can form a seal. The flexible struts desirably attach to a catheter shaft on their proximal and/or distal ends, and collapse into a smaller diameter in order to be delivered through a low profile sheath. In particular, the struts attach on one end or both to a catheter shaft, and are complete or interrupted, they typically extend the length of the element, extend out or inwards, and may be discrete struts or a more connected mesh. The mechanical frame typically expands to the larger shape passively upon exiting a protective sheath via shape memory properties (e.g. Nitinol), but could also be expanded via longitudinal compression of the catheter, a shape memory balloon or some other external force. Additionally, the coaptation element can be an open or closed structure, any biocompatible material and framework that allows for compressibility for delivery and expands either actively or passively upon delivery, can be various shapes, and can be a passive or active element that is responsive to the cardiac cycle to change shapes to accommodate the regurgitant orifice.

In accordance with a preferred embodiment, a heart valve coaptation system for reducing regurgitation through the valve comprises a flexible rail having a ventricular anchor on the distal end thereof adapted to anchor into tissue within a ventricle. A delivery catheter has a lumen through which the flexible rail passes, and a coaptation member fixed on a distal end of the delivery catheter has a bell-shaped cover with a first end open and a flexible inner support holding the first end open. Finally, a locking collet on the delivery catheter secures the axial position of the coaptation member and delivery catheter on the flexible rail.

The locking collet preferably includes a pair of internally threaded tubular grips each fixed to one of two separate sections of the delivery catheter and engaging a common externally threaded tubular shaft member. The tubular grips act on a wedge member interposed between at least one of the grips and the flexible rail to securing the axial position of the coaptation member and delivery catheter on the flexible rail. The first end of the bell-shaped cover of the coaptation member may be on a distal or ventricular side thereof, or on the proximal or atrial side. The second end of the bell-shaped cover may have flow through openings to help avoid blood stagnation. The flexible inner support may comprise a flexible frame with struts emanating from a central collar and engaging the first end of the bell-shaped cover, or with struts that extend substantially the length of the bell-shaped cover. Alternatively, the flexible inner support comprises a compressible foam member substantially filling the cover. The cover may formed of polycarbonate urethane, or may be bioprosthetic tissue.

Another exemplary embodiment of a heart valve coaptation system for reducing regurgitation through the valve again includes a flexible rail having a ventricular anchor on the distal end thereof adapted to anchor into tissue within a ventricle, and a delivery catheter having a lumen through which the flexible rail passes. A coaptation member fixed on a distal end of the delivery catheter has a smooth outer cover with a compressible foam inner support. A locking collet is provided on the delivery catheter for securing the axial position of the coaptation member and delivery catheter on the flexible rail. Alternatively, the coaptation member has an outer cover of polycarbonate urethane with a flexible inner support holding the cover outward from the delivery catheter.

In either of the two previous systems, the ventricular anchor may comprises two separate anchors that cooperate to secure the flexible rail of the flexible rail to the ventricle tissue. In one version, the cover is tubular with both ends open, and if not made of polycarbonate urethane the cover is made of bioprosthetic tissue. If the flexible inner support is a compressible foam member it may substantially fill the cover and be an open cell foam that permits blood flow therethrough. The flexible inner support may also comprise a flexible frame with struts that extend substantially the length of the cover between the compressible foam member and the cover. Alternatively, the flexible frame has struts emanating from a central collar and engaging the inside of the cover. In one embodiment, wherein the cover is tubular with both ends open, while in another the cover is bell-shaped with a distal or ventricular side being open and a proximal or atrial side being closed. Alternatively, the cover is bell-shaped with both ends being closed.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures may be drawn to scale for some embodiments, the figures are not necessarily drawn to scale for all embodiments. Embodiments of the present disclosure will be described and explained with additional specificity and detail through the use of the accompanying drawings.

FIGS. 3A and 3B are sectional views of the right atrium and ventricle that illustrate deployment of a regurgitation reduction device including a delivery catheter advanced along an anchor rail to position a coapting element within the tricuspid valve;

FIGS. 4A-4C are perspective and longitudinal sectional views of a locking collet shown proximally positioned on the catheter of FIGS. 3A and 3B that is used to fix the position of the delivery catheter and coapting element relative to the anchor rail;

FIGS. 7A and 7B are assembled and exploded elevational views of another coapting element having an inner strut frame and tissue partially covering a ventricular end of the coapting element;

FIG. 8 is an assembled elevational view of a still further coapting element having a tissue cover on the atrial end and cantilevered struts extending from the atrial end within the tissue cover;

FIGS. 9A-9C are assembled elevational and atrial end views of another coapting element with a tissue cover and cantilevered struts extending from the ventricular end thereof;

FIGS. 10A-10B are assembled elevational and ventricle end views of a coapting element having an atrial end tissue cover and an inner strut configuration with some struts extending the full length of the coapting element and some cantilevered from the atrial end;

FIGS. 11A-11B are views of a coapting element much like that shown in FIGS. 10A-10B but with the tissue cover and struts extending from the ventricular end;

FIGS. 14A-14C are schematic views of various constructions of three-strut/three-panel coapting elements disclosed herein;

FIG. 15 is a schematic view of the construction of a two-strut/two-panel coapting element;

FIG. 16 is a schematic diagram of a representative coapting element and a pair of native tissue leaflets indicating certain key dimensions used in constructing the coapting element;

FIGS. 17A-17C are assembled and exploded views of a coapting element having a three-strut frame, a tubular tissue or other materials covering, and an inner compressible biocompatible material such as a foam;

FIG. 18 is an elevational view of the coapting element of FIGS. 17A-17C being inserted through a constrictor sleeve used for reducing the diameter of the coapting element during delivery into the body;

FIGS. 19 and 20 are assembled and exploded views, respectively, of an alternative coapting element comprising a bell-shaped polymer member held open at one end via a multi-strut frame;

FIG. 21 is a partial cutaway perspective view of a coapting element similar to that shown in FIG. 19, but having a multi-strut frame which is positioned within the bell-shaped polymer member;

FIG. 23A is a perspective view of another coapting element of the present application wherein an outer biocompatible tubular cover mounts to an internal multiple strut frame and encloses a compressible member such as foam therein, and FIG. 23B is an end view thereof;

FIGS. 24A-24C and 25A-25B illustrate a number of components that comprise the coapting element of FIG. 23A;

FIGS. 26A and 26B are assembled and exploded views of a still further coapting element of the present application having an outer tubular cover surrounding a porous compressible member;

FIGS. 27A and 27B are assembled and exploded views of a coapting element similar to that in FIGS. 26 and 27 but wherein a ventricular end of the outer cover is closed;

FIG. 28 is an assembled view of a coapting element with an outer cover surrounding an inner compressible member and with a perforated inner catheter for removing air from the compressible member, shown, respectively, in FIGS. 29A and 29B;

FIG. 30 is a perspective view of a coapting element having an outer bell-shaped cover with a plurality of flow through holes on an otherwise closed atrial end, and FIGS. 31A and 31B show alternative hole patterns;

FIG. 39 is a partial sectional view of an alternative anchoring device having concentric corkscrew anchors, while

FIGS. 42A and 42B show operation of a centering balloon that helps ensure proper positioning of an anchoring member at the apex of the right ventricle;

FIGS. 47A and 47B show two ways to anchor the delivery catheter to the superior vena cava for stabilizing the coapting element;

DETAILED DESCRIPTION OF THE PREFERRED EMBODIMENTS

The following description refers to the accompanying drawings, which illustrate specific embodiments of the invention. Other embodiments having different structures and operation do not depart from the scope of the present invention.

Exemplary embodiments of the present disclosure are directed to devices and methods for improving the function of a defective heart valve. It should be noted that various embodiments of coapting elements and systems for delivery and implant are disclosed herein, and any combination of these options may be made unless specifically excluded. For example, any of the coapting elements disclosed may be combined with any of the flexible rail anchors, even if not explicitly described. Likewise, the different constructions of coapting elements may be mixed and matched, such as combining any tissue cover with any inner flexible support, even if not explicitly disclosed. In short, individual components of the disclosed systems may be combined unless mutually exclusive or otherwise physically impossible.

Figure 1A:
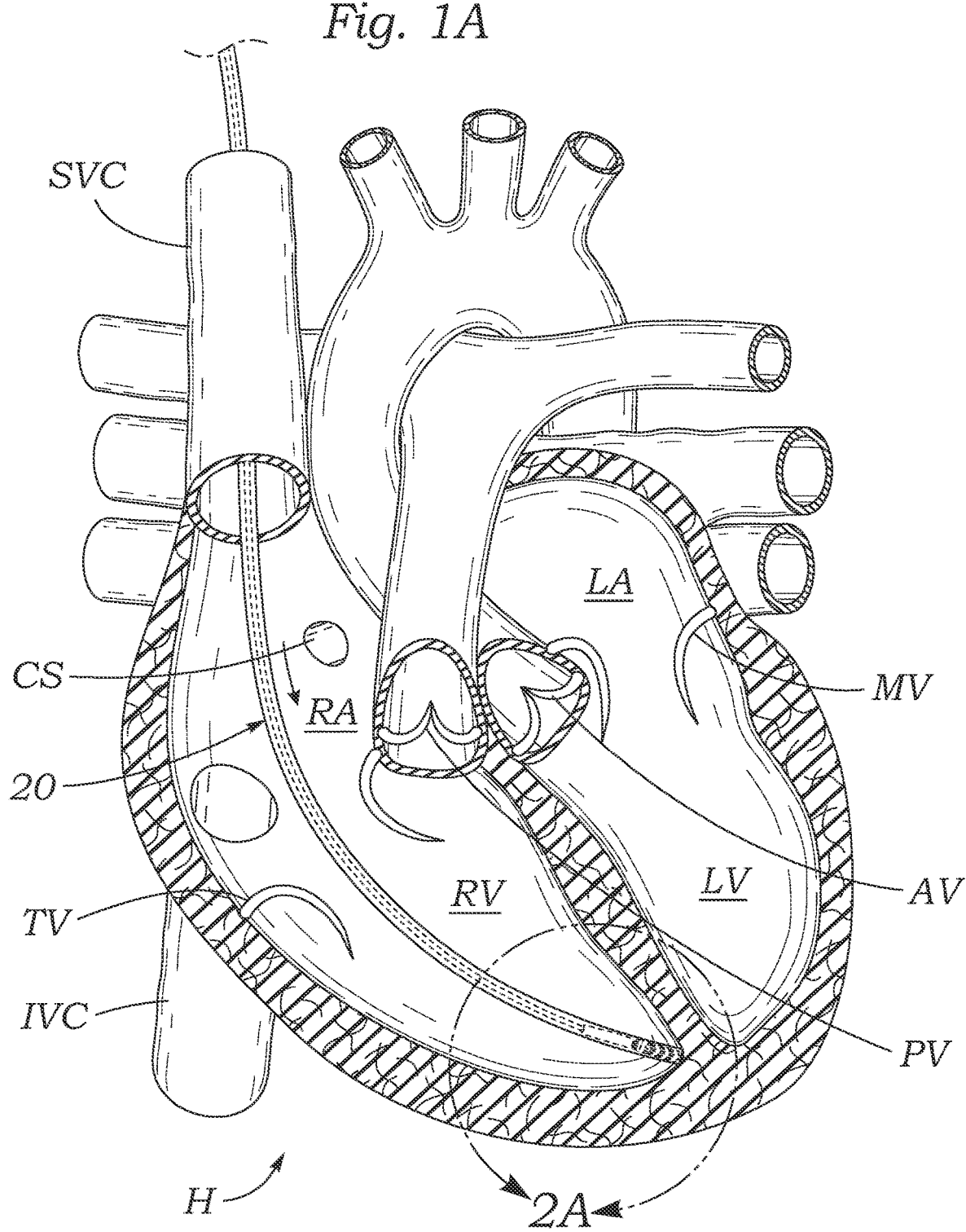
FIG. 1A is a cutaway view of the human heart in a diastolic phase showing introduction of an anchoring catheter into the right ventricle as a first step in deploying a device of the present application for reducing tricuspid valve regurgitation.
Figure 1B:
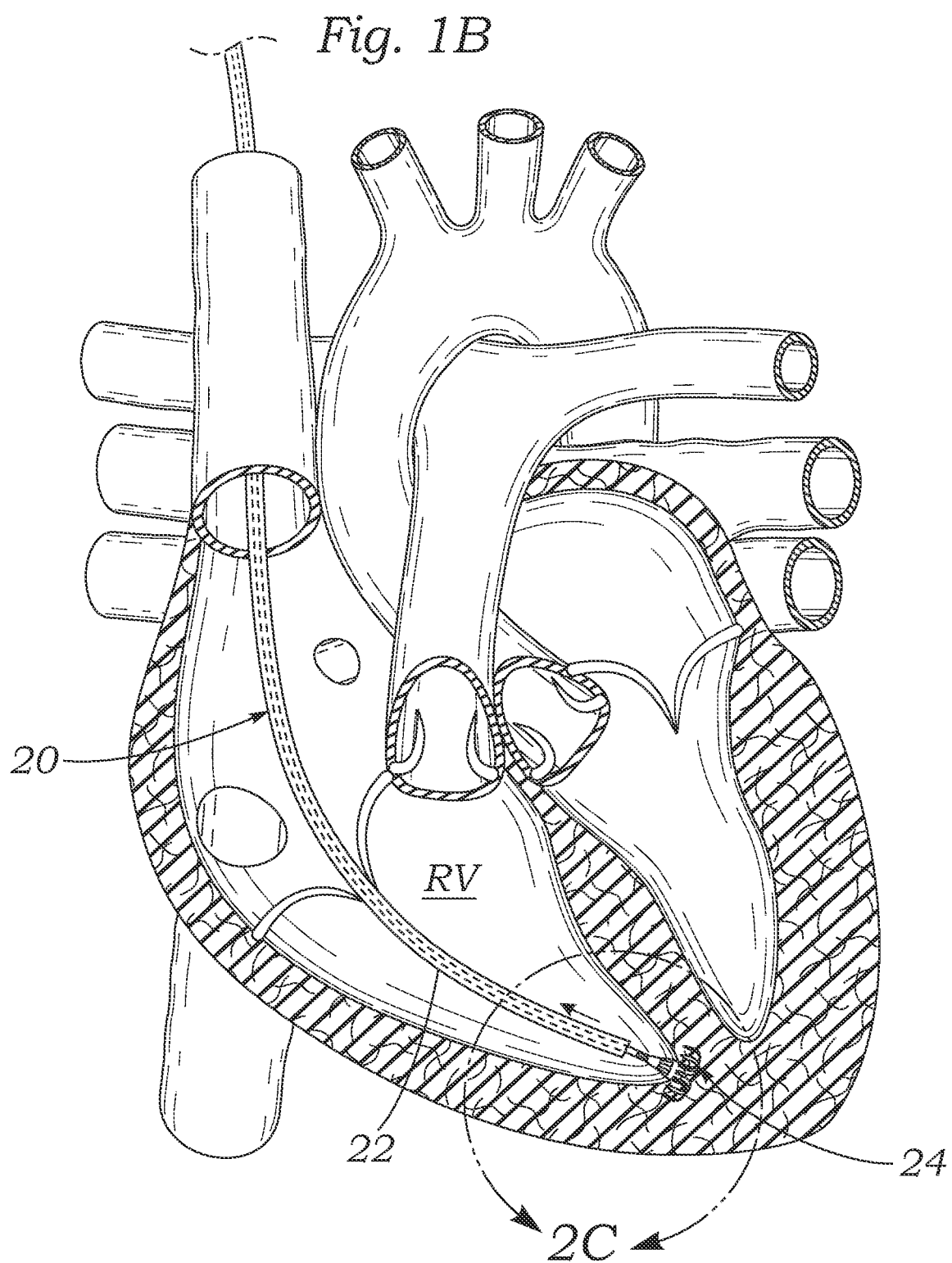
FIG. 1B is a cutaway view of the human heart in a systolic phase showing retraction of the anchoring catheter after installing a device anchor at the apex of the right ventricle.

FIGS. 1A and 1B are cutaway views of the human heart in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta (not identified) and the pulmonary valve PV separates the right ventricle from the pulmonary artery (also not identified). Each of these valves has flexible leaflets extending inward across the respective orifices that come together or "coapt" in the flowstream to form the one-way fluid occluding surfaces. The regurgitation reduction devices of the present application are primarily intended for use to treat the atrioventricular valves, and in particular the tricuspid valve. Therefore, anatomical structures of the right atrium RA and right ventricle RV will be explained in greater detail, though it should be understood that the devices described herein may equally be used to treat the mitral valve MV.

The right atrium RA receives deoxygenated blood from the venous system through the superior vena cava SVC and the inferior vena cava IVC, the former entering the right atrium above, and the latter from below. The coronary sinus CS is a collection of veins joined together to form a large vessel that collects deoxygenated blood from the heart muscle (myocardium), and delivers it to the right atrium RA. During the diastolic phase, or diastole, seen in FIG. 1A, the venous blood that collects in the right atrium RA is pulled through the tricuspid valve TV by expansion of the right ventricle RV. In the systolic phase, or systole, seen in FIG. 1B, the right ventricle RV collapses to force the venous blood through the pulmonary valve PV and pulmonary artery into the lungs. During systole, the leaflets of the tricuspid valve TV close to prevent the venous blood from regurgitating back into the right atrium RA. It is during systole that regurgitation through the tricuspid valve TV becomes an issue, and the devices of the present application are beneficial.

Regurgitation Reduction System:

FIGS. 1A and 1B show introduction of an anchoring catheter 20 into the right ventricle as a first step in deploying a device of the present application for reducing tricuspid valve regurgitation. The anchoring catheter 20 enters the right atrium RA from the superior vena cava SVC after having been introduced to the subclavian vein (see FIG. 5) using well-known methods, such as the Seldinger technique. More particularly, the anchoring catheter 20 preferably tracks over a pre-installed guide wire (not shown) that has been inserted into the subclavian vein and steered through the vasculature until it resides at the apex of the right ventricle. The physician advances the anchoring catheter 20 along the guide wire until its distal tip is touching the ventricular apex, as seen in FIG. 1A.

FIG. 1B shows retraction of a sheath 22 of the anchoring catheter 20 after installing a device anchor 24 at the apex of the right ventricle RV. The sheath 22 has desirably been removed completely from the patient's body in favor of the second catheter, described below.

Figure 2A:
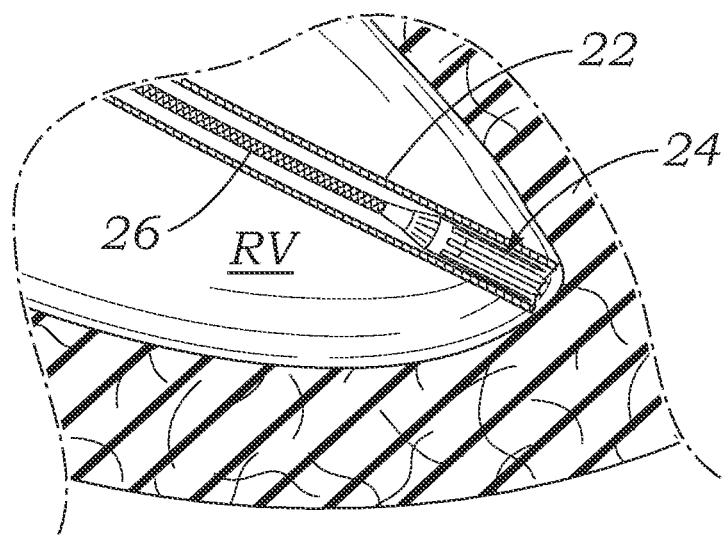
FIGS. 2A-2C are detailed views of installation of an exemplary device anchor by the anchoring catheter.
Figure 2B:
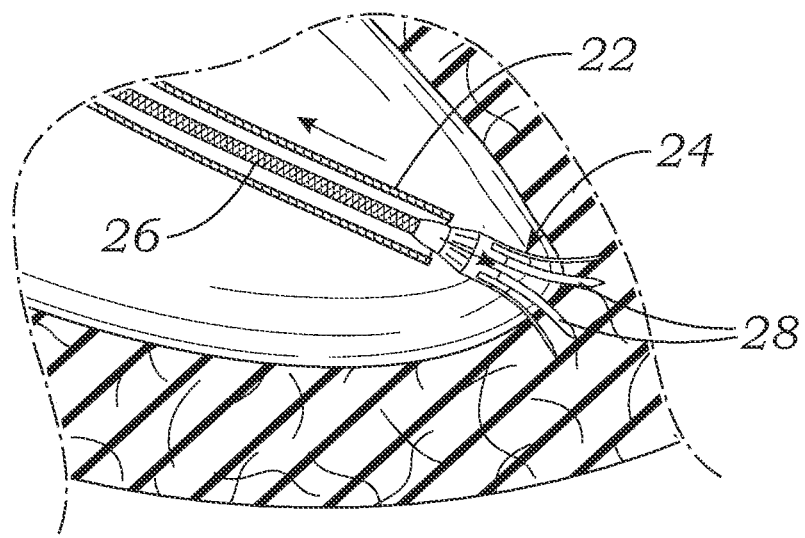
Figure 2C:
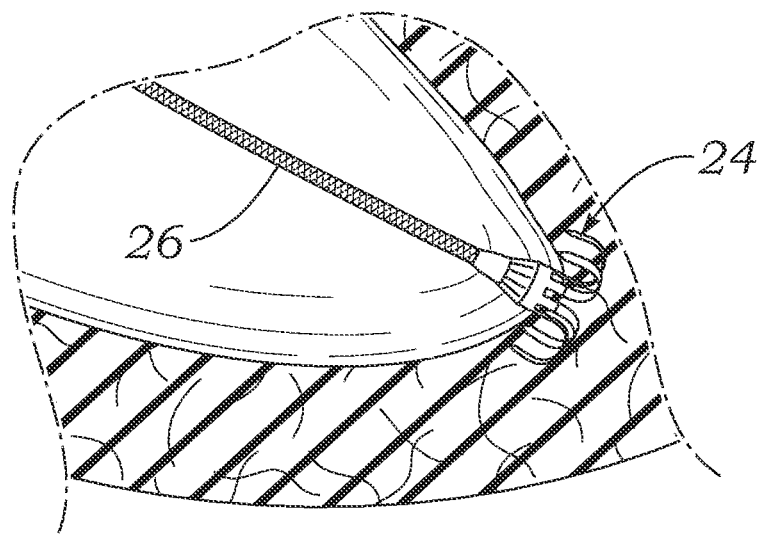

First, a detail explanation of the structure and usage of an exemplary device anchor 24 will be provided with reference to FIGS. 2A-2C. FIG. 2A is an enlargement of the distal end of the anchoring catheter sheath 22 in the position of FIG. 1A. The device anchor 24 is seen within the sheath 22 positioned just within the distal end thereof. The device anchor 24 attaches to an elongated anchor rail 26, which in some versions is constructed to have good capacity for torque. For instance, the anchor rail 26 may be constructed as a braided wire rod, or cable.

In FIG. 2B, the catheter sheath 22 is shown being retracted proximally, while the device anchor 24 and anchor rail 26 are expelled distally therefrom. The exemplary device anchor 24 includes a plurality of circumferentially distributed and distally-directed sharp tines or barbs 28 that pierce the tissue of the ventricular apex. The barbs 28 are held in a stressed configuration within the sheath 22, and are provided with an outward elastic bias so that they curl outward upon release from the sheath. Desirably the barbs 28 are made of a super-elastic metal such as Nitinol. The outward curling of the barbs 28 can be seen in both FIGS. 2B and 2C, the latter showing the final relaxed configuration of the barbs. The operation to embed the device anchor 24 may be controlled under visualization, such as by providing radiopaque markers in and around the device anchor 24 and distal end of the catheter sheath 22. Certain other devices described herein may be used to help position the device anchor 24 at the ventricular apex, as will be described. Although the particular device anchor 24 shown in FIGS. 2A-2C is considered highly effective, other anchors are contemplated, such as shown and described below, and the application should not be considered limited to one type or another.

To facilitate central positioning of the anchor rail 26 during deployment the device is implanted with the assistance of a fluoroscope. For example, after properly positioning the patient so as to maximize the view of the target annulus, for example the tricuspid annulus, a pigtail catheter is placed in the right ventricle and contrast injected. This allows the user to see a clear outline of the annulus and the right ventricle. At this point, a frame of interest is selected (e.g., end systole) in which the annulus is clearly visible and the annulus to ventricular apex distance is minimized. On the monitor, the outline of the right ventricle, the annulus, and the pulmonary artery are traced. The center of the annulus is then identified and a reference line placed 90° thereto is drawn extending to the right ventricular wall. This provides a clear linear target for anchoring. In a preferred embodiment, the anchor 24 is preferably located in the base of the ventricle between the septum and the free wall.

Aligning the anchor rail 26 in this manner helps center the eventual positioning of a coapting element of the system within the tricuspid leaflets. If the coapting element is offset to the anterior or posterior side, it may get stuck in the tricuspid valve commissures resulting in leakage in the center of the valve. An alternative method is to place a device such as a Swan Ganz catheter through the right ventricle and into the pulmonary artery to verify that the viewing plane is parallel to the anterior/posterior viewing plane. Addition of a septal/lateral view on the fluoroscope may be important to center the anchor in patients that have a dilated annulus and right ventricle.

Figure 5:
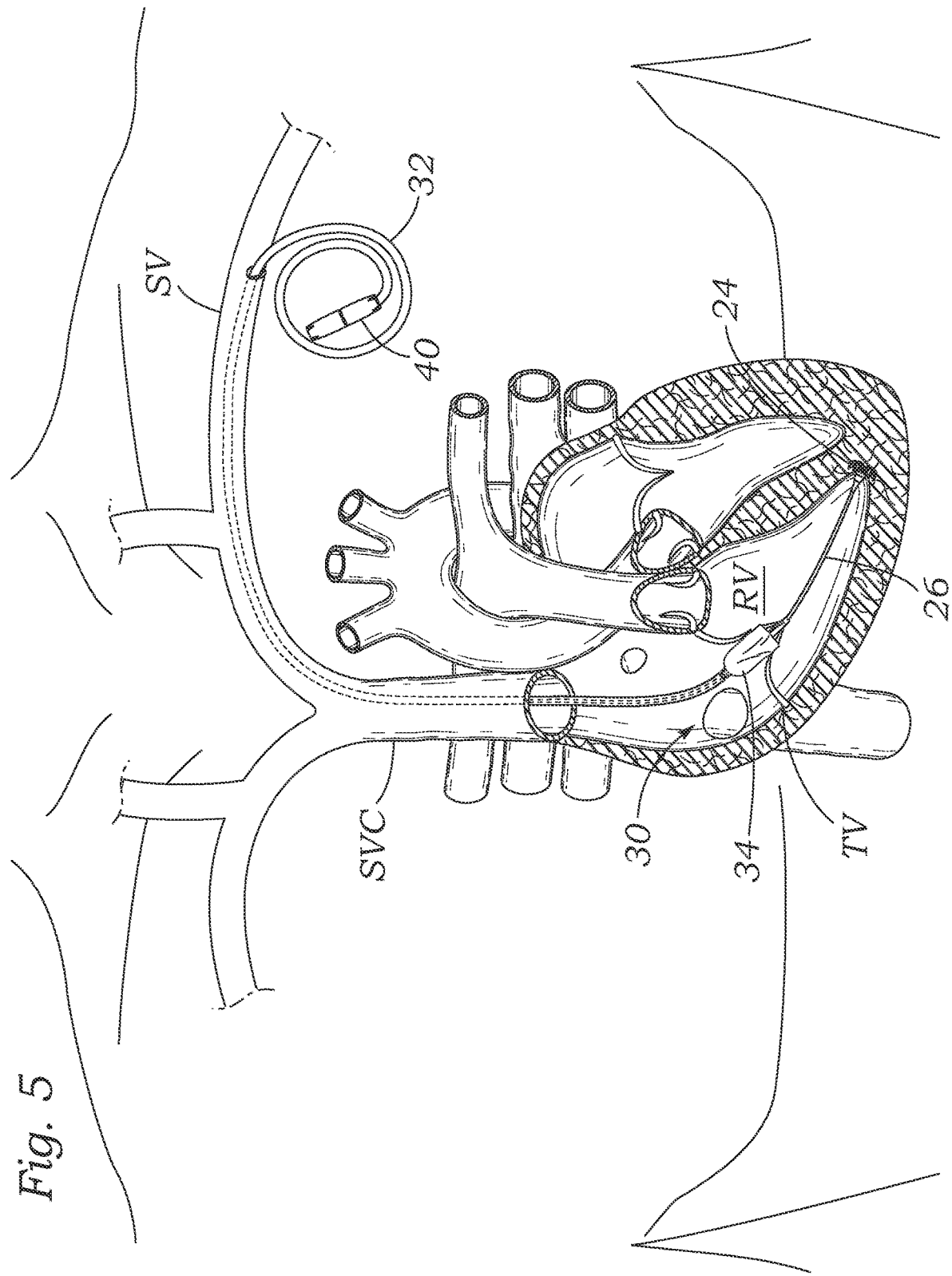
FIG. 5 is a broader view of the final configuration of the regurgitation reduction device of the present application with a coapting element positioned within the tricuspid valve and a proximal length of the delivery catheter including the locking collet shown exiting the subclavian vein to remain implanted subcutaneously.

FIGS. 3A and 3B illustrate deployment of a regurgitation reduction device 30 including a delivery catheter 32 advanced along the anchor rail 26 to position a coapting element 34 within the tricuspid valve TV. The coapting element 34 fastens to a distal end of the delivery catheter 32, both of which slide along the anchor rail 26, which has been previously positioned as described above. Ultimately, as seen in FIG. 3B, the coapting element 34 resides within the tricuspid valve TV, the leaflets of which are shown closed in systole and in contact with the coapting element. Likewise, the delivery catheter 32 remains in the body as seen in FIGS. 3B and 5, and the prefix "delivery" should not be considered to limit its function. A variety of coapting elements are described herein, the common feature of which is the goal of providing a plug of sorts within the heart valve leaflets to mitigate or otherwise eliminate regurgitation. In the illustrated embodiment, the coapting element 34 includes an inner strut structure partly surrounded by bioprosthetic tissue, as will be described in more detail below.

A locking mechanism is provided on the regurgitation reduction device 30 to lock the position of the coapting element 34 within the tricuspid valve TV and relative to the fixed anchor rail 26. For example, a locking collet 40 along the length of the delivery catheter 32 permits the physician to selectively lock the position of the delivery catheter, and thus the connected coapting element 34, on the anchor rail 26. There are of course a number of ways to lock a catheter over a concentric guide rail, and the application should not be considered limited to the illustrated embodiment. For instance, rather than a locking collet 40, a crimpable section such as a stainless steel tube may be included on the delivery catheter 32 at a location near the skin entry point and spaced apart from the location of the coapting element 34. The physician need only position the coapting element 34 within the leaflets, crimp the catheter 32 onto the anchor rail 26, and then sever both the catheter and rail above the crimp point.

Details of the exemplary locking collet 40 are seen in FIGS. 4A-4C. The collet 40 includes two short tubular grips 42a, 42b that are internally threaded and engage a common externally threaded tubular shaft member 44. The delivery catheter 32 is interrupted by the collet 40, and free ends of the catheter fasten within bores provided in opposite ends of the grips 42a, 42b. As seen in FIG. 4B, the anchor rail 26 extends through the middle of the locking collet 40, thus continuing the length of the delivery catheter 32. Furthermore, when the grips 42a, 42b are separated from each other as seen in FIGS. 4A and 4B, the anchor rail 26 slides freely through the locking collet 40.

An inner, generally tubular wedge member 46 is concentrically positioned between the shaft member 44 and the anchor rail 26. One or both ends of the wedge member 46 has a tapered surface 48 (see FIG. 4C) that interacts with a similarly tapered inner bore of the surrounding tubular grip 42a, 42b. The wedge member 46 features a series of axial slots extending from opposite ends which permit its diameter to be reduced from radially inward forces applied by the surrounding grips 42a, 42b and shaft member 44. More particularly, FIG. 4C shows movement of the two grips 42a, 42b toward each other from screwing them together over the threaded shaft member 44. Desirably, outward ribs or other such frictional enhancers are provided on the exterior of both of the grips 42a, 42b to facilitate the application of torque in the often wet surgical environment. Axial movement of the tapered inner bore of one or both of the grips 42a, 42b forces inward the tapered surface 48 of the wedge member 46, and also the outer ends of the shaft member 44. In other words, screwing the grips 42a, 42b together cams the shaft member and a wedge member 46 inward. The dimensions are such that when the two grips 42a, 42b come together, the inward force applied by the wedge member 46 on the anchor rail 26 is sufficient to lock the delivery catheter 32 and anchor rail.

Now with reference to FIG. 5, the entire regurgitation reduction device 30 can be seen extending from the apex of the right ventricle RV upward through the superior vena cava SVC and into the subclavian vein SV. A proximal length of the delivery catheter 32 including the locking collet 40 exits the subclavian vein SV through a puncture and remains implanted subcutaneously; preferably coiling upon itself as shown. In the procedure, the physician first ensures proper positioning of the coapting element 34 within the tricuspid valve TV, then locks the delivery catheter 32 with respect to the anchor rail 26 by actuating the locking collet 40, and then severs that portion of the delivery catheter 32 that extends proximally from the locking collet. The collet 40 and/or coiled portion of the delivery catheter 32 may be sutured or otherwise anchored in place to subcutaneous tissues outside the subclavian vein SV. It is also worth noting that since the delivery catheter 32 slides with respect to the anchor rail 26, it may be completely removed to withdraw the coapting element 34 and abort the procedure—either during or after implantation. The implant configuration is similar to that practiced when securing a pacemaker with an electrode in the right atrium muscle tissue and the leads extending to the associated pulse generator placed outside the subclavian vein. Indeed, the procedure may be performed in conjunction with the implant of a pacing lead.

Coapting Elements:

As mentioned, a number of different coapting elements are described in the present application. Indeed, the present application provides a plurality of solutions for preventing regurgitation in atrioventricular valves, none of which should be viewed as necessarily more effective than another. For example, the choice of coapting element depends partly on physician preference, partly on anatomical particularities, partly on the results of clinical examination of the condition of the patient, and other factors.

One broad category of coapting element that is disclosed herein and has been subject to testing is a flexible mechanical frame structure at least partially covered with bioprosthetic tissue. The inner frame structure is flexible enough to react to the inward forces imparted by the closing heart valve leaflets, and therefore undergo a shape change to more completely coapt with the leaflets, thus reducing regurgitant jets. The bioprosthetic tissue covering helps reduce material interactions between the native leaflets and the inner mechanical frame. As mentioned above, the regurgitation reduction device can be effectively deployed at either the tricuspid or mitral valves, the former which typically has three leaflet cusps defined around the orifice while the latter has just two. The tissue-covered mechanical frame structure thus represents an effective co-optation element for both valves by providing a highly flexible structure which is substantially inert to tissue interactions.

An exemplary embodiment of this so-called "Flexible Bell Coaptation Element" consists of a pericardial tissue (or a biocompatible flexible material) that is cut and sewn to create a sac/bell shape that is able to hold liquid (blood). One embodiment is designed to sit in the valve plane such that the open end is towards the atrium and the closed portion towards the ventricle. Therefore during diastole, blood flows into the coaptation element and fills the sac, conversely during systole as the native leaflets begin to close and contact the coaptation element, the pressure and blood flow work to decrease the size of the coaptation element by pushing blood out of the top edge sufficiently while still creating a seal.

Variations on the system include various design shapes at the ventricular end that is closed such as a half circle, triangle, ellipse or the like. Additionally sutures on the closed end as well as axially along the coaptation element better define how the element closes from interaction with the native leaflets. Lastly a more rigid support such as cloth, wire or other material could be sutured along the open atrial seated edge to ensure that the design remained open during the cardiac cycle. These principles apply equally to coapting elements that are open to the ventricle and closed to the atrium.

Figure 6B:
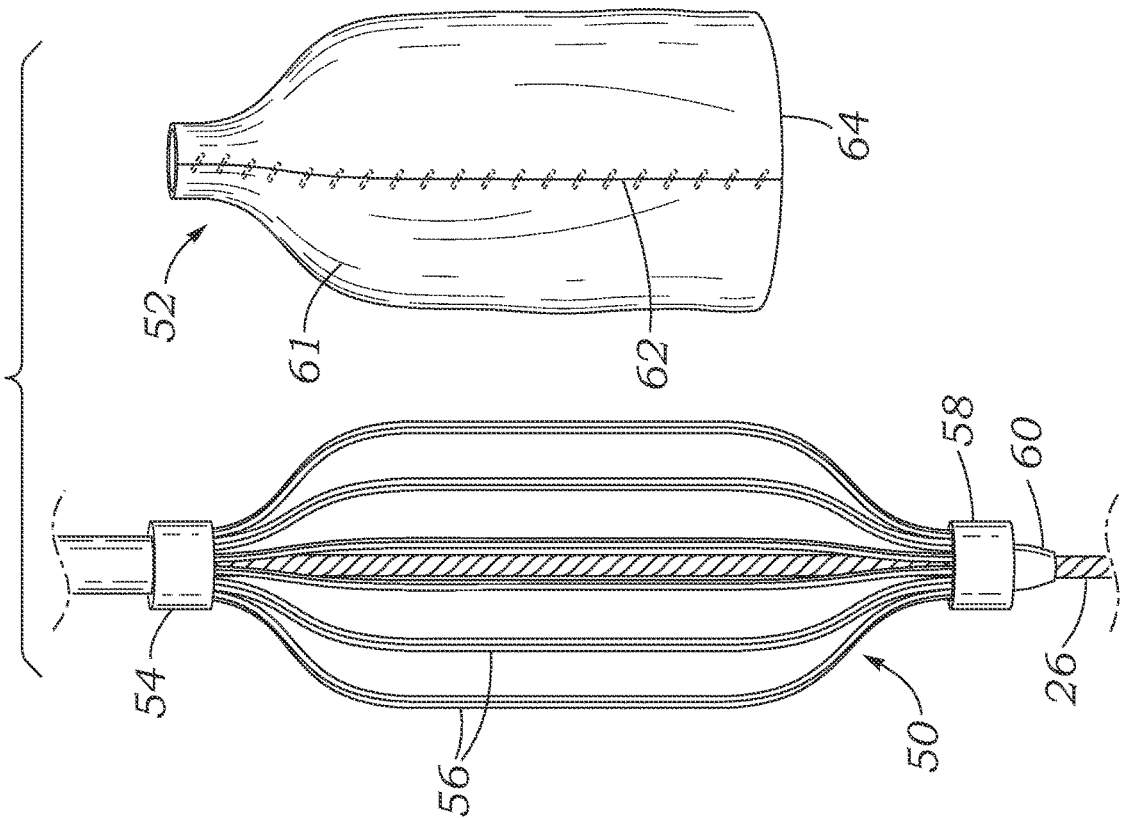
FIGS. 6A and 6B are assembled and exploded elevational views of an exemplary coapting element having an inner strut frame and tissue partially covering an atrial end of the coapting element.
Figure 6A:
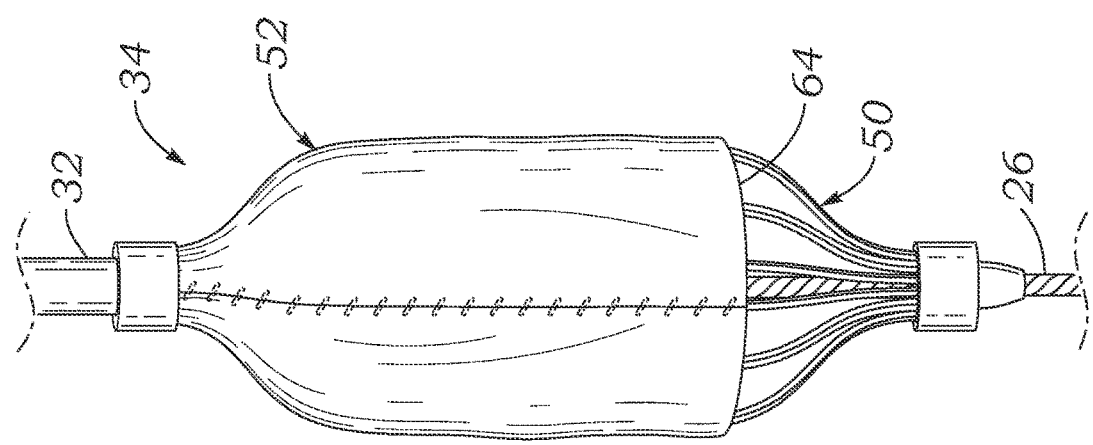

FIGS. 6A and 6B are assembled and exploded elevational views of an exemplary coapting element 34 having an inner strut frame 50 and a tissue cover 52 partially covering an atrial end of the coapting element. For the sake of uniformity, in these figures and others in the application the coapting elements are depicted such that the atrial end is up, while the ventricular end is down. These directions may also be referred to as "proximal" as a synonym for up or the atrial end, and "distal" as a synonym for down or the ventricular end, which are terms relative to the physician's perspective.

A small portion of the delivery catheter 32 is seen at the proximal end of the coapting element 34. In one embodiment, a short tubular collar 54 fastens to the distal end of the delivery catheter 32 and provides structure to surround the proximal ends of a plurality of struts 56 that form the strut frame 50. A second tubular collar 58 holds together the distal ends of the struts 56 and attaches to a small ferrule 60 having a through bore that slides over the anchor rail 26. Each of the struts 56 has proximal and distal ends that are formed as a part of (or constrained within) these collars 54, 58 and a mid-portion that arcs radially outward to extend substantially parallel to the axis of the coapting element 34. The frame shape is thus a generally elongated oval. In the illustrated embodiment, there are six struts 56 in the frame 50, although more or less could be provided. The struts 56 are desirably formed of a super-elastic material such as Nitinol so as to have a minimum amount of rigidity to form the generally cylindrical outline of the frame but maximum flexibility so that the frame deforms from the inward forces imparted by the heart valve leaflets.

The tissue cover 52 preferably comprises one or more panels 61 of bioprosthetic tissue sewn around the struts 56 of the frame 50. A single axial seam 62 is shown in the figures, though as will be explained below the cover 52 is typically formed of two or three panels sewn together with a matching number of seams. The tissue cover 52 may be formed of a variety of xenograft sheet tissue, though bovine pericardial tissue is particularly preferred for its long history of use in cardiac implants, physical properties and relative availability. Other options are porcine or equine pericardium, for example. In the embodiment illustrated in FIGS. 6A-6C, the tissue cover 52 has a proximal end that is closed to fluid flow, and a distal end 64 that is open; thus, the cover resembles a bell shape. Desirably, the axial length of the cover 52 extends from the proximal collar 54 approximately three-quarters of the way down to the distal collar 58, to the end of the flat section of the device. As mentioned above, the open bell shape desirably facilitates functioning of the coapting element. Namely, during diastole, blood flows around the coaptation element 34, while during systole, as the native leaflets close and contact the coaptation element, the pressure and blood flow work to fill the interior of the coaptation element by pushing blood in, the interior of the coaptation element is at the same pressure as the RV and a seal is created. These phases of the cardiac cycle are common to both the tricuspid and mitral valves. Generally the coaptation elements that are closed on the atrial side and open to the ventricular side move essentially like a parachute—filling in systole, and blood flowing around without collapse in diastole.

FIGS. 7A and 7B illustrate an alternative coapting element 68 much like the coapting element 34 described above, having an inner strut frame 70 and a tissue cover 72 partially covering a ventricular end of the coapting element, which functions like a flexible cup to block regurgitation. Indeed, the structure of the coapting element 68 is identical to that described above except for two features—the tissue cover 72 is closed at the ventricular end, but open at the atrial end, and there are three elongated struts 74 extending between and captured by upper and lower collars 76a, 76b. The number of struts can vary for both designs, though 6 or 9 struts are currently contemplated. Once again, the delivery catheter 32 fixes to the upper collar 76a, while the anchor rail 26 extends through the entire structure and slides through the lower collar 76b. After implant of the upwardly opening coapting element 68, blood will close the tricuspid valve leaflets during systole around the tissue cover 72 (as in FIG. 3B) with relatively little resistance from the coapting element. Conversely, during diastole blood flows downward from the right atrium to the right ventricle around the coapting element 68, and though some will flow into and inflate the tissue cover 72, its size will not significantly impede filling of the right ventricle.

FIG. 8 is an assembled elevational view of a still further coapting element 80 having a tissue cover 82 on the atrial end (open to the ventricle) and cantilevered struts (not visible) extending from the atrial end within the tissue cover. That is, the coapting element 80 is similar to coapting element 34 from FIG. 6A, though instead of an oval-shaped mechanical frame within the tissue cover 82, the struts are simply fixed to and cantilevered from an atrial collar 86. As before, the delivery catheter 30 attaches to the collar 86, and the entire assembly slides over the anchor rail 26.

FIGS. 9A-9C illustrate another coapting element 90 with a tissue cover 92 open to the atrial end and cantilevered struts 94 extending from a collar 96 at the ventricular end. In other words, the coapting element 90 is essentially an inverse to the coapting element 80 of FIG. 8. FIG. 9B shows the coapting element 90 looking down from the atrial side in an expanded configuration of the tissue cover 92 in diastole when blood flows downward from the right atrium to the right ventricle and inflates the cover. In FIG. 9C, systolic pressures in the right ventricle close the tricuspid valve leaflets around the coapting element 90, thus causing it to collapse and force blood from the interior of the tissue cover 92 into the right atrium. It will be noticed that some of the struts 94 collapse inward more than others, reflecting the uneven inward forces imparted by the tricuspid leaflets. Struts that do not deform so much remain bowed outward toward the valve commissures. The diagram is schematic and shown with three struts moving all the way in and three remaining in approximately the same position. However, it will be understood that the compacted shape of the coapting element 90 will be relatively random, and may change from cycle to cycle.

FIGS. 10A-10B shows a still further embodiment of a coapting element 100 having an atrial end tissue cover 102, similar to that shown in FIGS. 6A and 8, but with an inner strut configuration with some struts 104 extending the full length of the coapting element and some struts 106 cantilevered from the atrial end, in particular from an atrial collar 108. The staggered nature of the full-length struts 104 and cantilevered struts 106 is seen from the ventricular end in FIG. 10B. With this configuration, segments of the coapting element 100 having the cantilevered struts 106 are more inwardly flexible than the segments having the full-length of struts 104, which provides a collapsible structure that is someone more flexible than the embodiment of FIG. 6A but more rigid than the embodiment shown in FIG. 8.

FIGS. 11A-11B illustrate a similar coapting element 110 as in FIGS. 10A-10B, but with the tissue cover 112 and struts 114, 116 extending from the ventricular end, preferably from a ventricular collar 118.

Many of the coapting elements described herein benefit from the use of a bioprosthetic tissue covering. Often, such tissue coverings must be stored in a preservative solution, such as glutaraldehyde, for long periods, which may be deleterious to the material of the synthetic components of the overall device. Accordingly, any of the bioprosthetic tissue coapting elements described herein should be stored separately from other components that could be damaged from long-term storage and preservative solution, such as polymer catheters and the like.

Figure 12:
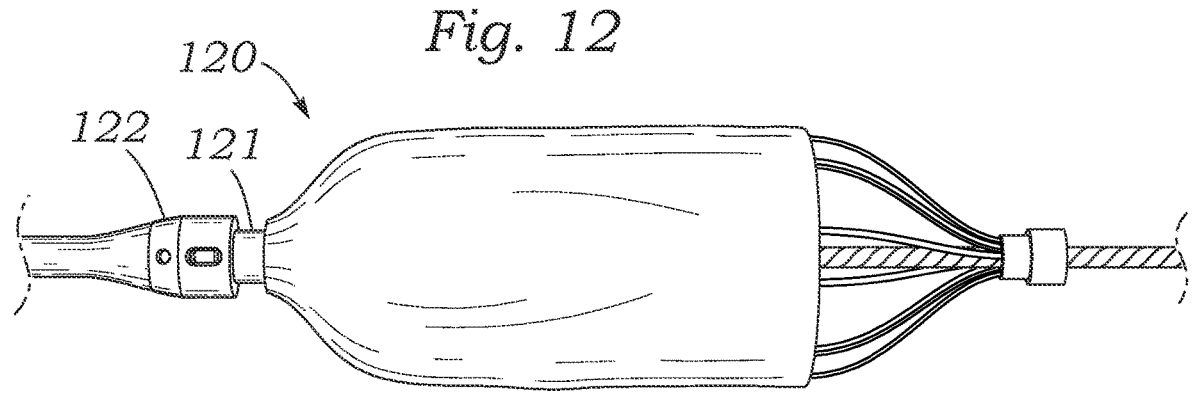
FIG. 12 is an elevational view of a coaptation element much like FIG. 6A, but with a modified coupling structure on the proximal end of an inner mechanical frame that permits a delivery catheter to be snap fit thereto.
Figure 12A:
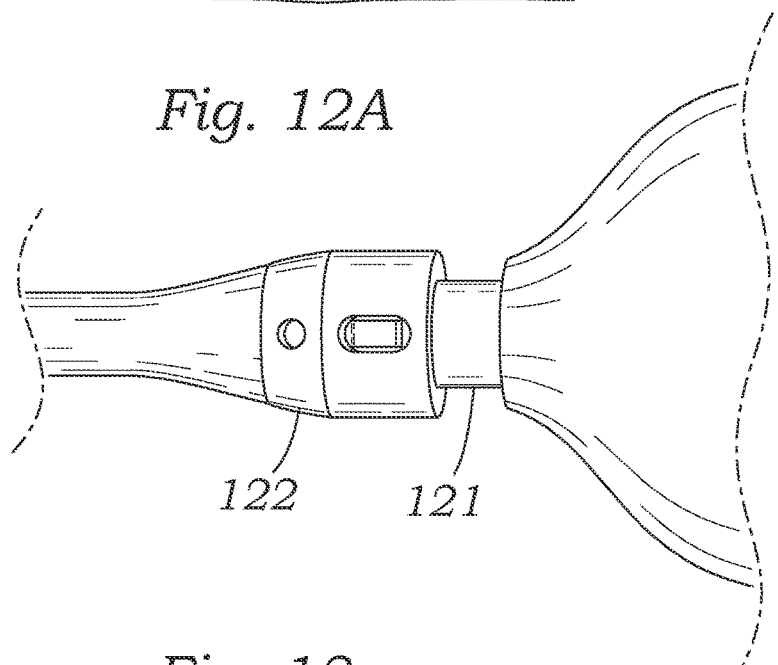
FIG. 12A is an enlargement of the proximal coupling.
Figure 13:
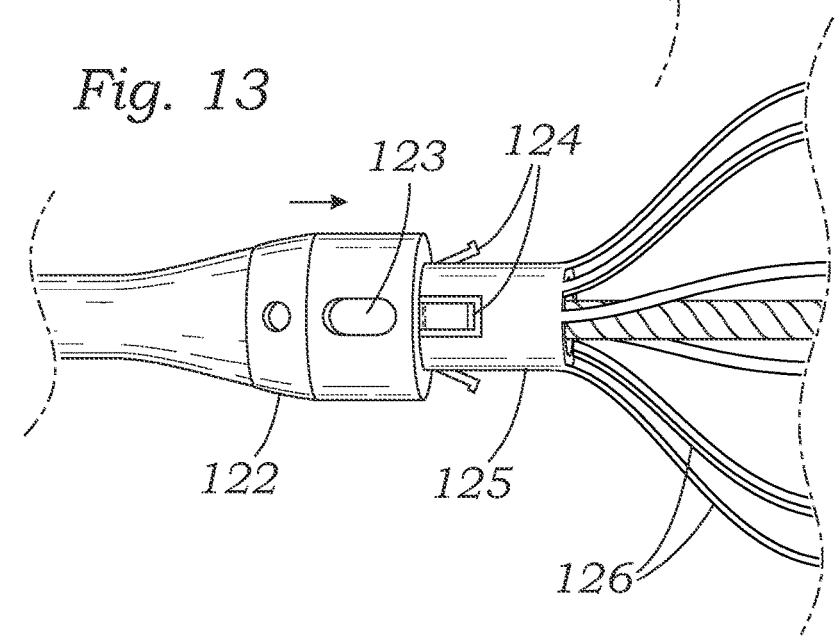
FIG. 13 is an enlarged view of the proximal coupling between the delivery catheter and the mechanical frame of FIG. 12.

FIGS. 12, 12A, and 13 illustrate one such arrangement where a coapting element 120 has a proximal coupling sleeve 121 that can be snap fit to a distal coupler 122 of a delivery catheter. More particularly, FIGS. 12A and 13 show small oval windows 123 in the coupler 122 which received outwardly biased spring tabs 124 on a tubular hub 125 of the coupling sleeve 121. At the time of the surgical procedure, a technician in the operating room removes the bioprosthetic coapting element 120 from its liquid-filled storage container, typically rinsing it, and then joins the catheter coupler 122 to the proximal sleeve 121 by pushing the two together until the tabs 124 spring outward through the windows 123. It should be also noted that the internal mechanical frame structure including the flexible struts 126 are formed in one homogenous piece with the tubular hub 125 of the coupling sleeve 121, which improves long-term integrity of the entire structure.

As mentioned above, a preferred construction of the mechanical frame/tissue cover coapting elements includes a plurality of panels of bioprosthetic tissue sewn to the inner struts. FIGS. 14A-14C schematically illustrate several different configurations of three-strut/three-panel coapting elements in this regard. More particularly, FIG. 14A shows the three panels 128 of bioprosthetic tissue having generally rectangular configurations except for their lower ends which are pointed. A view of the finished coapting element from its open end is seen to the right wherein all of the six struts 130 are cantilevered from the closed end. In a preferred construction, cloth pieces 132 are first sewn around some or all of the struts 130. Separately, the three tissue panels 128 are sewn to each other to form a tubular structure, and such that the flaps of the longitudinal seams face to the inside of the tube. This may require first sewing the seams on the outside and then inverting the tubular structure. Subsequently, the tubular structure of the three panels 128 is sewn to the cloth pieces 132 preassembled around some or all of the struts. In the illustrated embodiment, there are three panels 128 and thus three seams, so that only three cloth pieces 132 are used around three of the six struts 130. Finally, the pointed lower ends of the tissue panels 128 are sewn together to close off that end, whether it be the atrial or ventricular side.

FIG. 14B is much the same as the construction of FIG. 14A; however the mechanical frame structure has six struts 134 that extend the full length of the coapting elements with none of them cantilevered. Finally, FIG. 14C shows another similar embodiment wherein there are three struts 136 extending the full length of the coapting element, with three intermediate struts 138 cantilevered from the closed end of the mechanical frame.

FIG. 15 schematically illustrates components in the construction of a two-strut/two-panel coapting element. Because of the modified three-dimensional shape, the lower ends of the panels 140 are curved rather than pointed. The two struts 142 extend the full length of the coapting element and are diametrically opposed. This coapting element thus has a much more two-dimensional shape, though the open end of the tissue cover permits the structure to be inflated when the element is pressurized from the open end.

FIG. 16 is a schematic diagram of a pair of native tissue leaflets 144 indicating certain key dimensions used in constructing the coapting element. The inquiry seeks to determine a preferred height of the coapting element, or at least the height of the leaflet contacting surface of the elements. It is known that the length of heart valve leaflets are often mismatched, and the dimension LM indicates the leaflet mismatch as a distance along the axis of the valve. An axial dimension of a coapting element that fits within these two mismatched leaflets will therefore have a minimum height that starts at the tip of the longer leaflet and extends upward approximately twice the leaflet mismatch LM dimension, indicated as $H_{min}$. To avoid inserting too large a structure between the leaflets, a dimension $H_{max}$ extends from approximately the plane of the annulus of the leaflets (i.e., where they attach to the surrounding wall) down to a distance into the ventricle which is centered at the center of the dimension $H_{min}$. The leaflet excursion LE reflects the length along which the leaflets are known to contact the coapting devices. That is, the leaflets first hit the device and then move down with the contraction of the heart. There must therefore be enough surface length or leaflet excursion LE for the leaflets to maintain contact. In general, the axial dimension of the coapting element should ensure enough coaptation length to accommodate leaflet mismatch and leaflet excursion without protruding too much into the ventricle or atrium.

FIGS. 17A-17C illustrate another coapting element 150 having a three-strut mechanical frame 152, a tubular tissue covering 154, and an inner foam cylinder 156. The foam cylinder 156 has a through bore for receiving a delivery catheter 158. Three struts 160 are retained by a pair of end collars 162 secured to the delivery catheter 158. As described above, the tissue covering 154 desirably includes a plurality, typically three, of rectangular panels that are sewn together and then sewn to a cloth covering surrounding each of the struts (not shown). The resulting structure of the coapting element 150 is compressible, though the inner foam cylinder 156 expands in its relaxed configuration to provide a generally continuous curved outer surface for good contact with the surrounding heart valve leaflets.

FIG. 18 illustrates one technique for compressing the coapting element 154 for introduction into a patient's vasculature, such as into a patient's subclavian vein. A generally funnel-shaped introducer 170 has a wide proximal end 172 and a much smaller distal end 174, with the diameter either stepping down intermittently along its length or continuously. By pushing the delivery catheter and ultimately the coapting element 150 into the introducer 170 from its proximal end 172, the coapting element can be gradually compressed until it fits through the narrow distal end 174. The distal end 174 may be inserted directly into the subclavian vein, or may connect to a pre-inserted delivery sheath of approximate the same diameter.

FIGS. 19 and 20 illustrate an alternative coapting element 180 comprising a bell-shaped polymer member 182 held open at one end via a multi-strut frame 184. An upper or atrial collar 186 connects both to the polymer member 182 and to a delivery catheter 30, although the polymer member may be connected directly to the delivery catheter such as via heat bonding. The delivery catheter 30 extends through the interior of the polymer member 182 and rides over the anchor rail 26, as before. The multi-strut frame 184 includes a ventricular collar 188 that attaches to the delivery catheter 30 and has a plurality, preferably three, struts 190 that angle outward therefrom in a proximal or atrial direction and terminate in small pads or feet 192. The feet 192 attach to an inner surface of a distal or ventricular reinforcing band 194 on the bell-shaped polymer member 182. The struts 190 are resilient such that the feet 192 apply radial outward forces to the band 194 so as to maintain the distal end of the polymer member 182 open.

FIG. 21 is a partial cutaway perspective view of a coapting element 180' similar to that shown in FIG. 19, but having a multi-strut frame 184' which is positioned within the bell-shaped polymer member 182. The delivery catheter 30 may extend just past the ventricular collar 188' or farther down into the ventricle as shown, such as to provide an expansion balloon to assist in guiding the anchor rail 26 to a proper anchoring position, as will be described below.

Both the coapting elements 180 and 180' include relatively square closed ends 196 of the polymer members 182, 182'. This is believed to be beneficial to avoid elongated narrow internal spaces where blood might stagnate and perhaps coagulate. A preferred material for the polymer members 182, 182' is a polycarbonate urethane (Carbothane from Lubrizol, Bionate from DSM, ChronoFlex from Advansource) which has extremely good durability over long periods of time, as opposed to materials such as Nylon used for typical catheter balloons. Alternatively, a polycarbonate silicone may also be used. In one embodiment, the outside diameter of the polymer members 182, 182' is about 10 mm, while the inside diameter of the neck that attaches to the delivery catheter 30 is about 0.10 inches (2.54 mm), and the constant diameter tubular portion is around 25 mm.

Figure 22C:
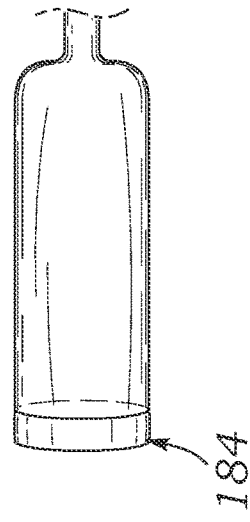
FIGS. 22A-22G illustrates an exemplary assembly sequence for the coapting element of FIGS. 19 and 21.
Figure 22B:
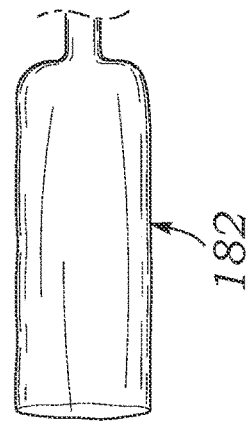
Figure 22A:
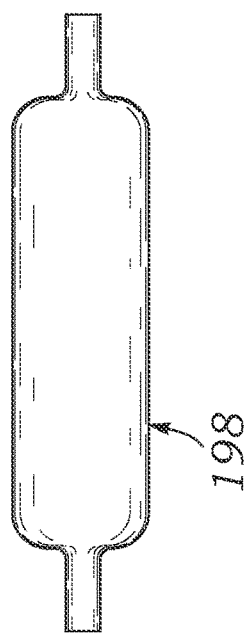
Figure 22F:
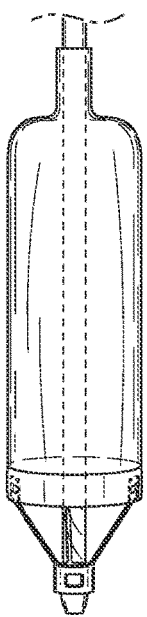
Figure 22E:
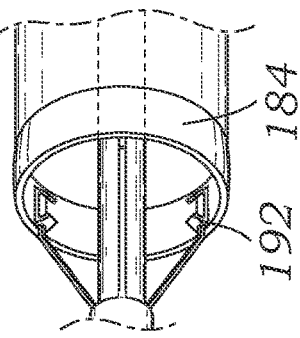
Figure 22D:
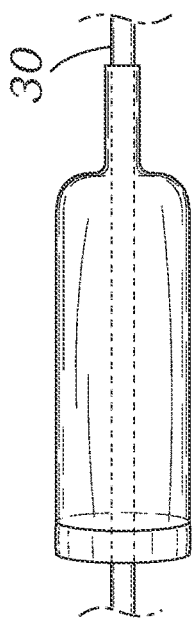
Figure 22G:
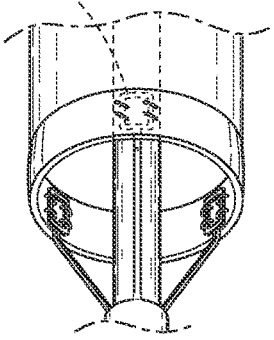

FIGS. 22A-22G illustrates an exemplary assembly sequence for the coapting element 180 and 180' of FIGS. 19 and 21. First, a polycarbonate urethane balloon 198 having substantially square ends seen in FIG. 22A is cut to length to result in the open-ended polymer member 182 in FIG. 22B. Subsequently, a band 184 of polymer reinforcing material is he bonded to the open end of the polymer member 182. The reinforcing material may be made of the same material as the polymer balloon but in a thicker extrusion. In one embodiment, the reinforcing band 192 is also radiopaque to provide visibility of the open end of the device. Subsequently, as seen in FIG. 22D, a neck portion of the polymer member 182 is heat bonded to the delivery catheter 30, or via an atrial collar as shown in FIGS. 19 and 21. FIGS. 22E and 22F show attachment of the feet 192 of the frame 184 to the reinforcing band 194. The feet 192 may be attached in a number of ways, including heat bonding, adhesive, or even via sutures. FIG. 22G shows a version where small sutures 199 are used to secure the feet 192 of the frame 184 to the band 194.

FIG. 23A is a perspective view of another coapting element 200 having an outer biocompatible tubular cover 202 mounted to an internal multiple strut frame 204 and enclosing a compressible member 206 such as foam therein. In a preferred embodiment, the tubular cover 202 comprises bioprosthetic tissue, such as bovine pericardial tissue, although other biocompatible materials such as the polycarbonate urethane described above could be used. FIG. 23B is an end view of the coapting element 200 illustrating the annular compressible member 206 surrounding the central delivery catheter 30, and showing the inset position of a plurality of longitudinal struts 208 that make up the frame 204. The delivery catheter 30 slides over the anchoring rail 26. As seen in FIG. 23A, the frame 204 includes an atrial collar 210 from which the struts 208 extend outward and then longitudinally approximately the entire length of the coapting element 200. The struts 208 are not joined at the distal end so as to be cantilevered from the collar 210. The collar 210 may attach via a snap-fit to a distal coupler 212 connected to the delivery catheter 30, much like the coupling sleeve 121 and distal coupler 122 described above with respect to FIG. 13.

FIGS. 24A-24C and 25A-25B illustrate a number of components forming the coapting element 200. A subassembly of the frame 204 is shown secured to three panels 214 that make up the tubular cover 202. In particular, the frame 204 defines a tripod shape with three struts 208 each of which extends along and defines a junction between adjacent panels 214. The coapting element 200 is relatively flush and cylindrical on its outer surface, with the struts 208 being inset therefrom. FIG. 24B shows the frame 204 isolated with fabric tubes 216 sewn to the longitudinal portion of the struts 208. FIG. 24C is a detail of the junction between the struts 208 and adjacent panels 214, wherein each panel includes an inwardly-directed edge which flanks the strut and is secured thereto via a number of sutures 218. The inset struts 208 and seam between the panels 214 are received in longitudinal outer grooves 219 formed in the compressible member 206, as seen in FIGS. 25A and 25B. As mentioned there are preferably three struts 208, but more or less could also be used. Furthermore, the compressible member 206 as an overall cylindrical outer profile, which substantially defines the final shape of the coapting element 200, but other cross-sectional shapes such as oval or rounded triangular may also be utilized.

As mentioned, the panels 214 of the tubular cover 202 are desirably bioprosthetic tissue, such as bovine pericardium. In a preferred embodiment, a smooth side of the pericardium is placed facing outward so as to render the exterior of the coapting element 200 smooth as well. As is well known, pericardium typically has a smooth side and a fibrous or rough side. The frame 204 is desirably highly flexible, such as being formed of Nitinol. The resulting coapting element 200 is highly compressible, thus responding to the forces imparted thereon by the surrounding valve leaflets and easily conforming so as to best prevent regurgitation.

FIG. 26A shows another coapting element 220 assembled, while FIG. 26B shows the individual components thereof exploded. The coapting element 220 includes an outer tubular cover 222 surrounding a porous compressible member 224, and has a proximal frame 226 connected between a proximal end of the tubular cover and a delivery catheter 30. The tubular cover 222 is desirably formed of a polycarbonate urethane. The frame 226 may be similar to those described above, having a tripod-shaped series of struts that terminate in feet 228 attached to a reinforcing or radiopaque band 230. The porous compressible number 224 is desirably formed of an open cell foam which enables a small amount of blood flow therethrough. An open cell foam polycarbonate urethane provided by Biomerix of Fremont, California may be desirable. Permitting slight blood flow through the coapting element 220 may help prevent stagnation and possible coagulation. Alternatively, the inner compressible member 224 may be a blood-impermeable foam, or an open cell foam covered with an impermeable layer.

FIGS. 27A and 27B are assembled and exploded views of a coapting element 230 similar to that in FIGS. 26A and 26B but wherein an outer cover 231 is bell-shaped with a closed ventricular end 232 and no supporting frame. The outer cover 231 is desirably a polycarbonate urethane, and preferably includes a radiopaque band 233 surrounding its proximal or atrial end.

FIG. 28 shows a coapting element 234 with an outer generally bell-shaped cover 235 surrounding an annular compressible member 236 mounted around an inner catheter 237 having perforations 238 for adding and removing air from the compressible member. As before, the inner catheter 237 slides over a flexible rail 26. The flow arrows in FIGS. 29A and 29B show the injection and aspiration of air, respectively, from the inner catheter 237 to and from the compressible member 236, which is desirably an open cell foam. In this way, the size of the coaptation element 234 may be reduced for delivery and increased after implant. The cover 235 thus functions something like a balloon, and is desirably formed of Carbothane. The catheter 237 is also made of Carbothane so that the distal and proximal necks of the cover 235 can easily be heat bonded thereto for a good seal, and is desirably reinforced to provide good inner support for the pressures generated within the cover 235.

FIG. 30 is a perspective view of a still further coapting element 240 having an outer bell-shaped cover 242 with a plurality of flow through holes 244 on an otherwise closed atrial end 246. A flexible frame 248 including a tripod of struts 250 maintains the distal or ventricular end open. FIGS. 31A and 31B show alternative hole patterns, which should not be considered limiting. For example, a circular array of round holes 244 as in FIG. 31A may be provided, or the pattern may be a regular distribution of non-circular such as rectangular through holes 254 as in FIG. 31B. The through holes 244, 254 are intended to permit a small amount of seepage through the otherwise closed end 246 of the coapting element 240, thus helping to avoid stagnation and coagulation of the blood.

Figure 32A:
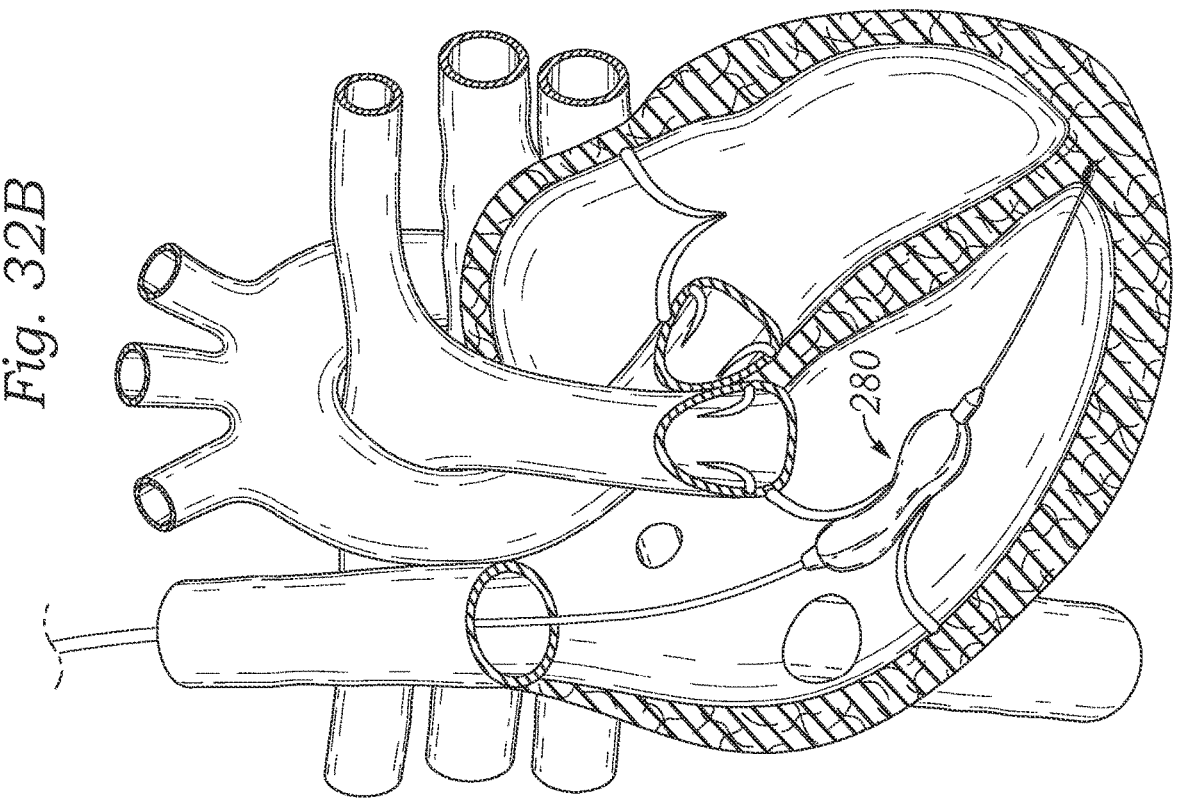
FIGS. 32A-32B are sectional views of the heart illustrating a regurgitation reduction device positioned in the right atrium/right ventricle and having a three-sided frame as a coaptation element.
Figure 32B:
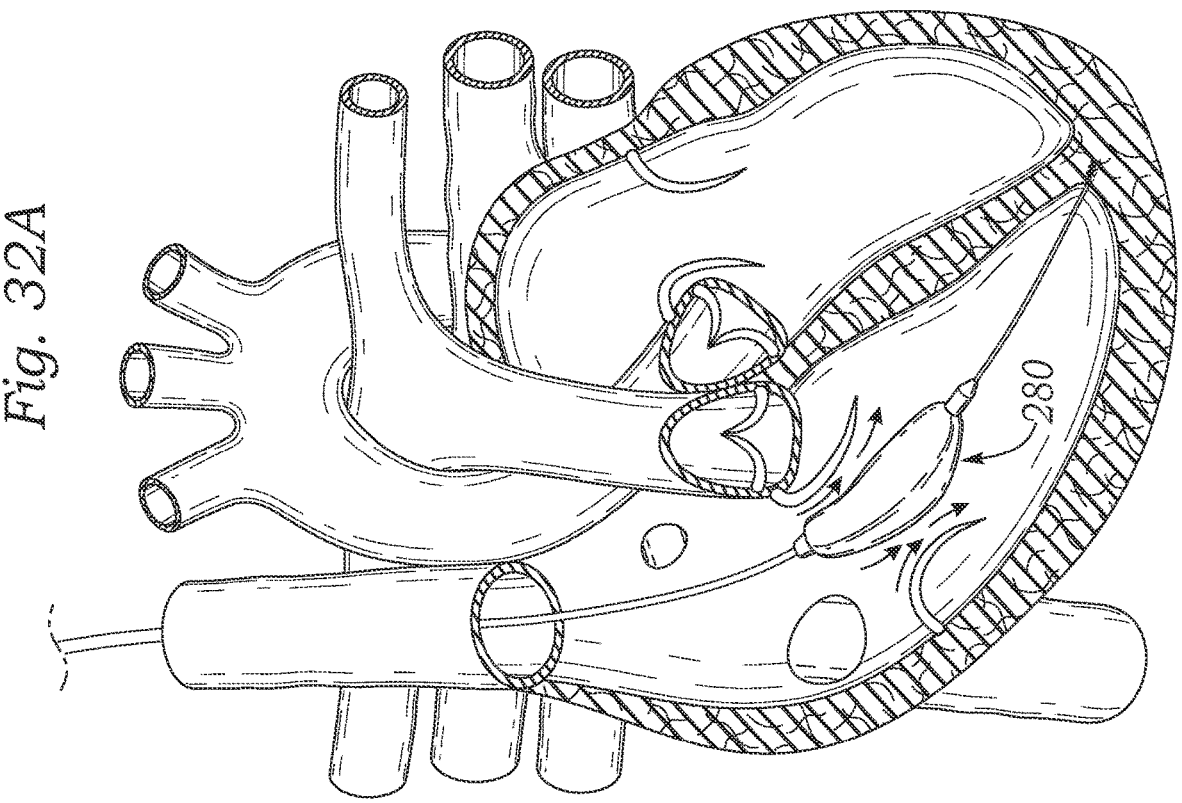
Figure 33A:
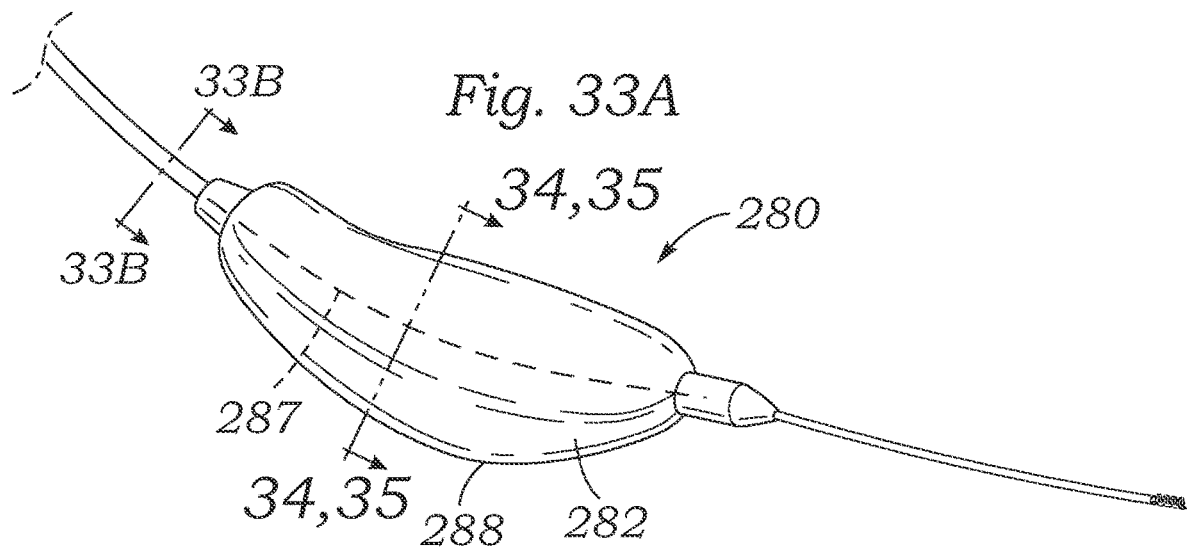
FIGS. 33A and 33B are elevational and end views of the coaptation element from FIGS. 32A-32B.
Figure 33B:
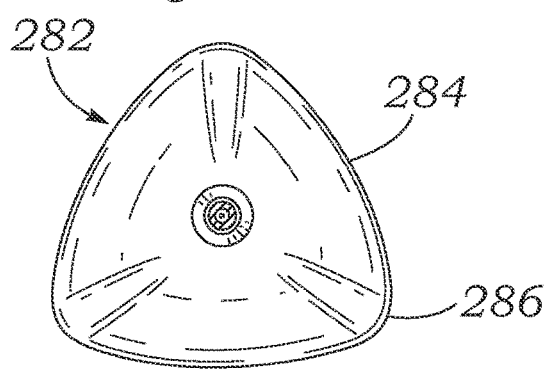

FIGS. 32A-32B illustrate a regurgitation reduction device 280 positioned in the right atrium/right ventricle having a three-sided frame 282 as a coaptation element, and FIGS. 33A and 33B show greater detail of the coaptation element. FIG. 32A shows the heart in diastole during which time venous blood flows into the right ventricle between the open tricuspid valve leaflets and the three-sided frame 282. In the systolic phase, as seen in FIG. 32B, the tricuspid leaflets close around the compressible frame 282, thus coapting against the frame and eliminating openings to prevent regurgitation.

FIG. 33B shows the desirably three-sided radial profile of the frame 282, with three relatively flat convex sides 284 separated by rounded corners 286. This rounded triangular shape is believed to faithfully conform to the three tricuspid leaflets as they close, this better preventing regurgitation. Moreover, the frame 282 is desirably under-filled with fluid so that it can be compressed and deformed by the leaflets. FIG. 33A also shows a preferred longitudinal profile of the frame 282, with an asymmetric shape having a gradually overall longitudinal curvature 287 and an enlarged belly region 288 just distal from a midline. The shape resembles a jalapeño pepper. Due to the curvature of the path from the superior vena cava SVC down through the tricuspid valve TV and into the right ventricle RV, the overall curvature 287 of the frame 282 helps position a mid-section more perpendicular to the tricuspid valve leaflets, while the uneven longitudinal thickness with the belly region 288 is believed to more effectively coapt with the leaflets.

Figure 34:
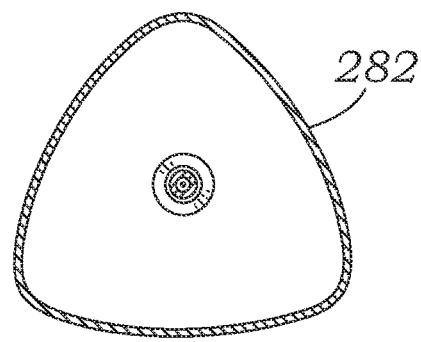
FIGS. 34 and 35 are radial section views through the coaptation element of FIG. 33A showing two different possible configurations, one hollow and one filled with a compressible material.
Figure 35:
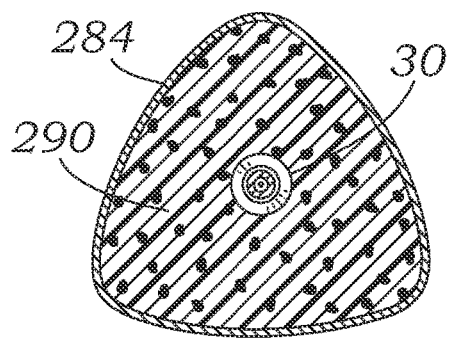

As an alternative to being fluid-filled, the frame 282 may have a plurality (e.g. >20) of very thin and highly flexible struts (not shown) that connect between top and bottom collars, for instance. The struts thus relocate independently of one another, which allows leaflet motion to deform the highly compliant frame 282 into whatever shape best conforms to the remaining orifice. Since segments of the frame 282 adjacent areas with high leaflet mobility would be compressed, the coaptation element could be dramatically oversized with respect to the regurgitant orifice size in order to maintain coaptation in commissural regions FIGS. 34 and 35 are radial section views through the coaptation element 280 of FIG. 33A showing two different possible configurations. In a first embodiment in FIG. 34, the coaptation element 280 is hollow or filled with a fluid such as saline. In a second embodiment in FIG. 35, the coaptation element 280 has a compressible member 290 interposed between an outer cover 284 and the delivery catheter 30. The compressible member 290 may be an open cell polycarbonate urethane foam, for example. Likewise, the outer cover may be a polycarbonate urethane. The latter configuration eliminates the potential for the fluid-filled frame 282 to deflate, thus maintaining good coaptation function for extended periods.

Figure 36A:
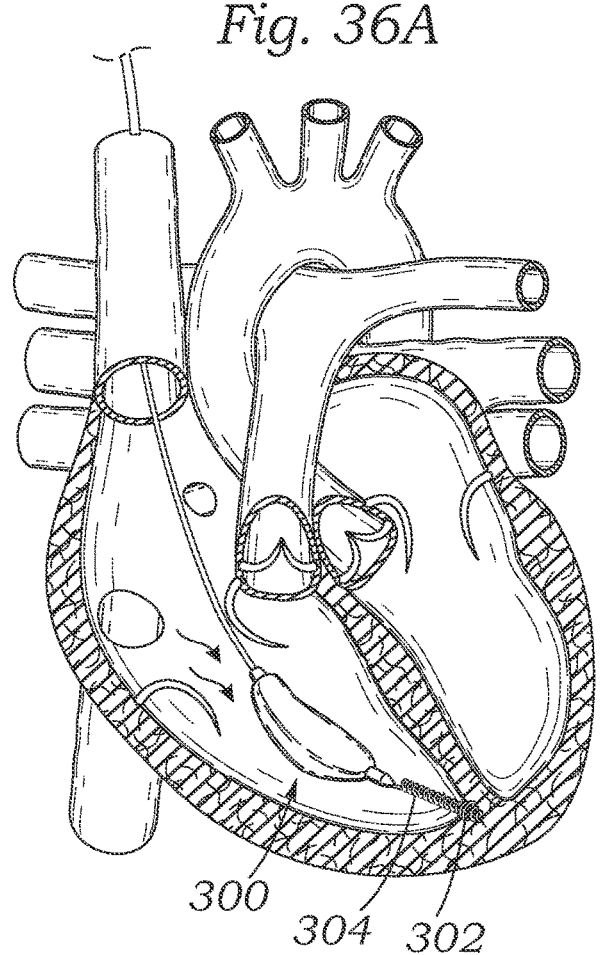
FIGS. 36A and 36B are sectional views of the heart in diastole and systole, respectively, showing a regurgitation reduction device which is mounted to the apex of the right ventricle with a spring that permits a coapting element to move in and out of the right ventricle in accordance with the cardiac cycle.
Figure 36B:
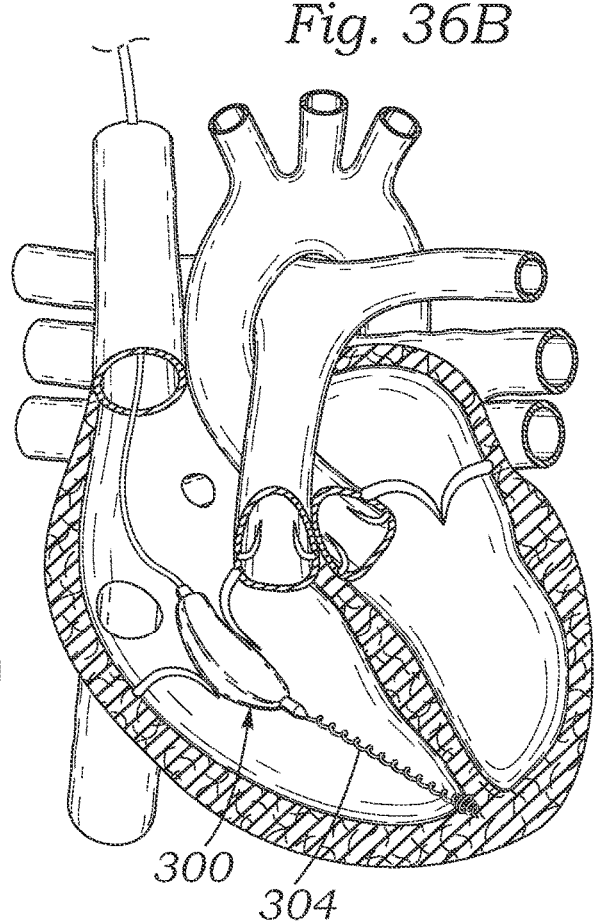

One potential challenge of a static coaptation element within the tricuspid valve annulus could be diastolic stenosis, i.e. restriction of blood flow from the right atrium to the right ventricle during diastole. In patients with an excessively large regurgitant orifice, sizing the device for proper coaptation during systole could have consequences in diastole. To address this issue, a coaptation element 300 could be attached to a flexible metallic spring 304 connected to anchor 302, therefore allowing the coaptation element to move in and out of the annulus plane during systole and diastole, respectively (see FIGS. 36A and 36B). During systole, as in FIG. 36B, the pressure gradient as well as fluid inertial forces would cause the spring 304 to extend, and during diastole the spring constant as well as fluid inertial forces would cause the spring to contract. Instead of just one spring distal to the coaptation element, a spring could be placed on both sides in order to increase mobility. Alternatively, with one spring, the "home" position of the coaptation element (i.e. with no force from the spring or fluid) could either be at the annulus plane or below the annulus plane in the RV. In the former case, inertial forces of diastolic flow would be required to move the coaptation element down out of the annulus plane during diastole, and in the latter case, both inertial forces of systolic flow and forces from the RV/RA pressure gradient could move the coaptation element up to the annulus during systole.

Figure 37:
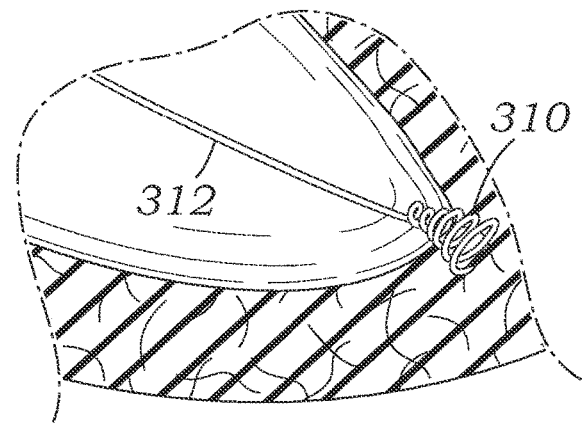
FIGS. 37 and 38 are views of alternative anchoring members utilizing coil springs.
Figure 38:
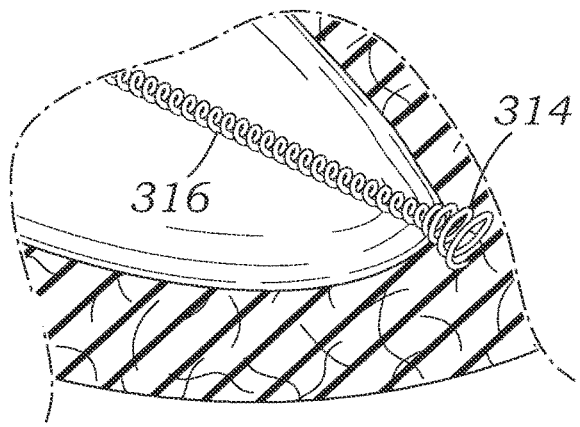

Anchors and Alternative Anchor Placement:

The following list of embodiments presents additional design ideas for the catheter railing and anchoring system:

FIGS. 37 and 38 are views of alternative anchoring members utilizing conical coil springs. One potential challenge of some proposed helical anchors is the limited surface area on which the anchor can "grab" tissue given its short cylindrical length (2 mm). In order to maximize the area of tissue contact over the 2 mm length of the anchor, a modified helical anchor 310 could be developed which has a conical shape, i.e. a circular cross-section of increasing size towards the distal end. The conical spring anchor 310 could be provide at the end of an anchor rail 312, as previously described. Such an anchor design could increase retention force by increasing the cross-sectional area of contact between the anchor coil and the tissue. Additionally, as the initial cut of the anchor 310 into the tissue would be largest followed by decreasing coil diameter as the anchor is screwed in, the anchor could effectively "cinch" in a volume of tissue into a compacted space. Such a feature could potentially minimize the risk for anchor tear-out by increasing the local tissue density at the anchor site. The conical spring 310 could be comprised of any shape memory material capable of collapsing or wrapping down to a smaller constant diameter to fit through a catheter lumen, then capable of expanding to the natural conical shape upon exiting the delivery sheath into the RV.

Alternatively, a conical anchor 314 could be connected via an elongated helical section 316 at its proximal end designed to remain in the RV (not screwed into the tissue but directly next to it), such as shown in FIG. 38. The elongated helical section 316 provides shock absorption capabilities against compressive/tensile stresses, thus reducing tearaway stresses on the RV apex, and also flexibility capabilities under bending stresses.

Figure 39:
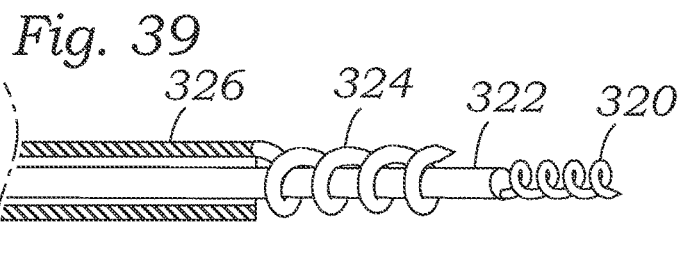
Figure 39A:
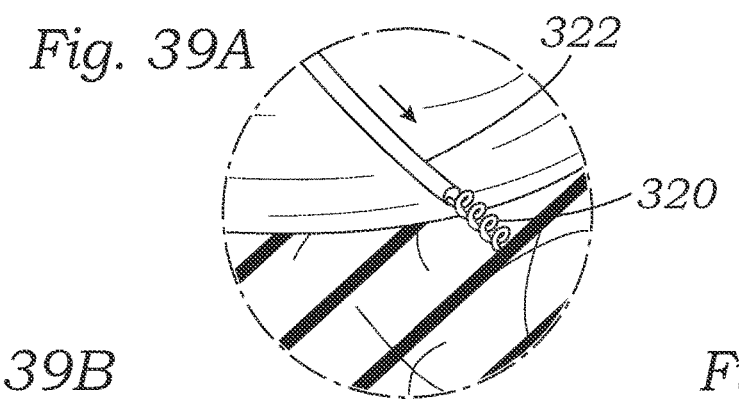
FIGS. 39A-39C illustrate steps in installation of the anchoring device.
Figure 39B:
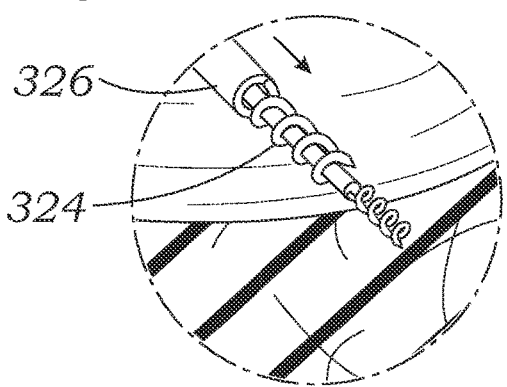
Figure 39C:
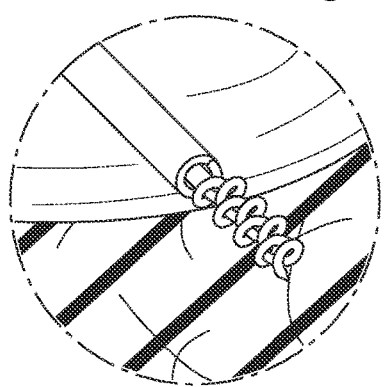

Using helical structures for anchoring the devices described herein in the right ventricle holds a number of advantages (e.g. ease of delivery, acute removability, minimal tissue damage, etc.). However, one potential challenge could be the tendency of a helical structure to "unscrew" itself out of the tissue, either acutely or over time due to the contractile motions of the ventricle. To address this issue, an anchor system in FIG. 39 includes concentric corkscrew anchors; an inner anchor 320 at the end of an inner tube 322, and an outer anchor 324 on the end of an outer tube 326. FIGS. 39A-39C illustrate steps in installation of the anchoring device, in which first the inner anchor 320 having a clockwise orientation is screwed into the tissue. Next, the slightly larger second anchor 324, having a counterclockwise orientation, and its tube 326 slide over the first anchor 320 and tube 322 and screws into the tissue in the opposite direction. Finally, the two anchors could be fixed together with a locking mechanism (e.g., pin-through-hole style). The resulting structure would resist unscrewing out of the tissue, since each helical coil opposes the twisting motion of the other.

Figure 40:
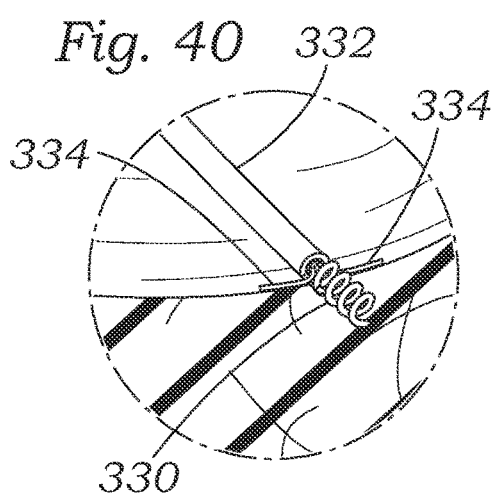
FIGS. 40 and 41 are views of still further anchoring members of the present application.

FIG. 40 shows another configuration with a helical corkscrew-type anchor 330 on the end of a tube 332, and a pair of struts 334 that may be independently expelled from the distal end of the tube into contact with the tissue surrounding the anchor. Rather than screwing in a second relatively similar anchor in the opposite direction to prevent twist-out, the struts 334 pass through the tube lumen and extend outwards in an L-shaped manner to provide an anti-rotation anchor to the device. These struts 334 should be thick enough to press against the RV apex tissue and apply friction thereto to prevent twisting motion of the anchor 330.

Figure 41:
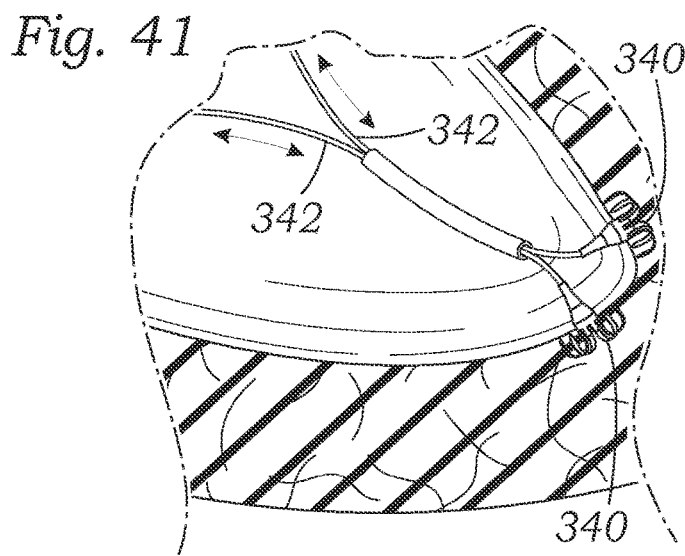

In an alternative approach to enabling fine control over the position of the coaptation element within the valve plane, as seen in FIG. 41, a series of two or more anchors 340 could be deployed in various areas of the RV (including possibly the papillary muscles). The attached anchor rails 342 could all extend through a lumen of the coaptation element (not shown). In order to re-position the coaptation element, the tension on any given anchor rail 342 could be altered independently at the access site, thus increasing or decreasing the degree of tethering on the coaptation element in a certain direction. For example, to move the coaptation element to a more posterior position within the valve, the anchor rail 342 corresponding to the more posterior anchor 340 could be pulled more taught. Once the desired position is achieved, the relative lengths of all the anchor rails could be fixed with respect to the coaptation element catheter via a locking or clamping mechanism at the proximal end of the device. The anchor rails referenced previously could instead be cable wires (with no lumen) in order to minimize the profile of the coaptation element catheter given that multiple anchor attachments will need to fit within the device inner lumen. In order to facilitate easily distinguishing which cable attaches to which anchor, the catheter could contain a series of lumens (at least two) for cable wires which would be labeled based on anatomical location of the corresponding anchor. Therefore, at the proximal end of the device, it would be clear which cable would be required to pull in order to translate the coaptation element in a certain direction.

FIGS. 42A and 42B show operation of a centering balloon 350 that helps ensure proper positioning of an anchor 352 at the apex of the right ventricle. A series of experiments in a bench-top pulsatile flow model with porcine hearts has emphasized the importance of RV anchor position for achieving central location of the coaptation element within the valve. Thus, it may be necessary to utilize an accessory catheter 354 for the present device to help facilitate delivery of the anchor 352 to the ideal location within the ventricle, or the centering balloon 250 may be mounted on the distal end of the delivery/anchoring catheter itself. One such approach relies on using the annulus itself to guide the anchor shaft. For instance, a perfusion balloon 350 large enough to fill the entire valve could be inflated within the tricuspid annulus, therefore counting on opposition between the annulus and the perfusion balloon to orient the angle of the catheter lumen directly normal to and through the center of the valve plane. FIG. 42A shows the unwanted position of the anchor 350 before balloon inflation, while FIG. 42B shows the desired positioning at the RV apex after the balloon 350 is inflated. At this point, the anchor shaft would pass through the lumen of the perfusion balloon catheter (either an accessory catheter or the delivery catheter itself), which is oriented so as to guide the anchor to the ideal central location along the anterior-posterior axis of the RV apex. The centering balloon 250 allows the delivery system to track into the RV while avoiding chords and ensuring central placement rather than between leaflets.

Figure 43:
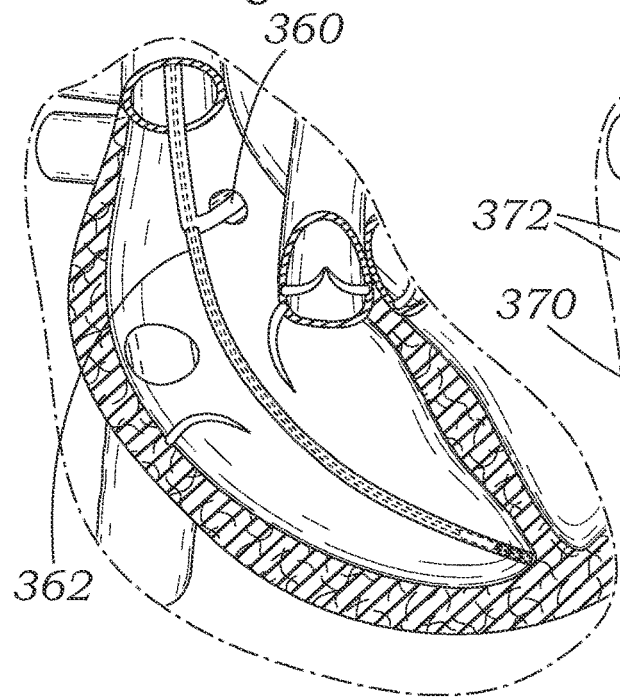
FIG. 43 illustrates a step in directing an anchoring catheter to the apex of the right ventricle using an L-shaped stabilizing catheter secured within a coronary sinus.

FIG. 43 illustrates a step in directing an anchoring catheter 360 to the apex of the right ventricle using an L-shaped stabilizing catheter 362 secured within a coronary sinus. This configuration addresses the challenge of guiding the anchor delivery. The catheter 362 is capable of deflecting into an L-shape, and would be advanced from the SVC, into the right atrium, then into the coronary sinus, which would provide a stabilizing feature for the guide catheter. The catheter 362 could be maneuvered further in or out of the coronary sinus such that the "elbow" of the L-shape is positioned directly above the center of the valve, then the anchor catheter 360 could be delivered through the lumen of the guide catheter 362 and out a port at the elbow of the L-shape. A temporary stiffening "stylet" (not shown) could be used through the anchor rail lumen to ensure the anchor is delivered directly downwards to the ideal point at the RV apex.

Figure 44:
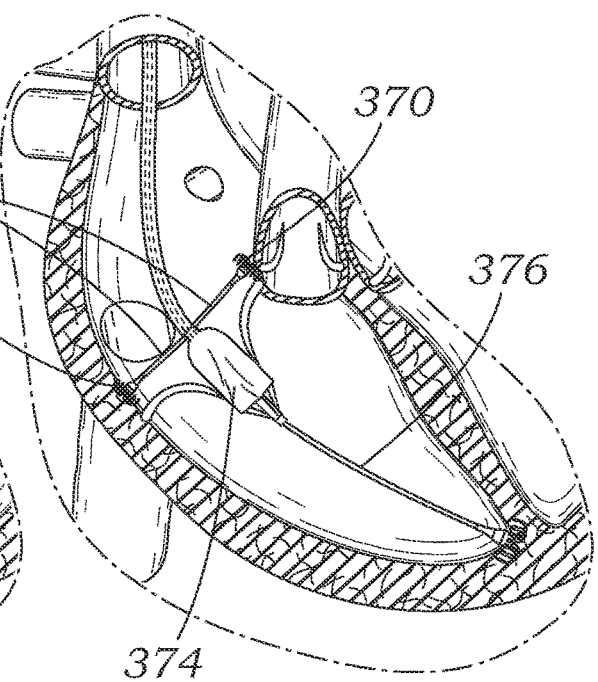
FIG. 44 schematically illustrates a stabilizing rod extending laterally from a regurgitation reduction device delivery catheter in the right atrium above the tricuspid valve.

If any of the previously described anchoring options involving any combination of the RV, SVC, and IVC prove to be undesirable, the coaptation element could instead be anchored directly to the annulus. As shown in FIG. 44, a series of at least two anchors 370 (similar to the helical RV anchors) could be deployed into the fibrous portion of the annulus, then cables or stabilizing rods 372 could be used to hang or suspend the coaptation element 374 within the annulus plane. Each support cable or rod 372 would need to be relatively taught, so as to prevent motion of the device towards the atrium during systole. Any number of supports struts greater than two could be utilized. The support cables for suspending the coaptation element from the annulus could be relatively flexible, and thus the position and mobility of the device would be altered via tension in the cables. Alternatively, the support elements could be relatively stiff to decrease device motion, but this would require changing anchor position to reposition the coaptation element. Although an anchor 376 to the RV apex is shown, the dual annulus anchors 370 might obviate the need for a ventricular anchor.

Figure 45:
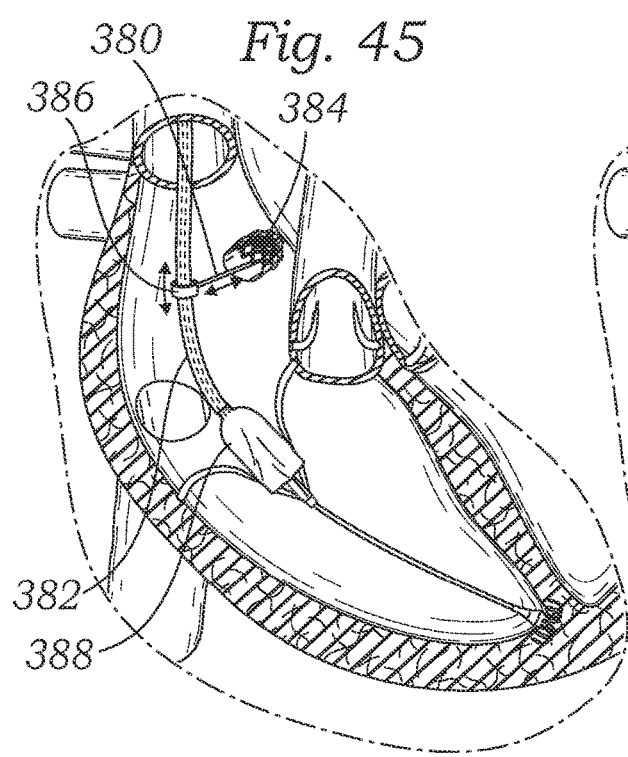
FIG. 45 illustrates an adjustable stabilizing rod mounted on the delivery catheter and secured within the coronary sinus.

The general concept of cylindrical stent-based anchor mechanisms for the device could be applied in other structures near the tricuspid valve such as the coronary sinus. For instance, FIG. 45 illustrates an adjustable stabilizing rod 380 mounted on a delivery catheter 382 and secured to an anchor 384 within the coronary sinus. The stabilizing rod 380 attaches via an adjustable sleeve 386 to the catheter 382, thus suspending the attached coapting element 388 down into the regurgitant orifice. A sliding mechanism on the adjustable sleeve 386 permits adjustment of the length between the coronary sinus anchor 384 and the coaptation device 388, thus allowing positioning of the coaptation element at the ideal location within the valve plane. For further stability, this coronary sinus anchoring concept could also be coupled with a traditional anchor in the RV apex, as shown.

Figure 46:
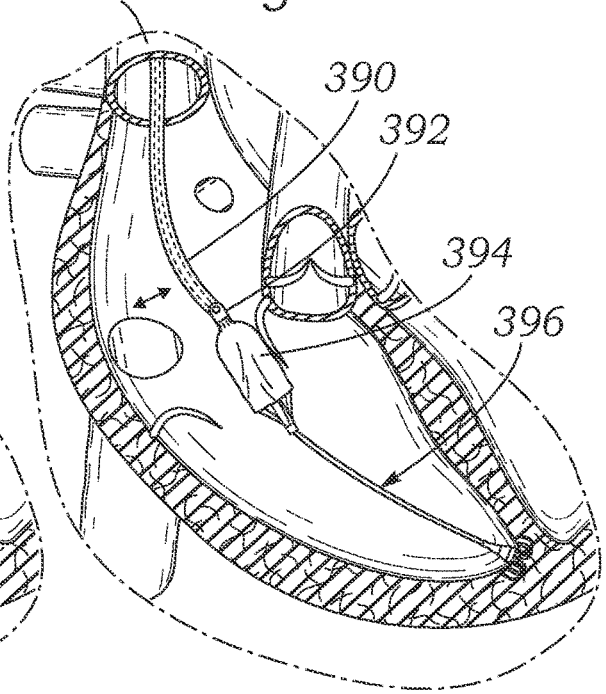
FIG. 46 illustrates an alternative delivery catheter having a pivot joint just above the coapting element.

While venous access to the RV through the subclavian vein and into the superior vena cava is a routine procedure with minimal risk for complications, the fairly flat access angle of the SVC with respect to the tricuspid valve plane presents a number of challenges for proper orientation of the present coaptation element within the valve. If the catheter were not flexible enough to achieve the correct angle of the coaptation element with respect to the valve plane by purely passive bending, a flex point could be added to the catheter directly proximal to the coaptation element via a pull wire attached to a proximal handle through a double lumen extrusion. For instance, FIG. 46 illustrates an alternative delivery catheter 390 having a pivot joint 392 just above the coapting element 394 for angle adjustment. If a given combination of SVC access angle and/or RV anchor position resulted in a crooked coaptation element within the valve plane, the catheter 390 could be articulated using the pull wire (not shown) until proper alignment is achieved based on feedback from fluoroscopic views.

Additional flex points could be added to further facilitate control of device angle, e.g. another flex point could be added distal to the coaptation element 394 to compensate for the possible case that the RV wall angle (and thus the anchor angle) is skewed with respect to the valve plane. This would require an additional independent lumen within the catheter body 390 to facilitate translation of another pull wire to operate the second flex feature. Alternatively, if a single flex point proximal to the coaptation element were determined to be sufficient for orienting the device, and if the catheter were rigid enough to resist the forces of systolic flow, the section 396 of the device distal to the coaptation element could be removed all together. This would leave only one anchoring point for the device in the SVC or subcutaneously to the subclavian vein. Also, as an alternative to an actively-controlled flex point, the catheter could contain a shape-set shaft comprised of Nitinol or another shape memory material, which would be released from a rigid delivery sheath into its "shaped" form in order to optimize device angle from the SVC. It could be possible to have a few catheter options of varying pre-set angles, yet choose only one after evaluation of the SVC-to-valve plane angle via angiographic images.

Instead of using an active mechanism within the catheter itself to change its angle, another embodiment takes advantage of the surrounding anatomy, i.e. the SVC wall. FIGS. 47A and 47B show two ways to anchor the delivery catheter 400 to the superior vena cava SVC for stabilizing a coapting element 402. For example, a variety of hooks or anchors 404 could extend from a second lumen within the catheter 402 with the ability to grab onto the SVC wall and pull the catheter in that direction (FIGS. 47A and 47B). Alternatively, a stiffer element could extend outwards perpendicular to the catheter axis to butt up against the SVC wall and push the catheter in the opposite direction. For especially challenging SVC geometries, such a mechanism could potentially be useful for achieving better coaxial alignment with the valve.

Figure 48A:
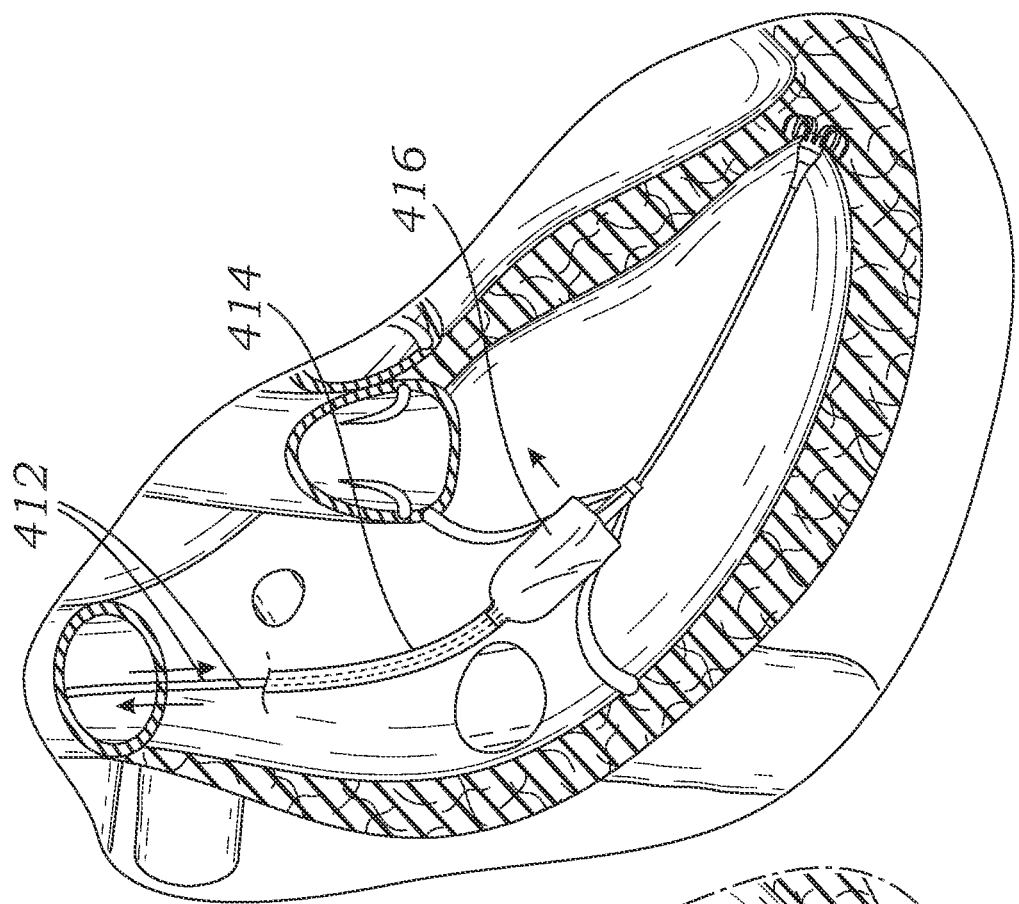
FIGS. 48A and 48B show a regurgitation reduction device having pull wires extending therethrough for altering the position of the coapting element within the tricuspid valve leaflets.
Figure 48B:
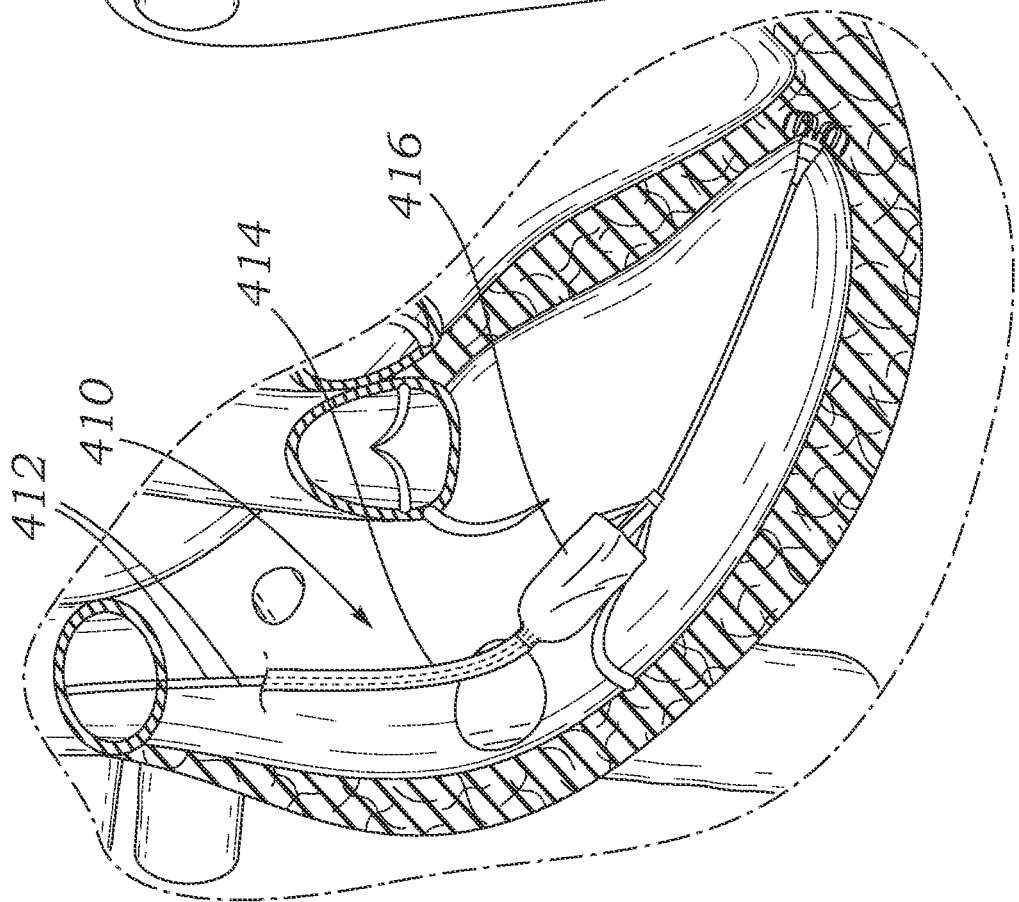

FIGS. 48A and 48B show an active regurgitation reduction device 410 having pull wires 412 extending through the delivery catheter 414 for altering the position of the coapting element 416 within the tricuspid valve leaflets. If the coapting element 416 is located out of the middle of the valve leaflets such that it does not effectively plug any regurgitant jets, which can be seen on echocardiography, then one of the pull wires 412 can be shortened or lengthened in conjunction with rotating the catheter 414 to reposition the coapting element 416, such as seen from FIG. 48A to FIG. 48B.

Figure 49:
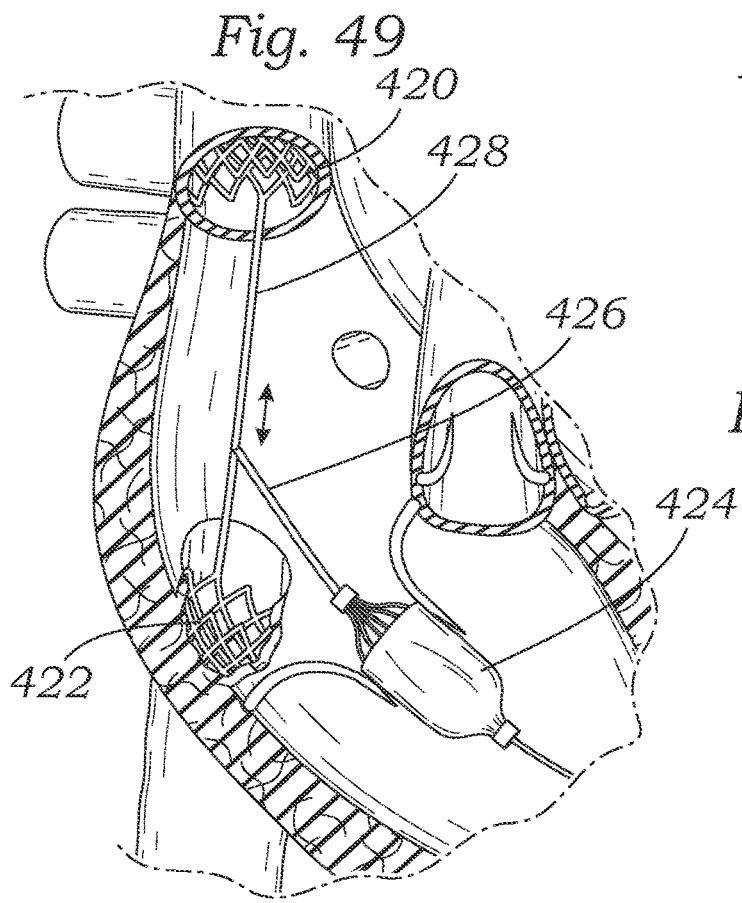
FIG. 49 shows a regurgitation reduction device anchored with stents in both the superior and inferior vena cava and having rods connecting the stents to the atrial side of the coapting element.

Although pacemaker leads are frequently anchored in the right ventricle with chronic success, the anchor for the present device would see significantly higher cyclic loads due to systolic pressure acting on the coaptation element. Given that the right ventricle wall can be as thin as two millimeters near the apex and the tissue is often highly friable in patients with heart disease, anchoring a device in the ventricle may not be ideal. An alternative anchoring approach could take advantage of the fairy collinear orientation of the superior and inferior vena cava, wherein, as seen in FIG. 49, two stent structures 420, 422 would effectively "straddle" the tricuspid valve by expanding one in the superior vena cava and the other in the inferior vena cava. The coaptation element 424 would then hang down through the tricuspid valve plane from an atrial shaft 426 attached to a connecting wire or rod 428 between the two caval stents 420, 422. In order to resist motion of the coaptation element under systolic forces, the shaft 426 from which the coaptation element 424 hangs would be fairly rigid under compressive and bending stresses. The coaptation element 424 would desirably be positioned within the valve using a sliding mechanism along the connecting rod 428 between the two caval stents.

The coaxial orientation of the SVC and IVC could also be leveraged for delivering an anchor into the RV. A delivery catheter could be passed through the SVC into the IVC, and a "port" or hole off the side of the delivery catheter could be aligned with the center of the valve. At this point, the anchor could be passed through the lumen of the delivery system and out the port, resulting in a direct shot through the center of the annulus and to the RV wall in the ideal central anchor location.

This concept could potentially be applied to the left side of the heart as well, to address mitral regurgitation. A coaptation element could reside between the mitral valve leaflets with anchors on both the proximal and distal ends: one attaching to the septal wall, and the other anchoring in the left atrial appendage. The septal anchor could be a helical or hook-style anchor, whereas the left atrial appendage anchor could be an expandable metallic structure with a plurality of struts or wireforms designed to oppose against the appendage wall and provide stability to the coaptation element.

Pacemaker leads frequently lead to tricuspid regurgitation (TR) by pinning a leaflet or interfering with leaflet mobility. In this particular embodiment, a device, a gap filler, is designed to be introduced over the offending pacemaker lead (of course, applicable also to those with organic tricuspid regurgitation and a pacemaker lead in place). The invention is a tricuspid regurgitant volume gap filler that is placed over the existing pacemaker lead via a coil wound over the lead or a slit sheath approach, which acts like a monorail catheter. The gap filler catheter is advanced over the pacemaker lead and the tricuspid regurgitation is evaluated by echo while the monorail gap filler device is placed into the regurgitant orifice. The proximal end of the gap filler allows for crimping and truncating the catheter post-balloon inflation or gap filler deployment. This mates the monorail gap filler to the pacemaker lead at the proper position within the tricuspid valve.

Figure 51A:
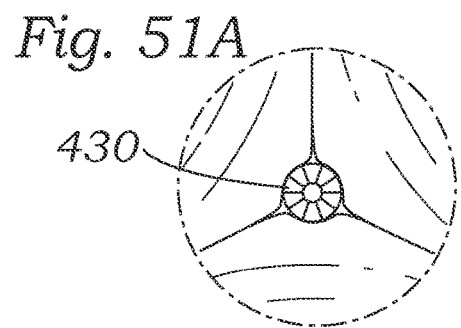
FIGS. 51A and 51B are radial sectional views through the coapting element as seen in FIGS. 50A and 50B, respectively.
Figure 51B:
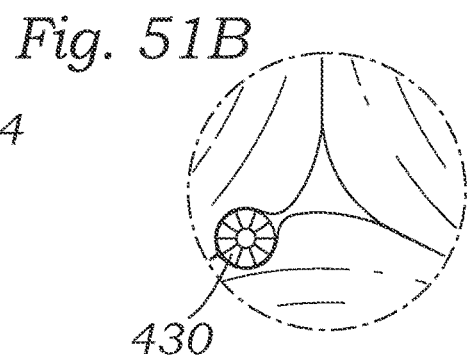
Figure 50A:
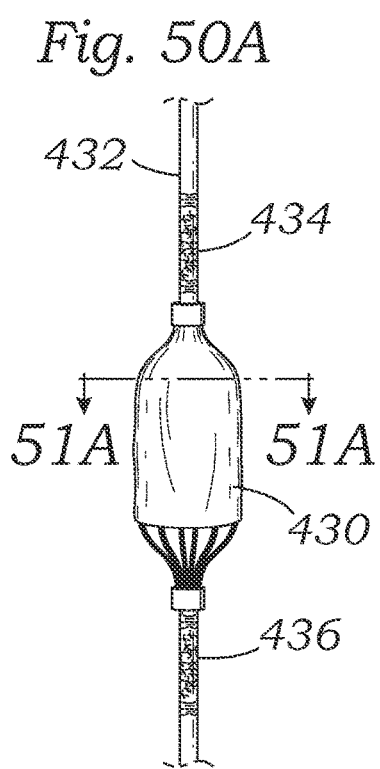
FIGS. 50A-50C are schematic views of a coapting element mounted for lateral movement on a flexible delivery catheter that collapses and allows rotation for seating centrally in the valve plane even if the delivery catheter is not central.
Figure 50B:
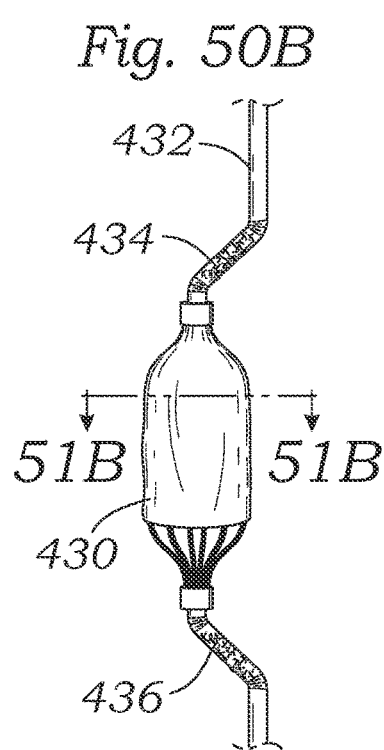
Figure 50C:
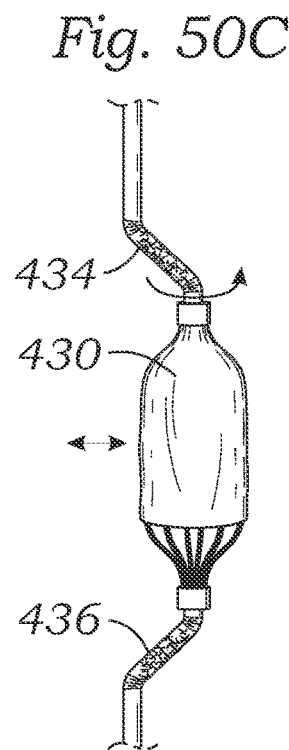

FIGS. 50-51 are schematic views of a coapting element 430 mounted for lateral movement on a flexible delivery catheter 432 that features controlled buckling. It is challenging to reposition the coaptation element 430 from an off-center location to the ideal central location within the valve plane, given a fixed angle from the SVC and a fixed anchor position in the RV. The device catheter 432 could be comprised of a fairly stiff shaft except for two relatively flexible regions 434, 436 directly proximal and distal to the coaptation element section. The farthest distal section of the coaptation catheter 432 could be locked down relative to the anchor rail over which it slides, and then the catheter 432 could be advanced distally thus compressing it and causing the two flexible sections 434, 436 to buckle outwards and displace the coaptation element laterally with respect to the catheter axis (see FIG. 50C). At this point, the user could employ a combination of sliding and rotating of the catheter to reposition the coaptation element 430 within the valve using short-axis echo feedback. Instead of locking the distal end of the catheter onto an anchor rail before adjustment, if the catheter were comprised of multiple lumens, the outer lumen could slide distally relative to the inner lumen, thus producing the same buckling effect.

In another embodiment, not shown, an alternative approach could be to rely on the contractile motion of the heart to move a tapered coaptation element in and out of the tricuspid valve plane. A tapered coaptation element, with a smaller cross-section proximally (towards the atrium) and larger cross-section distally (towards the ventricle), would be attached to a rigid distal railing and anchor. During systolic contraction, the anchor and therefore the attached coaptation element would move towards the annulus, thus allowing the tricuspid leaflets to coapt around the larger cross-section of the device. Conversely, diastolic expansion of the RV would bring the anchor and therefore the coaptation element downwards such that the smaller cross-section of the device is now within the annulus plane, thus minimizing diastolic stenosis. A combination of a tapered element with a spring could be used if RV wall motion towards the annulus is not sufficient to move the device.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A method of reducing regurgitation between native leaflets of an atrioventricular heart valve, comprising:
   advancing a sheath into the body;
   advancing a delivery catheter through the sheath, the delivery catheter having an internal lumen and a distal end portion, the catheter being made of material suitable for long-term implant in the human body, the catheter having a valve leaflet coaptation element mounted over the distal end portion, the coaptation element having a smooth outer cover of a biocompatible material, and a flexible inner support comprising super-elastic struts to allow the coaptation element to collapse into a compressed configuration for passage through the sheath, the coaptation element being made of material suitable for implant in the human body;
   positioning the coaptation element within the heart valve;
   permitting the coaptation element to radially expand from the compressed configuration to an enlarged configuration for filling a gap between the native leaflets of the heart valve; and
   fixing a position of the coaptation element relative to the heart valve by connecting the coaption element to a proximal anchor, wherein the proximal anchor is secured to surrounding tissue.

2. The method of claim 1, wherein the super-elastic struts are made of Nitinol.

3. The method of claim 1, wherein the biocompatible material of the outer cover is pericardium.

4. The method of claim 1, wherein the biocompatible material of the outer cover is formed of polycarbonate urethane, wherein the catheter is also made of polycarbonate urethane and distal and proximal necks of the outer cover are heat bonded to the catheter.

5. The method of claim 1, wherein the outer cover is open at both ends.

6. The method of claim 1, wherein the proximal anchor is adapted to anchor to tissue located at one of either an annulus of the heart valve, the inferior vena cava (IVC), or the right atrium (RA) and a length sufficient to extend from the proximal anchor to the heart valve.

7. The method of claim 1, wherein the step of advancing the delivery catheter includes introducing the catheter to the subclavian vein and advancing the catheter through the superior vena cava and from there into the right atrium RA to the tricuspid valve.

8. The method of claim 1, further including an elongated flexible anchor rail made of material suitable for implant in the human body and having a distal anchor, and the method includes advancing the anchor rail over a guidewire and across the heart valve to the ventricle, and anchoring the anchor within the ventricle, and the step of advancing the delivery catheter includes advancing the catheter over the anchor rail, and the step of anchoring a position of the coaptation element includes anchoring the catheter relative to the anchor rail.

9. The method of claim 1, wherein the coaptation element defines an asymmetric shape along its longitudinal axis having an enlarged belly region just distal from a midline relative to a narrower proximal end.

10. The method of claim 1, wherein the coaptation element has a rounded triangular shape in radial section.

11. A method of reducing regurgitation between native leaflets of an atrioventricular heart valve, comprising:
    advancing a sheath into the body;
    advancing a delivery catheter through the sheath, the delivery catheter having an internal lumen and a distal end portion, the catheter being made of material suitable for long-term implant in the human body, the catheter having a valve leaflet coaptation element mounted over the distal end portion, the coaptation element having an outer cover of pericardium, and a flexible inner support comprising Nitinol struts to allow the coaptation element to collapse into a compressed configuration for passage through the sheath, the coaptation element being made of material suitable for implant in the human body;
    positioning the coaptation element within the heart valve;
    permitting the coaptation element to radially expand from the compressed configuration to an enlarged configuration for filling a gap between the native leaflets of the heart valve; and
    fixing a position of the coaptation element relative to the heart valve and thereby reducing regurgitation between the native leaflets of the heart valve.

12. The method of claim 11, wherein the outer cover is open at both ends.

13. The method of claim 11, wherein the catheter has a proximal anchor adapted to anchor into tissue located at one of either an annulus of the heart valve, the inferior vena cava (IVC), or the right atrium (RA) and a length sufficient to extend from the proximal anchor to the heart valve.

14. The method of claim 11, wherein the step of advancing the delivery catheter includes introducing the catheter to the subclavian vein and advancing the catheter through the superior vena cava and from there into the right atrium RA to the tricuspid valve.

15. The method of claim 11, further including an elongated flexible anchor rail made of material suitable for implant in the human body and having a distal anchor, and the method includes advancing the anchor rail over a guidewire and across the heart valve to the ventricle, and anchoring the anchor within the ventricle, and the step of advancing the delivery catheter includes advancing the catheter over the anchor rail, and the step of anchoring a position of the coaptation element includes anchoring the catheter relative to the anchor rail.

16. The method of claim 15, further including a locking collet on a proximal end of the catheter for securing the axial position of the catheter on the anchor rail, the locking collet being made of material suitable for implant in the human body.

17. The method of claim 11, wherein the coaptation element defines an asymmetric shape along its longitudinal axis having an enlarged belly region just distal from a midline relative to a narrower proximal end.

18. The method of claim 11, wherein the coaptation element has a rounded triangular shape in radial section.

\* \* \* \* \*